(12) United States Patent
Langkilde

(10) Patent No.: US 11,903,955 B2
(45) Date of Patent: *Feb. 20, 2024

(54) METHODS OF TREATING HEART FAILURE WITH REDUCED EJECTION FRACTION

(71) Applicant: ASTRAZENECA AB, Södertälje (SE)

(72) Inventor: Anna Maria Langkilde, Södertälje (SE)

(73) Assignee: ASTRAZENECA AB, Södertälje (SE)

( * ) Notice: Subject to any disclaimer, the term of this patent is extended or adjusted under 35 U.S.C. 154(b) by 113 days.

This patent is subject to a terminal disclaimer.

(21) Appl. No.: 17/184,746

(22) Filed: Feb. 25, 2021

(65) Prior Publication Data

US 2021/0260083 A1 Aug. 26, 2021

Related U.S. Application Data

(63) Continuation of application No. 16/812,745, filed on Mar. 9, 2020, now Pat. No. 10,973,836.

(Continued)

(51) Int. Cl.
*A61P 9/04* (2006.01)
*A61K 31/351* (2006.01)
*A61K 31/70* (2006.01)

(52) U.S. Cl.
CPC ............ *A61K 31/70* (2013.01); *A61K 31/351* (2013.01); *A61P 9/04* (2018.01)

(58) Field of Classification Search
None
See application file for complete search history.

(56) References Cited

U.S. PATENT DOCUMENTS 8,883,743 B2 * 11/2014 Washburn ............. A61K 45/06
514/23
9,198,925 B2 * 12/2015 Bindra ..................... A61P 3/04
(Continued)

FOREIGN PATENT DOCUMENTS

KR   10-2015-0138859   12/2015
KR   10-2018-122004    11/2018
(Continued)

OTHER PUBLICATIONS

Davis et al., "Heart Failure With Preserved and Reduced Left Ventricular Ejection Fraction in the Antihypertensive and Lipid-Lowering Treatment to Prevent Heart Attack Trial" Circulation vol. 118 pp. 2259-2267 DOI: 10.1161/CIRCULATIONAHA.107. 762229 (Year: 2008).*

(Continued)

*Primary Examiner* — Eric Olson
(74) *Attorney, Agent, or Firm* — Finnegan, Henderson, Farabow, Garrett & Dunner, LLP

(57) ABSTRACT

The present disclosure is directed to methods of treating patients with heart failure with reduced ejection fraction (HFrEF), with and without Type 2 diabetes, with an SGLT2 inhibitor, such as dapagliflozin. The methods disclosed herein can reduce the risk of a composite outcome of a first episode of worsening heart failure (hospitalization for heart failure or an urgent heart failure visit) or death from cardiovascular causes. Each of the three components of this composite outcome can also be reduced, as well as the total number of heart failure hospitalizations and deaths from cardiovascular causes. SGLT2 inhibitors, such as dapagliflozin, can also reduce a worsening of heart failure symptoms. The methods disclosed herein can also improve heart failure symptoms, health status, and quality of life.

27 Claims, 30 Drawing Sheets

Related U.S. Application Data

(60) Provisional application No. 62/985,407, filed on Mar. 5, 2020, provisional application No. 62/969,181, filed on Feb. 3, 2020, provisional application No. 62/960,756, filed on Jan. 14, 2020, provisional application No. 62/946,625, filed on Dec. 11, 2019, provisional application No. 62/930,673, filed on Nov. 5, 2019, provisional application No. 62/893,849, filed on Aug. 30, 2019.

(56) References Cited

U.S. PATENT DOCUMENTS

| | | | |
|---|---|---|---|
| 9,394,291 | B2 | 7/2016 | O'Mahony |
| 9,757,404 | B2* | 9/2017 | Gannedahl ............... A61P 3/04 |
| 10,973,836 | B2 | 4/2021 | Langkilde |
| 2008/0058379 | A1 | 3/2008 | Eckhardt |
| 2017/0266152 | A1 | 9/2017 | Uli et al. |
| 2019/0192482 | A1 | 6/2019 | Minamino |
| 2020/0054656 | A1 | 2/2020 | Kim |
| 2020/0078382 | A1 | 3/2020 | Langkilde |
| 2021/0060043 | A1 | 3/2021 | Langkilde |
| 2022/0023252 | A1* | 1/2022 | Langkilde ............ A61K 9/0053 |
| 2022/0023321 | A1* | 1/2022 | Langkilde ............... A61P 13/12 |

FOREIGN PATENT DOCUMENTS

| | | |
|---|---|---|
| KR | 10-1943382 | 1/2019 |
| WO | WO 2014/161918 A1 | 10/2014 |
| WO | WO 2017/157816 A1 | 9/2017 |
| WO | WO 2018/142422 | 8/2018 |
| WO | WO 2019/059557 | 3/2019 |
| WO | WO 2020/016335 A1 | 1/2020 |

OTHER PUBLICATIONS

Smith et al., "Chronic Kidney Disease and Outcomes in Heart Failure With Preserved Versus Reduced Ejection Fraction The Cardiovascular Research Network PRESERVE Study" Circ Cardiovasc Qual Outcomes vol. 6 pp. 333-342 DOI: 10.1161/CIRCOUTCOMES. 113.000221 (Year: 2013).*

Radovanovic et al., Treatment and outcomes of patients with recurrent myocardial infarction: A prospective observational cohort study: Journal of Cardiology vol. 68 pp. 498-503 http://dx.doi.org/10.1016/j.jcc.2015.11.013 (Year: 2016).*

Wang et al., "TSOC-HFrEF Registry: A Registry of Hospitalized Patients with Decompensated Systolic Heart Failure: Description of Population and Management" Acta Cardiol Sin vol. 32 pp. 400-411 (Year: 2016).*

Wilding et al., "Dapagliflozin therapy for type 2 diabetes in primary care: Changes in HbA1c, weight and blood pressure over 2 years follow-up" Primary Care Diabetes II (2017) pp. 437-444 (Year: 2017).*

Khoshbaten et al., "Comparison of Left Ventricular Function Between Patients with Non-Alcoholic Fatty Liver Disease and Healthy Individuals" Biomedical and Pharmacology Journal vol. 8 No. 2 pp. 749-754 (Year: 2015).*

Savji et al., "The Association of Obesity and Cardiometabolic Traits With Incident HFpEF and HFrEF" Jacc: Heart Failure vol. 6 No. 8 pp. 701-709 https://doi.org/10.1016/j.jchf.2018.05.018 (Year: 2018).*

Text of decision for *Bayer Schering Pharma AG* v. *Barr Labs., Inc.*, Civil Action No. 05-cv-2308 (PGS)., 2008 BL 43010, 2008 US Dist Lexis 15917, 2008 WL 628592 (D.N.J. Mar. 3, 2008), downloaded from www.bloomberglaw.com (Year: 2008).*

Text of Janssen Pharmaceutica, *Naamloze Vennootschap* v. *Eon Labs Mfg., Inc.*, 134 Fed. Appx. 425 (Fed. Cir. 2005), Court Opinion, downloaded from www.bloomberglaw.com (Year: 2005).*

McCray et al., "Design and Implementation of a National Clinical Trials Registry" Journal of the American Medical Informatics Association vol. 7 No. 3, pp. 313-323 (Year: 2000).*

Zelniker et al., "Cardiac and Renal Effects of Sodium-Glucose Co-Transporter 2 Inhibitors in Diabetes" Journal of the American College of Cardiology vol. 72 No. 15 pp. 1845-1855 (Year: 2018).*

Gandhi et al., "What's a 'Normal' A1c? When is it Misleading?" downloaded from https://diatribe.org/whats-normal-a1c-when-it-misleading (Year: 2017).*

Santos-Gallego et al., "Empagliflozin Ameliorates Adverse Left Ventricular Remodeling in Nondiabetic Heart Failure by Enhancing Myocardial Energetics" Journal of the American College of Cardiology vol. 73 No. 15 pp. 1931-1944 (Year: 2019).*

Cappetta et al., "Dapagliflozin ameliorates diastolic function in a non-diabetic model of heart failure" Naunyn-Schmiedeberg's Archives of Pharmacology, (Feb. 2019) vol. 392, Suppl. 1, p. S5 abstract 9 (Year: 2019).*

Akerblom, A. et al. (2019), "Effects of DAPAgliflozin on CARDiac substrate uptake, myocardial efficiency, and myocardial contractile work in type 2 diabetes patients—a description of the DAPACARD study," *UPSALA Journal of Medical Sciences*; 124(1): 59-64.

Bhatt, D.L., et al. (2019), "the DAPA-HF Trial: A Momentous Victory in the War against Heart Failure," *Cell Metab*; 30(5): 847-849.

Chemical Abstracts Registry No. 1850385-64-6, AZD9977 (Year: 2016).

Clinical Study Protocol Study to Evaluate the Effect of Dapagliflozin on the Incidence of Worsening Heart Failure or Cardiovascular Death in Patients with Chronic Heart Failure with Reduced Ejection Fraction, Study Code D1699C00001. Version 2.0., Date Oct. 26, 2017 (https://www.clinicaltrials.gov/ProvidedDocs/24/NCT03036124/Prot_000.pdf).

Connelly, K. A., et al. (2018), "Can We DECLARE a Victory against Cardio-Renal Disease in Diabetes," *Cell Metab*; 28(6): 813-815.

Custodio, J. S. et al., "SGLT2 inhibition and heart failure-current concepts," *Heart Failure Reviews* (2018) 23:409-418.

"Dapagliflozin for chronic heart failure with reduced ejection fraction," Health Technology Briefing May 2019, NIHR Innovation Observatory (7 pages).

Docherty, K. F. et al. (2020), "Effects of dapagliflozin in DAPA-HF according to background heart failure therapy," *Eur Heart J*; doi: 10.1093/eurheartj/ehaa183 (14 pages).

"Farxiga met primary endpoint in landmark Phase III DAPA-HF trial for the treatment of patients with heart failure," published Aug. 20, 2019 (3 pages) (https://www.astrazeneca.com/media-centre/press-releases/2019/farxiga-met-primary-endpoint-in-landmark-phase-iii-dapa-hf-trial-for-the-treatment-of-patients-with-heart-failure-20082019.html).

Fitchett et al., "Heart failure outcomes with empagliflozin in patients with type 2 diabetes at high cardiovascular risk: results of the EMPA-REG OUTCOME® trial," Eur Heart J, 2016; 37: 1526-1534.

Furtado, R. H. M. et al. (2019), "Dapagliflozin and Cardiovascular Outcomes in Patients with Type 2 Diabetes Mellitus and Previous Myocardial Infarction," *Circulation*; 139(22): 2516-2527.

Gandhi, "What's a "Normal" A1C? When is it Misleading?" Internet article, https://diatribe.org/whats-normal-a1c-when-it-misleading, Oct. 31, 2017 (11 pages).

Green et al., "Development and Evaluation of the Kansas City Cardiomyopathy Questionnaire: A New Health Status Measure for Heart Failure" Journal of the American College of Cardiology, vol. 35, No. 5, pp. 1245-1255 (Year: 2000).

Hallow, K. M. et al., "Why do SGLT2 inhibitors reduce heart failure hospitalization? A differential volume regulation hypothesis," *Diabetes Obes Metab*; 20(3): 479-487.

History of changes for Study NCT02751398, version Aug. 25, 2016.
History of changes for Study NCT03036124, version Jan. 26, 2017.
History of changes for Study NCT03036124, version Jan. 10, 2019.
History of changes for Study NCT03030235, version Jan. 20, 2017.
International Search Report and Written Opinion for International Application No. PCT/EP2020/056211, dated Jun. 19, 2020 (15 pages).

Jensen, J. et al., "Empagliflozin in heart failure patients with reduced ejection fraction: a randomized clinical trial (Empire HF)," *Trials* (2019) 20:374 (8 pages).

(56) References Cited

OTHER PUBLICATIONS

Joseph et al., "Acute Decompensated Heart Failure," Texas Heart Institute Journal, vol. 36, No. 6, pp. 510-520 (Year: 2009).

Kalra, S. "Cardiorenal syndromes and SGLT2 inhibitor usage," Medicine Matters Diabetes—Aug. 6, 2019 (5 pages).

Kaplinsky, E. (2020), "DAPA-HF trial: dapagliflozin evolves from a glucose-lowering agent to a therapy for heart failure" *Drugs Context*; 9: doi: 10.7573/dic.2019-11-3 (7 pages).

Kato, E. T., et al. (2020) "Effect of Dapagliflozin on Heart Failure and Mortality in Type 2 Diabetes Mellitus," *Circulation*; 139(22): 2528-2536.

Komajda et al., "Heart failure events with rosiglitazone in type 2 diabetes: data from the RECORD clinical trial," Eur Heart J, 2010; 31: 824-831.

Kosiborod, M. N. et al. (2020), "Effects of Dapagliflozin on Symptoms, Function, and Quality of Life in Patients with Heart Failure and Reduced Ejection Fraction: Results from the DAPA-HF Trial," *Circulation*; 141(2): 90-99.

Kosiborod, M. M.D. et al. (2017), "Lower Risk of Heart Failure and Death in Patients Initiated on Sodium-Glucose Cotransporter-2 Inhibitors Versus Other Glucose-Lowering Drugs: The CVD-REAL Study (Comparative Effectiveness of Cardiovascular Outcomes in New Users of Sodium-Glucose Cotransporter-2 Inhibitors)," *Circulation*, 136: 249-259, DOI: 10.1161/CIRCULATIONAHA.117.029190 (92 pages, including supplemental material).

Lago et al., "Congestive heart failure and cardiovascular death in patients with prediabetes and type 2 diabetes given thiazolidinediones: a meta-analysis of randomized clinical trials," Lancet, 2007; 370: 1129-1136.

Lan et al., "The effects of sodium-glucose cotransporter 2 inhibitors on left ventricular function: current evidence and future directions," ESC Heart Failure, 2019; 6: 927-935.

Laure et al., "Role of senescence mechanisms in the transitions from cardiac hypertrophy to heart failure in H11K-transgenic mouse "Archives of Cardiovascular Diseases Supplements, vol. 2, p. 19, abstract 0354 (Year: 2012).

Mahaffey et al., "Canagliflozin for primary and secondary prevention of cardiovascular events: results from the CANVAS Program (Canagliflozin Cardiovascular Assessment Study)," Circulation, 2018; 137: 323-334.

Martinez, F. A. et al. (2020), "Efficacy and Safety of Dapagliflozin in Heart Failure with Reduced Ejection Fraction According to Age: Insights from DAPA-HF," *Circulation*; 141(2): 100-111.

Mayo Clinic article, "Arteriosclerosis/atherosclerosis" download from https://www.mayoclinic.org/diseases-conditions/artheriosclerosis-atherosclerosis/symptomscauses/syc-20350569?p=1 (Year: 2018).

Mcmurray, J. J. V. et al. (2019), "The Dapagliflozin and Prevention of Adverse-outcomes in Heart Failure (DAPA-HF) trial: baseline characteristics," *Eur J Heart Fail*; 21(11): 1402-1411.

Mcmurray, J. J. V. et al. (2019), "A trial to evaluate the effect of the sodium-glucose co-transporter 2 inhibitor dapagliflozin on morbidity and mortality in patients with heart failure and reduced left ventricular ejection fraction (DAPA-HF)," *Eur J Heart Fail* 21(5): 665-675.

Mcmurray, J. J. V. et al. (2020), "The Dapagliflozin and Prevention of Adverse Outcomes in Heart Failure Trial (DAPA-HF) in context," *Eur Heart J*; doi: 10.1093/eurheartj/ehz916 (4 pages).

Mcmurray, J. J. V. et al. (2019), "Dapagliflozin in Patients with Heart Failure and Reduced Ejection Fraction," *N Engl J Med*; 381(21): 1995-2008.

Nassif, M.E. et al. (2019), "Dapagliflozin Effects on Biomarkers, Symptoms, and Functional Status in Patients with Heart Failure Ejection Fraction: The DEFINE-HF Trial," *Circulation*; 140(18): 1463-1476.

Neal, B., M.D. et al. (2017), "Canagliflozin and Cardiovascular and Renal Events in Type 2 Diabetes," *N Engl J Med*; 377: 644-657.

Oh, C. et al., "Cardioprotective Potential of an SGLT2 Inhibitor Against Doxorubicin-Induced Heart Failure," *Korean Circulation Journal*, Dec. 2019; 49(12):1183-1195.

Oldgren, J. et al. (Mar. 24, 2020), "Effects of 6 Weeks of Treatment with Dapagliflozin, a Sodium-Glucose Co-Transporter 2 Inhibitor, on Myocardial Function and Metabolism in Type 2 Diabetes Patients: A Randomized Placebo-Controlled Study," ACC.20, Poster Abstract; *JACC*; 75(11): Presentation No. 1112-210.

Packer et al., "Effects of sodium-glucose cotransporter 2 inhibitors for the treatment of patients with heart failure: proposal of a novel mechanism of action," JAMA Cardiol, 2017; 2: 1025-1029.

Packer et al., "Evaluation of the effect of sodium-glucose co-transporter 2 inhibition with empagliflozin on morbidity and mortality of patients with chronic heart failure and a reduced ejection fraction: rationale for and design of the EMPEROR-Reduced trial," European Journal of Heart Failure, 2019; 21: 1270-1278.

Packer, M. (2019), "Lessons learned from the DAPA-HF trial concerning the mechanisms of benefit of SGLT2 inhibitors on heart failure events in the context of other large-scale trials nearing completion," *Cardiovasc Diabetol*; 18(1): 129 (4 pages).

Petrie, M. C. et al. (2020), "Effect of Dapagliflozin on Worsening Heart Failure and Cardiovascular Death in Patients with Heart Failure with and without Diabetes," *Jama*; 323(14): 1353-1368.

Raut et al., "miR-30c and miR-181a synergistically modulate p53-p21 pathway in diabetes induced cardiac hypertrophy" Molecular and Cellular Biochemistry, vol. 417, pp. 191-203 (Year: 2016).

Riggs, "The use of SGLT-2 inhibitors in type 2 diabetes and heart failure," Metabolic Syndrome and Related Disorders, 2015; 13(7): 292-297.

Sano, M. et al., "A new class of drugs for heart failure: SGLT2 inhibitors reduce sympathetic overactivity." *Journal of Cardiology*, 71 (2018), 471-476.

Correction to Scirica et al., "Heart failure, saxagliptin, and diabetes mellitus: observations from the SAVOR-TIMI 53 randomized trial," Circulation, 2015; 132: e198 (1 page).

Sattar et al., "SGLT2 inhibition and cardiovascular events: why did EMPA-REG outcomes surprise and what were the likely mechanisms?" Diabetologia, 2016; 59: 1333-1339.

Scirica et al., "Heart failure, saxagliptin, and diabetes mellitus: observations from the SAVOR-TIMI 53 randomized trial," Circulation, 2015; 132: e198

Tanaka et al., "Effects of Sodium Glucose Co-Transporter 2 Inhibitor Canagliflozin in Patients with Type 2 Diabetes and Chronic Heart Failure (CANDLE): An Open-Label, Randomized Controlled Trial," Available at SSRN (2019) (48 pages) http://dx.doi.org/10.2139/ssrn.3343659.

Terry, M, "AstraZeneca's Diabetes Drug Farxiga Decreases Heart Failure Risk," Biospace, Aug. 20, 2019 (4 pages).

Trang, A. et al., "Treating Disease Mechanisms in Patients With Heart Failure and Diabetes Mellitus," *Curr Heart Fail Resp* (2017) 14:445-453.

Urbanek, et al., "Dapagliflozin ameliorates diastolic function in an animal model of hypertensive heart disease in the absence of diabetes," European Journal of Heart Failure, May 2018, vol. 20, Abstract p. 1294 (1 page).

Verma et al., "The metabolodiuretic promise of sodium-dependent glucose cotransporter 2 inhibition: the search for the sweet spot in heart failure," JAMA Cardiol, 2017; 2: 939-940.

Verma, S. (2020), "The DAPA-HF trial marks the beginning of a new era in the treatment of heart failure with reduced ejection fraction," *Cardiovasc Res*; 116(1): e8-e10.

Verma, S. and Mcmurray, J. J. V. (2019), "The Serendipitous Story of SGLT2 Inhibitors in Heart Failure," *Circulation*; 139(22): 2537-2541.

Wiviott, S. D. et al. (2018), "The design and rationale for the Dapagliflozin Effect on Cardiovascular Events (DECLARE)-TIMI 58 Trial," *Am Heart J*; 200: 83-89.

Wiviott, S. D. et al. (2019), "Dapagliflozin and Cardiovascular Outcomes in Type 2 Diabetes," *N Engl J Med*; 380(4): 347-357.

Zannad et al., "Heart failure and mortality outcomes in patients with type 2 diabetes taking alogliptin versus placebo in EXAMINE: a multicentre, randomized, double-blind trial," Lancet, 2015: 385: 2067-2076.

Zinman, B. M.D. et al. (2015), "Empagliflozin, Cardiovascular Outcomes, and Mortality in Type 2 Diabetes," *N Engl J Med*; 373(22): 2117-2128.

(56) References Cited

OTHER PUBLICATIONS

Clinical Study Agreement, AstraZeneca Pharmaceuticals LP (May 3, 2018) (redacted) (29 pages).
Bergagård M, Adult Study Subject Master Study Information and Consent Form, AstraZeneca Pharmaceuticals LP (Oct. 31, 2016) (redacted) (16 pages).
Lim V. G., SGLT2 inhibitors—looking beyond glucose-lowering in diabetes, Cochrane UK (Dec. 16, 2019), <https://uk.cochrane.org/news/sglt2-inhibitors-looking-beyond-glucose-lowering-diabetes> (11 pages).
Byrne C., Targher G., NAFLD: A multisystem disease, *J. Hepatol*, 62:S47-S64 (Apr. 2015).
Rao G., Insulin resistance syndrome, *Am Fam Physician*, 63:1159-63, 1165-66 (Mar. 15, 2001).
Pi-Sunyer X., The medical risks of obesity, *Postgrad Med.*, 121(6):21-33 (Nov. 2009).

* cited by examiner

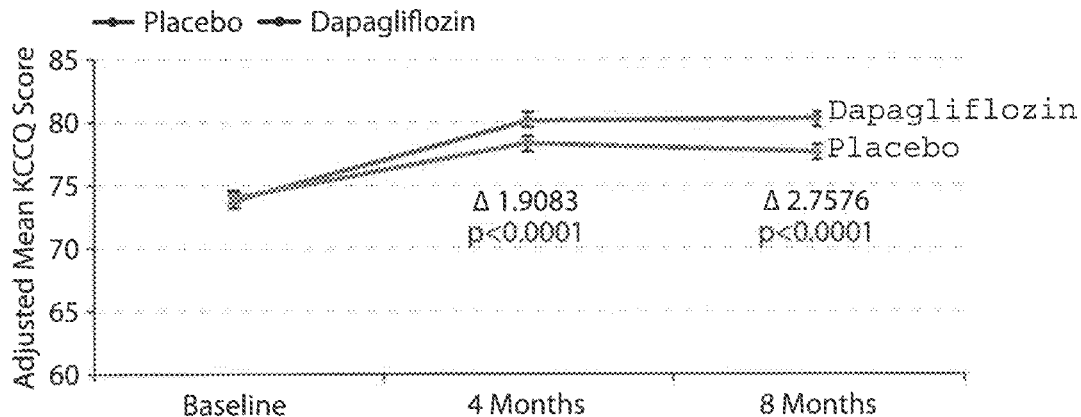
Fig. 7A KCCQ Total Symptom Score
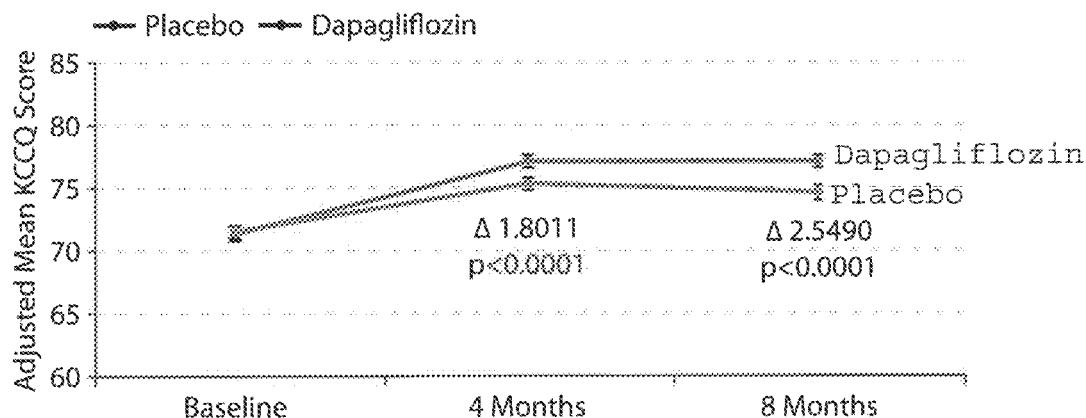
FIG. 7B KCCQ Clinical Summary Score
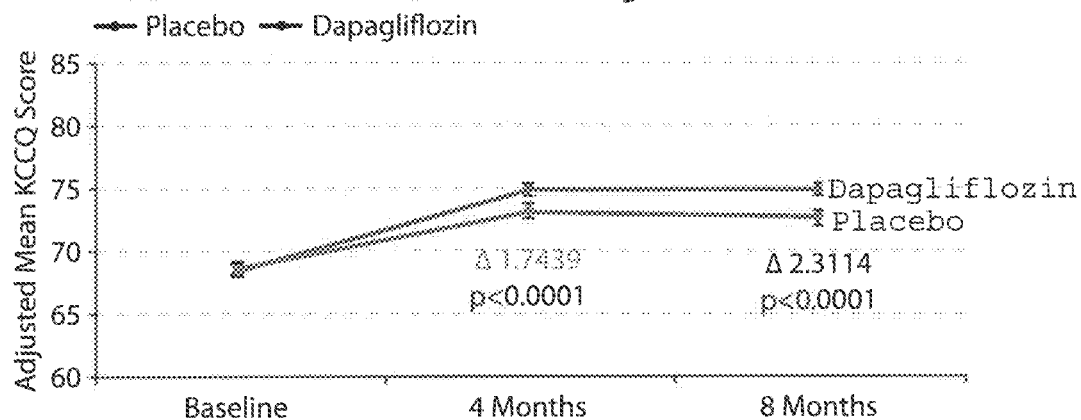
FIG. 7C KCCQ Overall Summary Score

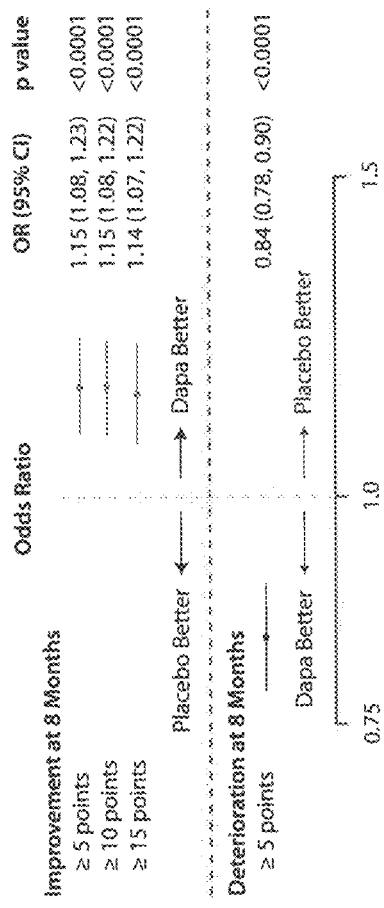
FIG. 8A KCCQ Total Symptom Score
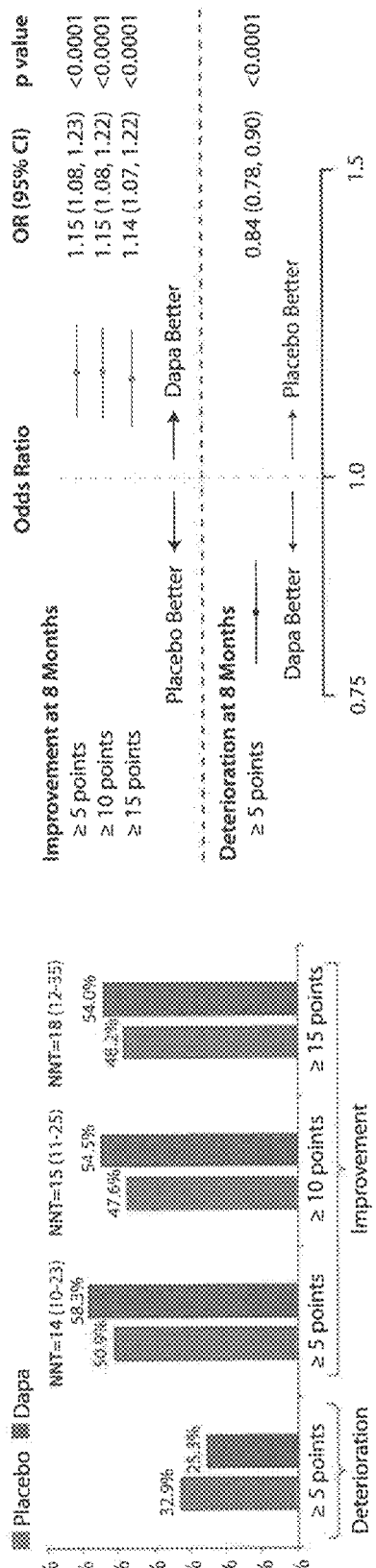
FIG. 8B KCCQ Total Symptom Score
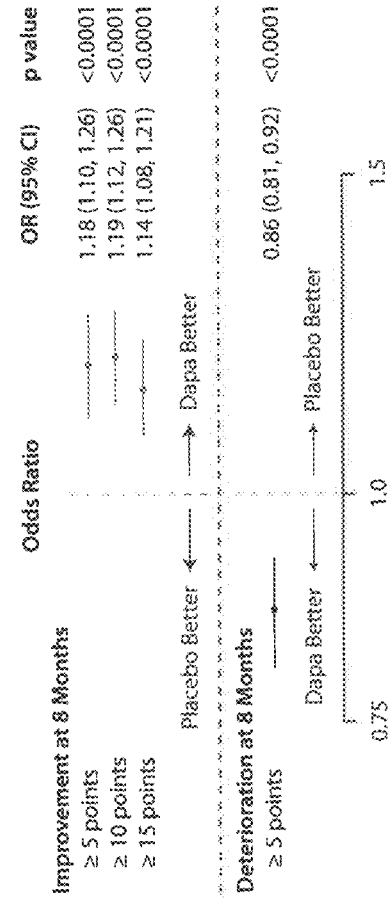
FIG. 8C KCCQ Clinical Summary Score
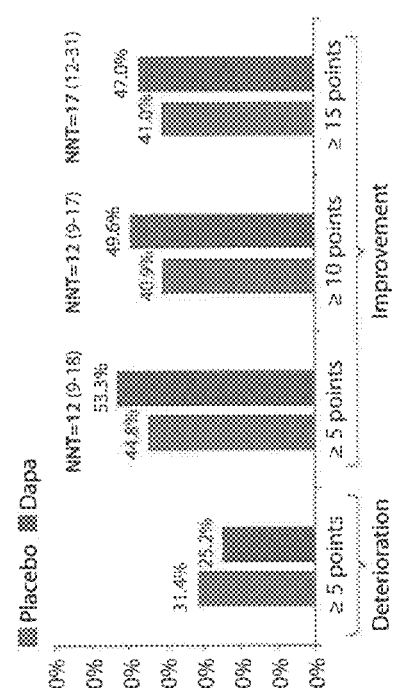
FIG. 8D KCCQ Clinical Summary Score

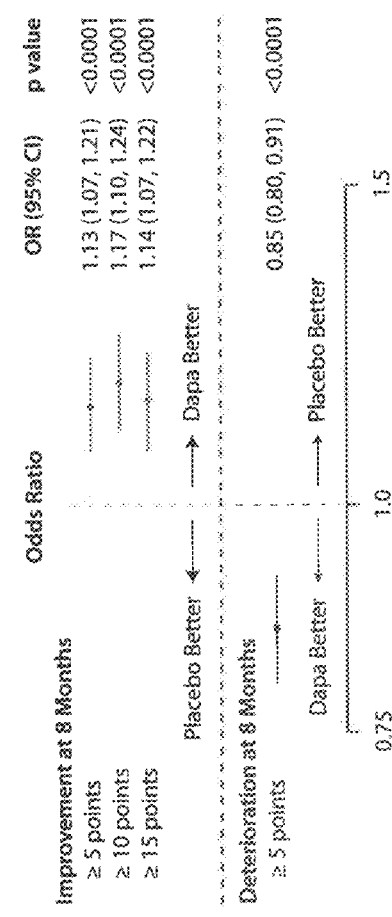
FIG. 8F KCCQ Overall Summary Score
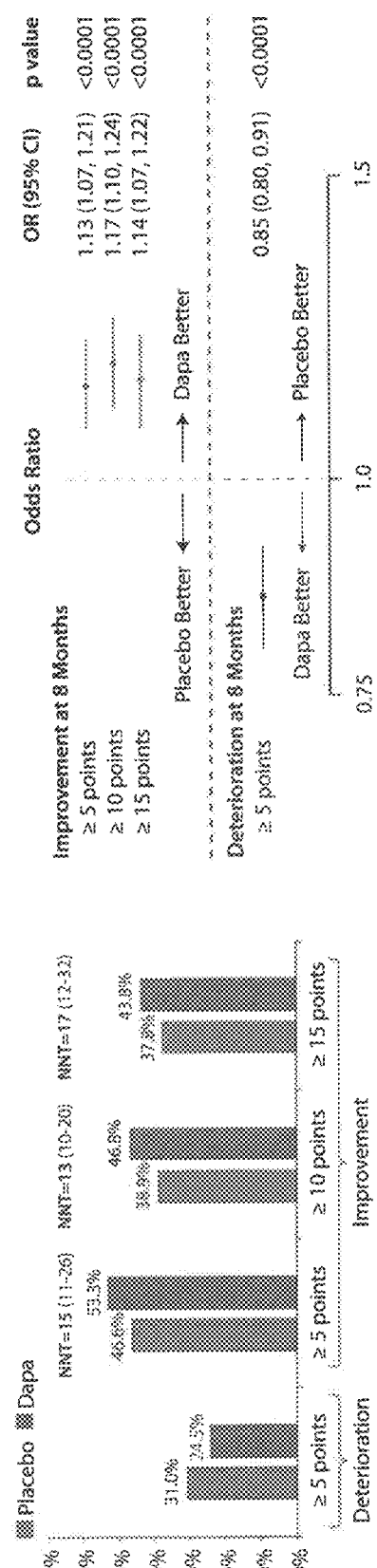
FIG. 8E KCCQ Overall Summary Score

METHODS OF TREATING HEART FAILURE WITH REDUCED EJECTION FRACTION

This application is a continuation of application Ser. No. 16/812,745, filed Mar. 9, 2020, now U.S. Pat. No. 10,973,836, issued Apr. 13, 2021, which claims the benefit of U.S. Provisional Application No. 62/985,407, filed Mar. 5, 2020, U.S. Provisional Application No. 62/969,181, filed Feb. 3, 2020, U.S. Provisional Application No. 62/960,756, filed Jan. 14, 2020, U.S. Provisional Application No. 62/946,625, filed Dec. 11, 2019, U.S. Provisional Application No. 62/930,673, filed Nov. 5, 2019, and U.S. Provisional Application No. 62/893,849, filed Aug. 30, 2019. The contents of these applications are each incorporated herein by reference in their entirety.

BACKGROUND

Heart failure (HF) is a life-threatening medical condition in which the heart cannot pump enough blood sufficiently to sustain the organs of the body. HF affects approximately 64 million people worldwide (half of whom have a reduced ejection fraction (HFrEF)) and the prevalence and incidence of HF continues to increase globally. (Cannie D. E. et al., *European Cardiology Review* 14(2):89-96 (2019)). HF is a chronic and degenerative disease where half of the patients will die within five years of diagnosis (Mamas, M. A. et al., *European Journal of Heart Failure* 19:1095-1104 (2017)). HF is the leading cause of hospitalization for those over the age of 65 and represents a significant clinical and economic burden (Azad, N. et al., *Journal of Geriatric Cardiology* 11:329-337 (2014)).

The current standard of care treatment paradigm for HF includes the simultaneous administration of one or more of the following classes of drugs, e.g., angiotensin-converting enzyme (ACE) inhibitors, angiotensin II-receptor blockers (ARBs), beta-blockers, mineralocorticoid receptor agents like mineralocorticoid-receptor antagonists (MRAs), angiotensin receptor-neprilysin inhibitors (ARNIs), digoxin, diuretics, heart pump medication, selective sinus node inhibitors, blood vessel dilators, and calcium channel blockers (unless the patient has systolic heart failure). Even with the best possible treatment, however, the five-year survival rate for HF is worse than for most cancers. (Braunwald, E. et al., *Lancet* 385:812-824 (2015)). Morbidity and mortality for patients with HF remain high, and patient outcomes need improvement. Additional methods of treating patients with HF, and especially HFrEF, are needed to reduce cardiovascular mortality, reduce heart failure events and the worsening of HF symptoms, and improve patient outcomes by slowing disease progression.

Sodium-glucose co-transporter type 2 (SGLT2) inhibitors are a class of glucose-lowering agents that improve glycemic control with a low risk of hypoglycemia, independent of insulin secretion, providing a reduction in blood pressure, body weight, and levels of uric acid (Inzucchi et al., *Diabetes & Vascular Dis Res.* 12(2):90-100 (2015)). SGLT2 inhibitors decrease renal glucose reabsorption, thereby increasing urinary glucose excretion (Id.). In addition, SGLT2 inhibitors decrease vascular stiffness and improve endothelial function.

Dapagliflozin is a potent, highly selective and orally active inhibitor of human renal SGLT2 which effectively lowers HbA1c with a low risk of inducing hypoglycemia. Dapagliflozin treatment has been shown to reduce weight, systolic blood pressure, blood uric acid, albuminuria, and improve arterial compliance-all conditions which are associated with increased CV risk (Shigiyama et al., *Cardiovasc Diabetol* 16:84 (2017)). The chemical structure of dapagliflozin is:

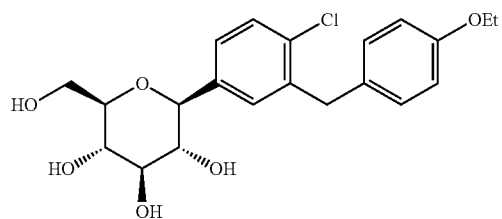 [SMILES: CCOc1ccc(Cc2cc([C@@H]3O[C@H](CO)[C@@H](O)[C@H](O)[C@H]3O)ccc2Cl)cc1]

Accordingly, the present disclosure is directed to methods of treating patients with HFrEF, including those with or without Type 2 diabetes (T2D), with an SGLT2 inhibitor, e.g., dapagliflozin.

SUMMARY OF THE DISCLOSURE

The present disclosure relates to a method of treating heart failure with reduced ejection fraction (HFrEF) in a patient, comprising administering to the patient an effective amount of a sodium-glucose cotransporter 2 (SGLT2) inhibitor. For instance, in some embodiments, the present disclosure includes methods of treating HFrEF in a patient without Type 2 diabetes (T2D), comprising administering to the patient an effective amount of a sodium-glucose cotransporter 2 (SGLT2) inhibitor. In other embodiments, the present disclosure includes methods of treating HFrEF in a patient with T2D, comprising administering to the patient an effective amount of a SGLT2 inhibitor.

Also disclosed are methods of preventing or delaying a fatal cardiovascular event in a patient with HFrEF and with or without T2D comprising administering to the patient an effective amount of a SGLT2 inhibitor.

Also disclosed herein are methods of preventing or delaying the incidence of diabetes in a patient with HFrEF and without T2D comprising administering to the patient an effective amount of a SGLT2 inhibitor. In some embodiments, the patient with HFrEF and without T2D has a glycated hemoglobin less than 5.7%. In some embodiments, the patient with HFrEF and without T2D is prediabetic (i.e., has a glycated hemoglobin $\geq 5.7\%$ and $<6.5\%$). In some embodiments, the methods disclosed herein reduce the incidence of T2D relative to placebo. In some embodiments, the methods disclosed herein reduce the incidence of T2D relative to a standard of care HF agent. In some embodiments, the reduction of the incidence of T2D is measured by time to first report of a glycated hemoglobin measurement of $\geq 6.5\%$. In some embodiments, the methods disclosed herein result in a hazard ratio of less than one for reducing the incidence of T2D relative to placebo. In some embodiments, the methods disclosed herein result in a hazard ratio of less than one for reducing the incidence of T2D relative to a standard of care HF agent.

Also disclosed are methods of treating HFrEF in a patient with or without T2D, comprising administering to the patient an effective amount of a SGLT2 inhibitor, wherein the patient experiences no adverse events related to renal dysfunction while under treatment. In some embodiments, no adverse advents related to renal dysfunction comprises no or minimal reduction in eGFR levels, no end-stage renal disease (ESRD), and/or no death from renal causes.

Disclosed herein are methods of reducing the total number of standard of care heart failure (HF) agents taken by a patient with HFrEF with or without T2D, comprising administering to the patient an effective amount of a SGLT2 inhibitor.

In any of the embodiments disclosed herein, the SGLT2 inhibitor is dapagliflozin, canagliflozin, empagliflozin, sotagliflozin, ipragliflozin, or ertugliflozin, or a pharmaceutically acceptable salt, solvate, mixed solvate, complex, or prodrug thereof. In at least one embodiment, the SGLT2 inhibitor is dapagliflozin, or a pharmaceutically acceptable salt, solvate, mixed solvate, complex, or prodrug thereof. In at least one embodiment, dapagliflozin is in the form of a non-crystalline solid. In at least one embodiment, dapagliflozin is in the form of a crystalline solid. In at least one embodiment, dapagliflozin is in the form of a (S)-propylene glycol ((S)-PG) solvate, which has the structure

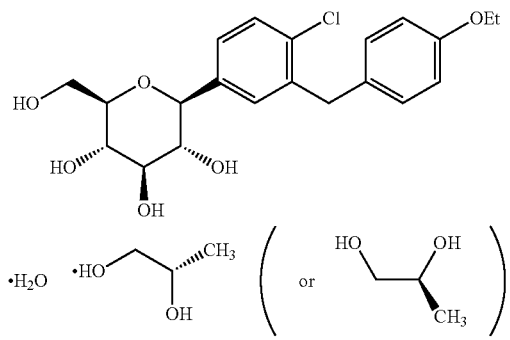

Further disclosed herein are methods comprising administering to a patient in need thereof an effective amount of a SGLT2 inhibitor alone or in combination with at least one other therapeutic agent. In some embodiments, the other therapeutic agent is administered with the SGLT2 inhibitor in the same or different pharmaceutical composition, and at the same or different time. In some embodiments, the other therapeutic agent is an antidiabetic agent, anti-obesity agent, anti-hyperlipidemic agent, anti-atherosclerotic agent, anti-hypertensive agent, anti-platelet agent, antithrombotic agent, or anticoagulant agent. For example, in at least one embodiment, the other therapeutic agent is an antidiabetic agent such as a biguanide and/or a DPP4 inhibitor. An exemplary biguanide is metformin or a pharmaceutically acceptable salt thereof. Exemplary DPP4 inhibitors include saxagliptin, linagliptin, sitagliptin, and pharmaceutically acceptable salts thereof.

In the disclosed methods herein, the patients have a left ventricular ejection fraction (LVEF) of less than or equal to 40%, such as less than or equal to 35%, 30%, or 25%, and in at least one embodiment, at least 20%. LVEF may be determined, for instance, by the use of an echocardiogram, radionuclide ventriculogram, contrast angiography, or cardiac MRI.

In some embodiments, the methods disclosed herein comprise administering to the patient orally an SGLT2 inhibitor, such as dapagliflozin or a pharmaceutically acceptable salt, solvate, mixed solvate, complex, or prodrug thereof, at a dose of 2.5 mg, 5.0 mg, or 10 mg, once a day. In at least one embodiment, the dose is 10 mg.

In some embodiments, the methods disclosed herein results in at least one of the following outcomes:
  (i) extends the length of time to a first heart failure (HF) event, and/or a fatal cardiovascular event; and/or
  (ii) reduces worsening of heart failure symptoms; and/or
  (iii) decreases the number of heart failure events and/or reduces the incidence of a fatal cardiovascular event.

In some embodiments, the methods disclosed herein reduce the incidence of myocardial infarction. In some embodiments, the myocardial infarction is fatal. In some embodiments, the myocardial infarction is non-fatal. In some embodiments, the patient has a history of myocardial infarction. In some embodiments, the patient does not have a history of myocardial infarction. In some embodiments, the methods disclosed herein reduce the incidence of myocardial infarction relative to placebo. In some embodiments, the methods disclosed herein reduce the incidence of myocardial infarction relative to a standard of care HF agent. In some embodiments, the reduction of the incidence of myocardial infarction is measured by time to first fatal or non-fatal myocardial infarction. In some embodiments, the methods disclosed herein result in a hazard ratio of less than one for reducing the incidence of myocardial infarction relative to placebo. In some embodiments, the methods disclosed herein result in a hazard ratio of less than one for reducing the incidence of myocardial infarction relative to a standard of care HF agent.

In some embodiments, the methods disclosed herein reduce the risk of hospitalization for heart failure and cardiovascular death in patients following an acute myocardial infarction. In some embodiments, the patient has experienced an acute myocardial infarction within 7 days from initiation of treatment with an SGLT2 inhibitor. In some embodiments, the patient has experienced a STEMI (ST segment elevation myocardial infarction). In some embodiments, the patient has experienced a NSTEMI (non-ST segment elevation myocardial infarction. In some embodiments, the SGLT2 inhibitor is dapagliflozin. In some embodiments, the patient has T2D. In some embodiments, the patient does not have T2D. In some embodiments, the patient has HFrEF. In some embodiments, the patient does not have HFrEF. In some embodiments, the methods disclosed herein reduce the risk of hospitalization for heart failure and cardiovascular death in patients following an acute myocardial infarction relative to placebo. In some embodiments, the methods disclosed herein reduce the risk of hospitalization for heart failure and cardiovascular death in patients following an acute myocardial infarction relative to a standard of care HF agent. In the methods disclosed herein, the patient being administered the SGLT2 inhibitor may be receiving one or more standard of care HF agents prior to or during administration of the SGLT2 inhibitor. In some embodiments, the methods disclosed herein result in at least one of the following outcomes in a patient who have experienced an acute myocardial infarction within 7 days:
  (i) extends the length of time to a first heart failure (HF) event, and/or a fatal cardiovascular event; and/or
  (ii) reduces worsening of heart failure symptoms; and/or
  (iii) decreases the number of heart failure events and/or reduces the incidence of a fatal cardiovascular event and/or
  (iv) reduces the risk of hospitalization for heart failure and cardiovascular death; and/or
  (v) reduces the risk of fatal or non-fatal myocardial infarction; and/or
  (vi) reduces the risk of major adverse cardiac events (composite of cardiovascular death, nonfatal myocardial infarction and nonfatal stroke); and/or
  (vii) reduces the risk of all-cause mortality.

In some embodiments, the methods described in the paragraph above result in a hazard ratio of less than one for any one of (i)-(vii). In some embodiments, the methods disclosed herein result in a hazard ratio of less than relative to a patient taking standard of care HF agent. In some embodiments, the methods disclosed herein result in a hazard ratio of less than relative to placebo.

In some embodiments, the methods disclosed herein reduce the time to first event of cardiovascular death or worsening heart failure symptoms in patients with acute decompensated heart failure. In some embodiments, the patient is hospitalized for worsening heart failure symptoms or acute decompensated heart failure prior to initiation of SGLT2 administration. In some embodiments, the patient has a left ventricular ejection fraction (LVEF) of less than or equal to 40%, such as less than or equal to 35%, 30%, or 25%, and in at least one embodiment, at least 20% prior to initiation of SGLT2 administration. In some embodiments, the SGLT2 inhibitor is dapagliflozin. In some embodiments, the patient has T2D prior to initiation of SGLT2 administration. In some embodiments, the patient does not have T2D prior to initiation of SGLT2 administration. In some embodiments, the patient has an eGFR >30 ml/min/1.73 m² prior to initiation of SGLT2 administration. In some embodiments, the patient has increased natriuretic peptides prior to initiation of SGLT2 administration. In some embodiments, the patient is hospitalized in stable condition for worsening heart failure symptoms or acute heart failure. As used herein, "stable condition" is understood to mean no increase in i.v. diuretics and no use of i.v. vasodilators or inotropes at least 24 hours prior to initiation of SGLT2 administration, such as at least 48 hours, for example, at least 72 hours, and in some embodiments, at least 1 week prior to initiation of SGLT2 administration. In some embodiments, the methods disclosed herein reduce the time to first event of cardiovascular death or worsening heart failure symptoms in patients with acute decompensated heart failure relative to placebo. In some embodiments, the methods disclosed herein reduce the time to first event of cardiovascular death or worsening heart failure symptoms in patients with acute decompensated heart failure relative to a standard of care HF agent. In the methods disclosed herein, the patient being administered the SGLT2 inhibitor may be receiving one or more standard of care HF agents prior to or during administration of the SGLT2 inhibitor.

In some embodiments, the methods disclosed herein result in at least one of the following outcomes in a patient with acute decompensated heart failure:
  (i) extends the length of time to a first fatal cardiovascular event; and/or
  (ii) extends the length of time to re-hospitalization for heart failure; and/or
  (iii) extends the length of time to an urgent HF medical visit; and/or
  (iv) extends the length of time of total number of days alive and out of the hospital; and/or
  (v) reduces worsening of heart failure symptoms; and/or
  (vi) reduces the risk of all-cause mortality.

In some embodiments, the methods described in the paragraph above result in a hazard ratio of less than one for any one of (i)-(vi). In some embodiments, the methods disclosed herein result in a hazard ratio of less than relative to a patient taking standard of care HF agent. In some embodiments, the methods disclosed herein result in a hazard ratio of less than relative to placebo.

In some embodiments, the methods disclosed herein reduce the incidence of any stroke (ischemic, hemorrhagic, or undetermined). In some embodiments, the stroke is fatal. In some embodiments, the stroke is non-fatal. In some embodiments, the patient has a history of stroke. In some embodiments, the patient does not have a history of stroke. In some embodiments, the methods disclosed herein reduce the incidence of stroke relative to placebo. In some embodiments, the methods disclosed herein reduce the incidence of stroke relative to a standard of care HF agent. In some embodiments, the reduction of the incidence of stroke is measured by time to first fatal or non-fatal stroke. In some embodiments, the methods disclosed herein result in a hazard ratio of less than one for reducing the incidence of stroke relative to placebo. In some embodiments, the methods disclosed herein result in a hazard ratio of less than one for reducing the incidence of stroke relative to a standard of care HF agent.

In some embodiments, administration of the SGLT2 inhibitor extends the length of time to a first heart failure (HF) event. In at least one embodiment, the HF event is a hospitalization for HF or an urgent HF medical visit. In at least one embodiment, the hospitalization for HF comprises a hospital admission lasting at least 24 hours with a primary diagnosis of HF. In some embodiments, the administration of the SGLT2 inhibitor reduces the total number of hospitalizations for HF. In at least one embodiment, the total number of hospitalizations for HF includes first and/or recurrent hospitalizations.

In some embodiments, the hospitalization for HF is due to one or more of the following criteria:
  (i) new or worsening symptoms of HF experienced by the patient; and/or
  (ii) objective evidence of new or worsening symptoms of HF; and/or
  (iii) initiation or intensification of treatment specifically for HF.

In at least one embodiment, new or worsening symptoms of HF experienced by the patient comprises dyspnea, decreased exercise tolerance, fatigue, and/or other symptoms of worsened end-organ perfusion or volume overload. In at least one embodiment, objective evidence of new or worsening symptoms of HF comprise physical examination findings considered to be due to HF and/or laboratory evidence of new or worsening HF. In at least one embodiment, the physical examination findings comprise at least two of the following findings: peripheral edema, increasing abdominal distention or ascites, pulmonary rales/crackles/ crepitations, increased jugular venous pressure and/or hepatojugular reflux, S3 gallop, and/or clinically significant or rapid weight gain related to fluid retention. In at least one embodiment, the laboratory evidence of new or worsening HF comprises at least one of the following findings: increased B-type natriuretic peptide (BNP)/N-terminal pro-BNP (NT-proBNP) concentrations consistent with decompensation of heart failure; radiological evidence of pulmonary congestion; non-invasive diagnostic evidence of clinically significant elevated left- or right-sided ventricular filling pressure or low cardiac output or invasive diagnostic evidence with right heart catheterization. In at least one embodiment, the initiation or intensification of treatment specifically for HF comprises at least one of the following: augmentation in oral diuretic therapy, intravenous administration of a diuretic or vasoactive agent, or mechanical or surgical intervention, for instance wherein mechanical or surgical intervention comprises mechanical circulatory support or mechanical fluid removal.

In some embodiments, an urgent HF medical visit is an emergency room visit for a primary diagnosis of HF, but does not require hospitalization, such as an urgent unscheduled visit to a physician's office for a primary diagnosis of HF. In some embodiments where an urgent HF medical visit is required, the patient experienced HF symptoms, and/or had physical examination findings and/or laboratory findings of new or worsening HF. In at least one embodiment, the patient experiences one or more symptoms of HF selected from the group consisting of dyspnea, decreased exercise tolerance, fatigue, and/or other symptoms of worsened end-organ perfusion or volume overload. In some embodiments where an urgent HF medical visit is required, the patient receives initiation or intensification of treatment specifically for HF. In some embodiments where an urgent HF medical visit is required, the patient requires intravenous therapy.

In some embodiments, administration of the SGLT2 inhibitor extends the length of time to a fatal cardiovascular event.

In the embodiments described above, the time to a first heart failure event and/or a fatal cardiovascular event may be delayed 8 weeks-24 months from the first administration of the SGLT2 inhibitor. In at least one embodiment, the time to a first heart failure event is delayed 8 weeks-24 months from the first administration of the SGLT2 inhibitor. In at least one embodiment, the time to a fatal cardiovascular event is delayed 8 weeks-24 months from the first administration of the SGLT2 inhibitor.

In some embodiments, administration of the SGLT2 inhibitor reduces the worsening of HF symptoms in the patient being treated. In at least one embodiment, the reduced worsening of heart failure symptoms in the patient is for a period of 12-36 months. In at least one embodiment, the reduced worsening of heart failure symptoms is characterized by the patient's reduced number of hospitalizations for HF. In at least one embodiment, the reduced worsening of heart failure symptoms is characterized by the patient's reduced number of urgent HF medical visits. In at least one embodiment, the urgent HF medical visit is an emergency room visit or an urgent outpatient medical office visit.

In at least one embodiment, the reduced worsening of heart failure symptoms is characterized by a patient's higher score on the Kansas City Cardiomyopathy Questionnaire Total Symptom Score (KCCQ-TSS) compared to the patient's score prior to SGLT2 inhibitor administration. In such embodiments, the higher score on the KCCQ-TSS occurs within 16 weeks from starting SGLT2 inhibitor administration. In other embodiments, the higher score on the KCCQ-TSS occurs within 20 weeks from starting SGLT2 inhibitor administration. In other embodiments, the higher score on the KCCQ-TSS occurs within 24 weeks from starting SGLT2 inhibitor administration. In other embodiments, the higher score on the KCCQ-TSS occurs within 28 weeks from starting SGLT2 inhibitor administration. In other embodiments, the higher score on the KCCQ-TSS occurs within 32 weeks or 8 months from starting SGLT2 inhibitor administration. In at least one embodiment, the higher score on the KCCQ-TSS is at least 5 points higher than the score prior to SGLT2 inhibitor administration. In at least one embodiment, the higher score on the KCCQ-TSS is at least 10 points higher than the score prior to SGLT2 inhibitor administration. In at least one embodiment, the higher score on the KCCQ-TSS is at least 15 points higher than the score prior to SGLT2 inhibitor administration.

In some embodiments, administration of the SGLT2 inhibitor results in any one or more of the following:
a) reduces heart failure symptoms;
b) reduces physical limitation;
c) improves exercise capacity; and/or
d) reduces the amount of time sedentary during daily life.

In at least one embodiment, the reduction in heart failure symptoms is characterized by a patient's higher score on the Kansas City Cardiomyopathy Questionnaire Total Symptom Score (KCCQ-TSS) compared to the patient's score prior to SGLT2 inhibitor administration. In such embodiments, the higher score on the KCCQ-TSS occurs within 16 weeks (or 4 months) from starting SGLT2 inhibitor administration. In other embodiments, the higher score on the KCCQ-TSS occurs within 20 weeks from starting SGLT2 inhibitor administration. In other embodiments, the higher score on the KCCQ-TSS occurs within 24 weeks from starting SGLT2 inhibitor administration. In other embodiments, the higher score on the KCCQ-TSS occurs within 28 weeks from starting SGLT2 inhibitor administration. In other embodiments, the higher score on the KCCQ-TSS occurs within 32 weeks or 8 months from starting SGLT2 inhibitor administration. In at least one embodiment, the higher score on the KCCQ-TSS is at least 5 points higher than the score prior to SGLT2 inhibitor administration. In at least one embodiment, the higher score on the KCCQ-TSS is at least 10 points higher than the score prior to SGLT2 inhibitor administration. In at least one embodiment, the higher score on the KCCQ-TSS is at least 15 points higher than the score prior to SGLT2 inhibitor administration. In at least one embodiment, the KCCQ-TSS is patient-reported, such as patient-reported in a doctor's office. In at least one embodiment, the patient has T2D. In some embodiments, the patient does not have T2D.

In at least one embodiment, the reduction in physical limitations is characterized by a patient's higher score on the Kansas City Cardiomyopathy Questionnaire Physical Limitation Score (KCCQ-PLS) compared to the patient's score prior to SGLT2 inhibitor administration. In such embodiments, the higher score on the KCCQ-PLS occurs within 16 weeks (or 4 months) from starting SGLT2 inhibitor administration. In other embodiments, the higher score on the KCCQ-PLS occurs within 20 weeks from starting SGLT2 inhibitor administration. In other embodiments, the higher score on the KCCQ-PLS occurs within 24 weeks from starting SGLT2 inhibitor administration. In other embodiments, the higher score on the KCCQ-PLS occurs within 28 weeks from starting SGLT2 inhibitor administration. In other embodiments, the higher score on the KCCQ-PLS occurs within 32 weeks or 8 months from starting SGLT2 inhibitor administration. In at least one embodiment, the higher score on the KCCQ-PLS is at least 1 point higher than the score prior to SGLT2 inhibitor administration. In at least one embodiment, the higher score on the KCCQ-PLS is at least 5 points higher than the score prior to SGLT2 inhibitor administration. In at least one embodiment, the higher score on the KCCQ-PLS is at least 10 points higher than the score prior to SGLT2 inhibitor administration. In at least one embodiment, the higher score on the KCCQ-PLS is at least 15 points higher than the score prior to SGLT2 inhibitor administration. In at least one embodiment, the KCCQ-PLS is patient-reported, such as patient-reported in a doctor's office. In at least one embodiment, the patient has T2D. In some embodiments, the patient does not have T2D.

In at least one embodiment, the improvement in exercise capacity is characterized by a patient's longer 6-minute walk distance (6MWD) compared to the patient's 6MWD prior to SGLT2 inhibitor administration. In such embodiments, the longer 6MWD distance occurs within 16 weeks from starting SGLT2 inhibitor administration. In other embodiments, the longer 6MWD distance occurs within 20 weeks from starting SGLT2 inhibitor administration. In other embodiments, the longer 6MWD distance occurs within 24 weeks from starting SGLT2 inhibitor administration. In other embodiments, the longer 6MWD distance occurs within 28 weeks from starting SGLT2 inhibitor administration. In other embodiments, the longer 6MWD distance occurs within 32 weeks or 8 months from starting SGLT2 inhibitor administration. In at least one embodiment, the improvement in 6-minute walk distance (6MWD) is measured by a distance greater than or equal to 30 meters. In at least one embodiment, the patient has T2D. In some embodiments, the patient does not have T2D.

In at least one embodiment, the reduction in the amount of time sedentary during daily life is characterized by a patient's increased total time spent in light to vigorous physical activity compared to the patient's time spent in light to vigorous physical activity prior to SGLT2 inhibitor administration. In such embodiments, the reduction in the amount of time sedentary during daily life is measured within 7 days following 16 weeks of SGLT2 inhibitor administration and compared to the patient's time spent in light to vigorous physical activity prior to SGLT2 inhibitor administration. In other embodiments, the reduction in the amount of time sedentary during daily life is measured within 7 days following 20 weeks of SGLT2 inhibitor administration and compared to the patient's time spent in light to vigorous physical activity prior to SGLT2 inhibitor administration. In other embodiments, the reduction in the amount of time sedentary during daily life is measured within 7 days following 24 weeks of SGLT2 inhibitor administration and compared to the patient's time spent in light to vigorous physical activity prior to SGLT2 inhibitor administration. In other embodiments, the reduction in the amount of time sedentary during daily life is measured within 7 days following 28 weeks of SGLT2 inhibitor administration and compared to the patient's time spent in light to vigorous physical activity prior to SGLT2 inhibitor administration. In other embodiments, the reduction in the amount of time sedentary during daily life is measured within 7 days following 32 weeks or 8 months of SGLT2 inhibitor administration. In such embodiments, the time spent sedentary during daily life is measured by a wearable activity monitor. In at least one embodiment, the patient has T2D. In some embodiments, the patient does not have T2D.

In some embodiments, administration of the SGLT2 inhibitor decreases the number of HF events and/or reduces the incidence of a fatal cardiovascular event. In at least one embodiment, administration of the SGLT2 inhibitor decreases the number of HF events. In at least one embodiment, the HF event is a hospitalization for HF or an urgent HF medical visit. In at least one embodiment, administration of the SGLT2 inhibitor decreases the number of hospitalizations for HF. In at least one embodiment, administration of the SGLT2 inhibitor decreases the number of urgent HF medical visits. In at least one embodiment, an urgent HF medical visit is an emergency room visit. In at least one embodiment, an urgent HF medical visit requires intravenous therapy.

In some embodiments, administration of the SGLT2 inhibitor decreases the composite of hospitalizations for HF or a fatal cardiovascular event.

In the methods disclosed herein, the patient being administered the SGLT2 inhibitor may be receiving one or more standard of care HF agents to treat HF prior to or during administration of the SGLT2 inhibitor. In at least one embodiment, the one or more standard of care HF agents are selected from the group consisting of angiotensin-converting enzyme (ACE) inhibitors, angiotensin II receptor blockers (ARB), beta blockers, mineralocorticoid receptor agents like mineralocorticoid-receptor antagonists (MRA), neprilysin inhibitors, antiplatelet agents, aspirin, lipid-lowering agents (e.g., statins, bile acid sequestrants, niacin, fibrates, omega3 fatty acid) and diuretics, such as a loop diuretic.

In the methods disclosed herein, the patient being administered the SGLT2 inhibitor may have a New York Heart Association (NYHA) heart failure classification of II to IV. In at least one embodiment, the patient being administered the SGLT2 inhibitor has a NYHA heart failure classification of II. In at least one embodiment, the patient being administered the SGLT2 inhibitor has a NYHA heart failure classification of III or IV.

In the methods disclosed herein, the patient being administered the SGLT2 inhibitor may have an eGFR of ≥30 ml/min/1.73 m2 prior to administration of the SGLT2 inhibitor. In the methods disclosed herein, the patient being administered the SGLT2 inhibitor has an eGFR of ≥30 ml/min/1.73 $m^2$ during administration of the SGLT2 inhibitor.

In the methods disclosed herein, the patient being administered the SGLT2 inhibitor may have a plasma N-terminal pro-B-type natriuretic peptide (NT-proBNP) level of at least 400 pg per milliliter, at least 600 pg per milliliter, or at least 900 pg per milliliter prior to SGLT2 inhibitor administration.

In the methods disclosed herein, the patient being administered the SGLT2 inhibitor may have been medically diagnosed with symptomatic HFrEF prior to SGLT2 inhibitor administration. In at least one embodiment, the patient may have been diagnosed with HFrEF at least two months prior to SGLT2 inhibitor administration.

In the methods disclosed herein, the patient being administered the SGLT2 inhibitor may have had atrial fibrillation and/or atrial flutter prior to SGLT2 inhibitor administration. In at least one embodiment, the patient being administered the SGLT2 inhibitor does not have an atrial fibrillation or atrial flutter prior to SGLT2 inhibitor administration. In at least one embodiment, the methods disclosed herein reduce the incidence of atrial fibrillation in patients that has a history of atrial fibrillation or atrial flutter prior to SGLT2 inhibitor administration. In at least one embodiment, the methods disclosed herein reduce the incidence of atrial fibrillation in patients that do not have an atrial fibrillation or atrial flutter prior to SGLT2 inhibitor administration. In some embodiments, the methods disclosed herein reduce the incidence of atrial fibrillation relative to placebo. In some embodiments, the methods disclosed herein reduce the incidence of atrial fibrillation relative to a standard of care HF agent. In some embodiments, the reduction of the incidence of atrial fibrillation is measured by time to first fatal or non-fatal atrial fibrillation. In some embodiments, the methods disclosed herein result in a hazard ratio of less than one for reducing the incidence of atrial fibrillation relative to placebo. In some embodiments, the methods disclosed herein result in a hazard ratio of less than one for reducing the incidence of atrial fibrillation relative to a standard of care HF agent.

In certain embodiments, the disclosed methods result in a decrease in HbA1c in the patient. In certain embodiments, the disclosed methods result in a decrease in systolic blood pressure in the patient. In certain embodiments, the disclosed methods result in a decrease in weight of the patient. In certain embodiments, the disclosed methods result in a decrease in NT-proBNP levels in the patient. In any of the above embodiments, the decrease may occur within 8 months from the start of SGLT2 inhibitor administration. In certain embodiments, the disclosed methods result in a 50% or greater sustained decline in eGFR per ml/min/1.73 $m^2$ over time in the patient. In such embodiments, the sustained decline may be 12 months, 18 months, 24 months, or more.

In certain embodiments, the methods disclosed herein result in an improvement in NYHA HF classification.

In certain embodiments, the methods disclosed herein result in a decrease in recurrent hospitalizations for HF or a decrease in recurrent HF events. In at least one embodiment, the recurrent HF events comprise a hospitalization for HF or an urgent HF medical visit.

In certain embodiments, the methods disclosed herein result in a lower incidence of deaths due to non-cardiovascular causes.

Further disclosed herein are methods for reducing the rate of a primary composite endpoint of cardiovascular death, HF hospitalization, or an urgent HF medical visit, in a patient with HFrEF being treated with a SGLT2 inhibitor and standard of care HF agents, wherein the rate is reduced relative to a patient being treated with standard of care HF agents alone. Further disclosed are methods for reducing the rate of a secondary composite endpoint of cardiovascular death or HF hospitalization, in a patient with HFrEF being treated with a SGLT2 inhibitor and standard of care HF medications, wherein the rate is reduced relative to a patient being treated with standard of care HF agents alone. In any of the above embodiments, the SGLT2 inhibitor may be, for example, dapagliflozin or a pharmaceutically acceptable salt, solvate, mixed solvate, complex, or prodrug thereof. In at least one embodiment, the SGLT2 inhibitor is dapagliflozin administered to a patient at 10 mg orally one per day.

In some embodiments, the methods disclosed herein results in at least one of the following outcomes:
(i) extends the length of time to a first heart failure (HF) event, and/or a fatal cardiovascular event; and/or
(ii) reduces worsening of heart failure symptoms; and/or
(iii) decreases the number of heart failure events and/or reduces the incidence of a fatal cardiovascular event.

Also disclosed herein are methods of reducing the risk of hyperkalemia in a patient with HF comprising administering to the patient an effective amount of an SGLT2 inhibitor. In some embodiments, the methods disclosed herein reduce the risk of hyperkalemia in a patient with HF comprising administering to the patient a pharmaceutical composition comprising an effective amount of an SGLT2 inhibitor. In some embodiments, disclosed is an SGLT2 inhibitor for use in reducing the risk of hyperkalemia in a patient with HF.

In some embodiments, the present disclosure relates to methods for reducing the risk of hyperkalemia associated with MRA use in a patient with HF, comprising administering to the patient an effective amount of an SGLT2 inhibitor. In some embodiments, the present disclosure relates to methods for reducing the risk of hyperkalemia associated with MRA use in a patient with HF, comprising administering to the patient a pharmaceutical composition comprising an effective amount of an SGLT2 inhibitor. In some embodiments, disclosed is an SGLT2 inhibitor for use in reducing the risk of hyperkalemia associated with MRA use in a patient with HF.

In some embodiments, the present disclosure relates to methods of treating HF in a patient, comprising administering to the patient an effective amount of an MRA and an effective amount of an SGLT2 inhibitor. In some embodiments, the present disclosure relates to methods of treating HF in a patient, comprising administering to the patient a pharmaceutical composition comprising an effective amount of an MRA and an effective amount of a SGLT2 inhibitor. In some embodiments, disclosed is an SGLT2 inhibitor in combination with an MRA for use in reducing the risk of hyperkalemia in a patient with HF. In some embodiments, disclosed is an SGLT2 inhibitor for use in the treatment of HF in a patient, wherein said treatment comprises the separate, sequential or simultaneous administration of an MRA and an SGLT2 inhibitor to said patient.

In some embodiments, the SGLT2 inhibitor is dapagliflozin. In some embodiments, the MRA is chosen from steroidal mineralocorticoid-receptor antagonists (MRA)s, for example, spironolactone (e.g., marketed as Aldactone®, Aldactazide®) and eplerenone (e.g., marketed as Inspra®). In some embodiments, the MRA is chosen from non-steroidal MRAs such as finerenone, esaxerenone, KBP-5074, and apararenone.

Also disclosed herein is AZD9977, 2-{(3S)-7-Fluoro-4-[(3-oxo-3,4-dihydro-2H-1,4-benzoxazin-6-yl)carbonyl]-3,4-dihydro-2H-1,4-benzoxazin-3-yl}-N-methylacetamide, disclosed in WO 2016/001631, and having the following structure:

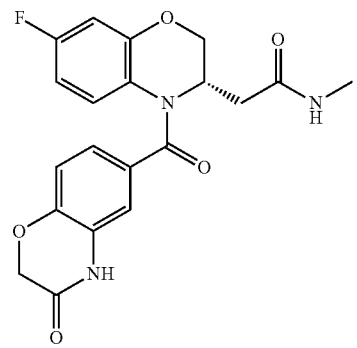 [SMILES: CNC(=O)C[C@H]1COc2cc(F)ccc2N1C(=O)c1ccc2c(c1)NC(=O)CO2]

In some embodiments, disclosed is a method of treating HF comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of HF in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of HF in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of reducing the risk of hyperkalemia in a patient with HF comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for reducing the risk of hyperkalemia in a patient with HF in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for reducing the risk of hyperkalemia in a patient with HF in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of treating HFrEF comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of HFrEF in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of HFrEF in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of treating HFpEF comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in the treatment of HFpEF in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in the treatment of HFpEF in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of reducing the risk of cardiovascular death and hospitalization for heart failure comprising administering to a patient in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in reducing the risk of cardiovascular death and hospitalization for heart failure in a patient, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in reducing the risk of cardiovascular death and hospitalization for heart failure in a patient, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of reducing the risk of cardiovascular death and hospitalization for heart failure comprising administering to a patient with an LVEF less than or equal to 55% and an eGFR ranging from about 15-45 ml/min/1.73 m2 in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in reducing the risk of cardiovascular death and hospitalization for heart failure in a patient with an LVEF less than or equal to 55% and an eGFR ranging from about 15-45 ml/min/1.73 m2, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in reducing the risk of cardiovascular death and hospitalization for heart failure in a patient with an LVEF less than or equal to 55% and an eGFR ranging from about 15-45 ml/min/1.73 m2, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In some embodiments, disclosed is a method of reducing the rate of a composite endpoint of cardiovascular death, hospitalization for heart failure, or urgent HF visit comprising administering to a patient with an LVEF less than or equal to 55% and an eGFR ranging from about 15-45 ml/min/1.73 m2 in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in reducing the rate of a composite endpoint of cardiovascular death, hospitalization for heart failure, or urgent HF visit in a patient with an LVEF less than or equal to 55% and an eGFR ranging from about 15-45 ml/min/1.73 m2, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in reducing the rate of a composite endpoint of cardiovascular death, hospitalization for heart failure, or urgent HF visit in a patient with an LVEF less than or equal to 55% and an eGFR ranging from about 15-45 ml/min/1.73 m2, wherein said treatment comprises the separate, sequential or simultaneous administration of an SGLT2 inhibitor and AZD9977 or a pharmaceutically acceptable salt thereof.

In some embodiments, the SGLT2 inhibitor is dapagliflozin or a pharmaceutically acceptable salt, solvate, mixed solvate, complex, or prodrug thereof.

In some embodiments, disclosed is a method of reducing the rate of any one of all-cause mortality, myocardial infarction, or stroke, comprising administering to a patient with an LVEF less than or equal to 55% and an eGFR ranging from about 15-45 ml/min/1.73 m2 in need thereof an effective amount of AZD9977 or a pharmaceutically acceptable salt thereof; and an effective amount of an SGLT2 inhibitor. In some embodiments, the SGLT2 inhibitor is dapagliflozin or a pharmaceutically acceptable salt, solvate, mixed solvate, complex, or prodrug thereof.

In some embodiments, disclosed is AZD9977 or a pharmaceutically acceptable salt thereof for use in reducing the rate of any one of all-cause mortality, myocardial infarction, or stroke in a patient with an LVEF less than or equal to 55% and an eGFR ranging from about 15-45 ml/min/1.73 m2, wherein said treatment comprises the separate, sequential or simultaneous administration of AZD9977 and an SGLT inhibitor to said patient. In some embodiments, the SGLT2 inhibitor is dapagliflozin or a pharmaceutically acceptable salt, solvate, mixed solvate, complex, or prodrug thereof.

In some embodiments, disclosed is an SGLT2 inhibitor for use in reducing the rate of any one of all-cause mortality, myocardial infarction, or stroke in a patient with an LVEF less than or equal to 55% and an eGFR ranging from about 15-45 ml/min/1.73 m2, wherein said treatment comprises the separate, sequential or simultaneous administration of an SGLT2 inhibitor and AZD9977 or a pharmaceutically acceptable salt thereof. In some embodiments, the SGLT2 inhibitor is dapagliflozin or a pharmaceutically acceptable salt, solvate, mixed solvate, complex, or prodrug thereof.

In any of the above embodiments, the SGLT2 inhibitor may be, for example, dapagliflozin or a pharmaceutically acceptable salt, solvate, mixed solvate, complex, or prodrug thereof. In at least one embodiment, the SGLT2 inhibitor is dapagliflozin or a pharmaceutically acceptable salt, solvate, mixed solvate, complex, or prodrug thereof administered at 10 mg orally once per day. In any of the embodiments above, AZD9977 or a pharmaceutically acceptable salt thereof is administered to a patient in an amount ranging from 100 mg-150 mg orally once per day In any of the above embodiments, the patient has a left ventricular ejection fraction (LVEF) of less than or equal to 40%, such as less than or equal to 35%, 30%, or 25%, and in at least one embodiment, at least 20%. In some embodiments, the patient has a left ventricular ejection fraction (LVEF) of less than or equal to 40%, such as less than or equal to 35%, 30%, or 25%, and in at least one embodiment, at least 20%. In some embodiments, the patient has an LVEF of greater than or equal to 40%, such as greater than or equal to 45%, 50%, or 55%, and in at least one embodiment, at least 55%. In some embodiments, the patient has an eGFR prior to administration of less than or equal to 45 ml/min/1.73 m2, such as less than or equal to 30 ml/min/1.73 m2, 25 ml/min/1.73 m2, 20 ml/min/1.73 m2, or 15 ml/min/1.73 m2. In some embodiments, the patient has T2D. In some embodiments, the patient does not have T2D. In some embodiments, hyperkalemia is understood to mean a potassium level of greater than 5.5 mmol/L. In some embodiments, hyperkalemia may be mild (serum potassium levels greater than 5.5 mmol/L) or moderate/severe (serum potassium levels greater than 6.0 mmol/L).

BRIEF DESCRIPTION OF THE DRAWINGS

FIG. 2A is a graph depicting the trial's primary endpoint of the composite of: death from cardiovascular causes, hospitalization for heart failure, or an urgent heart failure visit requiring intravenous therapy. The cumulative incidences of the primary endpoint (FIG. 2A), heart failure hospitalization (FIG. 2B), death from cardiovascular causes (FIG. 2C), as well as death from any cause (FIG. 2D), were estimated with the use of the Kaplan-Meier method and hazard ratios and 95% confidence intervals were estimated with the use of Cox regression models, stratified by diabetes status with history of heart failure hospitalization and treatment with dapagliflozin or placebo as explanatory variables. Analyses were based upon all participants who underwent randomization. The displays are truncated at the point where less than 10% of patients remained at risk. The inset in each panel shows the same data on an enlarged y axis.

FIGS. 7A-7C are graphs depicting KCCQ Total Symptom Score (TSS) (FIG. 7A); KCCQ Clinical Symptom Score (CSS) (FIG. 7B); and KCCQ Overall Summary Score (OSS) (FIG. 7C) following treatment with dapagliflozin vs. placebo in the DAPA-HF trial.

FIGS. 8A-8F are bar graphs (FIGS. 8A, 8C, and 8E) and corresponding Odds Ratios (OR) (FIGS. 8B, 8D, and 8F) comparing KCCQ Total Symptom Score (TSS), KCCQ Clinical Symptom Score (CSS), and KCCQ Overall Summary Score (OSS) following treatment with dapagliflozin vs. placebo in the DAPA-HF trial.

(FIG. 10B).

DETAILED DESCRIPTION OF THE DISCLOSURE

Figure 1:
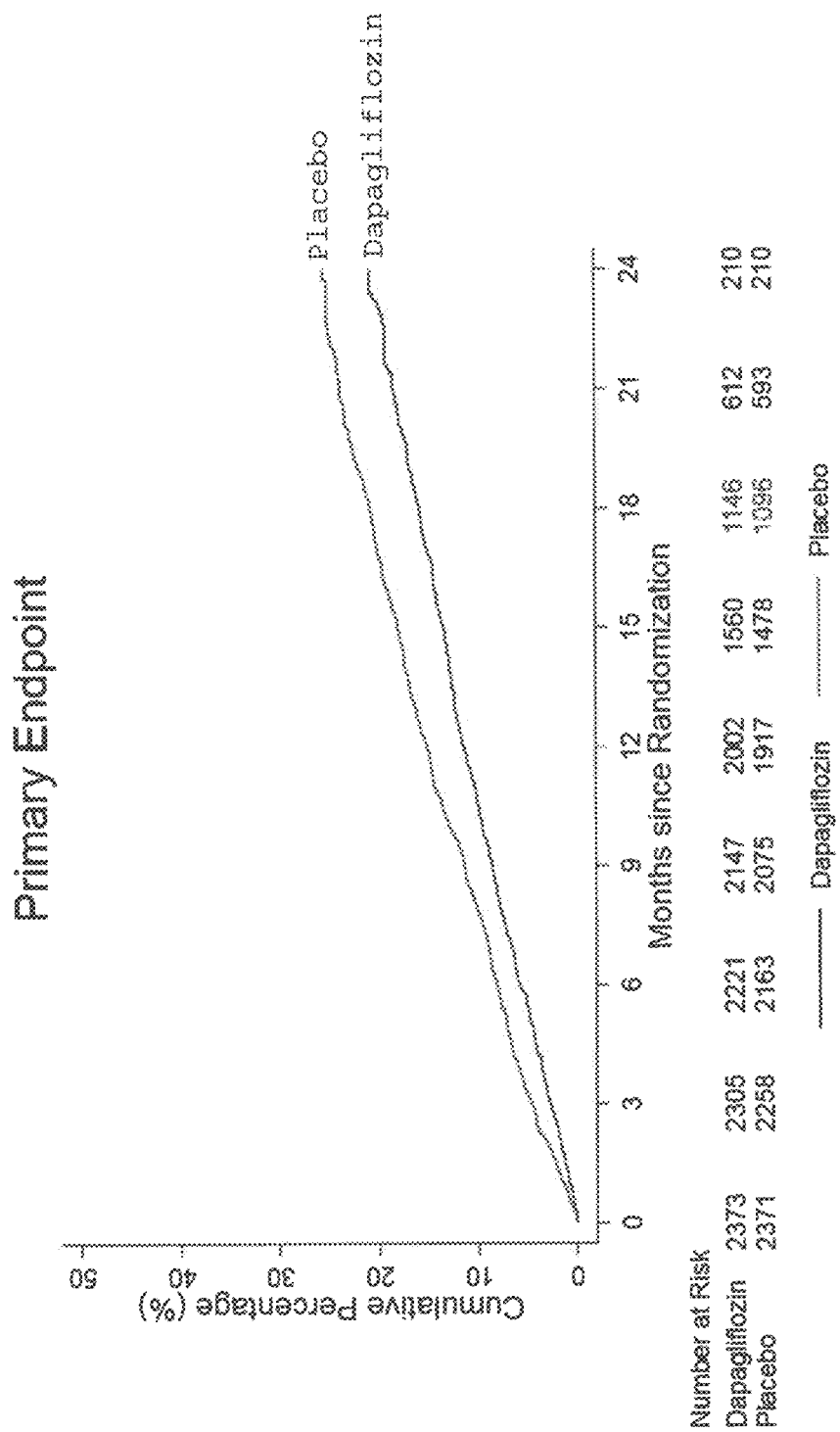
FIG. 1 is a flow chart depicting screening, randomization, and follow-up of patients in the Dapagliflozin and Prevention of Adverse Outcomes in Heart Failure (DAPA-HF) multi-center phase 3 clinical trial, described in Example 1. All randomized patients were the intent-to-treat (ITT) population.

The present disclosure is directed to methods of treating patients with heart failure with low ejection fraction (HFrEF), including those with or without Type 2 diabetes (T2D), with an SGLT2 inhibitor, e.g., dapagliflozin. The present disclosure is also directed to treating HFrEF patients with an SGLT2 inhibitor, e.g., dapagliflozin by extending the length of time to a first (or recurrent) HF event, reducing HF symptoms, reducing the worsening of HF symptoms and/or reducing the incidence of death from a cardiovascular (CV) event. The present disclosure is also directed to methods for reducing the rate of a primary composite endpoint of CV death, HF hospitalization, or an urgent HF medical visit, or a secondary composite endpoint of CV death or HF hospitalization in a patient with HFrEF being treated with a SGLT2 inhibitor and standard of care HF agents, wherein the rate is reduced relative to a patient being treated with standard of care HF agents alone.

In some embodiments, the SGLT2 inhibitor, e.g., dapagliflozin, is administered with standard of care HF agents (such as, e.g., a beta blocker) in the same or a different composition, at the same or different time.

In some embodiments, the SGLT2 inhibitor, e.g., dapagliflozin, is administered with at least one other therapeutic agent (such as, e.g., an antidiabetic agent) in the same or a different composition, at the same or different time.

I. Definitions

The terms "comprising," "having," "including," and "containing" are to be construed as open-ended terms (i.e., meaning "including, but not limited to,") unless otherwise noted.

The term "and/or" as used in a phrase such as "A and/or B" herein is intended to include the following embodiments: "A and B," "A or B," "A," and "B."

Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone). Thus, as a practical example, when referring to one or more urgent HF events (e.g., HF hospitalizations and/or ER visit) and/or death due to cardiovascular causes, that are assessed as an endpoint/outcome following SGLT2 administration, it is intended that the results encompass the composite of all specified events taken together, the composite of any combination of less than all events taken together, or each event taken alone.

As used herein, the term "prodrug" refers to, for example, esters and carbonates that may be converted, for example, under physiological conditions or by solvolysis, to the SGLT2 inhibitor. Thus, the term prodrug includes metabolic precursors of the SGLT2 inhibitor that are pharmaceutically acceptable. The term prodrug also includes covalently bonded carriers that release the SGLT2 inhibitor in vivo when such prodrug is administered to a patient. Nonlimiting examples of prodrugs include esters and carbonates formed by reacting one or more hydroxyls of the SGLT2 inhibitor with alkyl, alkoxy, or aryl substituted acylating agents employing procedures known to those skilled in the art to generate acetates, pivalates, methylcarbonates, benzoates and the like.

Various forms of prodrugs are known in the art. For examples of such prodrug derivatives, see: (1) Design of Prodrugs, edited by H. Bundgaard, (Elsevier, 1985) and Methods in Enzymology, Vol. 42, pp. 309-396, edited by K. Widder et al. (Academic Press, 1985); (2) A Textbook of Drug Design and Development, edited by Krogsgaard-Larsen and H. Bundgaard, Chapter 5 "Design and Application of Prodrugs," by H. Bundgaard pp. 113-191 (1991); (3) Bundgaard, H., Advanced Drug Delivery Reviews 8: 1-38 (1992); (4) Bundgaard, H. et al., *Journal of Pharmaceutical Sciences* 77: 285 (1988); and (5) Kakeya, N. et al., *Chem Pharm Bull* 32: 692 (1984).

As used herein, the terms "treatment," "treating," and the like, refer to measures (e.g., administration of a medicament(s) to a subject) that cure, slow down, lessen symptoms of, and/or halt progression of a diagnosed pathologic condition or disorder, such as, e.g., HFrEF. As used herein, patients or subjects being treated or in need of treatment with the SGLT2 inhibitor described herein include those with an established diagnosis of the disorder, e.g., HFrEF.

A "therapeutically effective amount" or "effective amount" refers to an amount effective, at dosages and for periods of time necessary, to achieve a desired therapeutic result (e.g., treatment of HFrEF).

Prophylactic or preventative measures refer to measures (e.g., administration of an SGLT2 inhibitor, as described herein, to a subject) that prevent and/or slow the development of a targeted pathologic condition or disorder. Thus, those in need of prophylactic or preventative measures include those prone to have the disorder and those in whom the disorder is to be prevented. A "prophylactically effective amount" refers to an amount effective, at dosages and for periods of time necessary, to achieve a desired prophylactic result (e.g., prevention or delay of a fatal cardiovascular event).

The terms "patient" and "subject" are used synonymously to refer to an adult human individual who has been diagnosed with HFrEF and is being treated with standard of care HF medication(s), as described herein, before initiating SGLT2 therapy. In some embodiments, the patient has been diagnosed with HFrEF for at least two months.

As used herein, the term "heart failure with reduced ejection fraction," "HFrEF," or "patient with HFrEF" refers to the chronic medical condition whereby a patient's left ventricular ejection fraction (LVEF) is ≤40% and the patient's heart failure symptoms fall within Stages II-IV of the New York Heart Association (NYHA) heart failure classification system. See, Dolgin M, "Criteria Committee of the New York Heart Association; Nomenclature and Criteria for Diagnosis of Diseases of the Heart and Great Vessels," $9^{th}$ ed., Boston, Mass.: Little Brown & Co (1994). The NYHA heart failure classification system was employed during the enrollment of patients in the phase 3 clinical trial described in Example 1. In some embodiments, "patients with HFrEF" fall within Stage II of the NYHA HF classification. In some embodiments, "patients with HFrEF" fall within Stages III or IV of the NYHA HF classification.

While in some embodiments, the patient with HFrEF has a left ventricular ejection fraction (LVEF) of less than or equal to 40%, in some embodiments, LVEF is less than or equal to 35%, 30%, or 25%. In some embodiments, the LVEF is at least 20%. Diagnosis and evaluation of patients with HFrEF generally includes imaging of the heart and physical examination, such as evaluating LVEF using an echocardiogram, radionuclide ventriculogram, contrast angiography, or cardiac MRI.

The NYHA HF classification system categorizes classes I through IV according to subjective patient symptom assessment and classifies heart failure based on a patient's ability to function in daily life: Class I: No limitation of physical activity. Ordinary physical activity does not cause undue fatigue, palpitation, or dyspnea; Class II. Slight limitation of physical activity. Comfortable at rest. Ordinary physical activity results in fatigue, palpitation, and dyspnea; Class III. Marked limitation of physical activity. Comfortable at rest. Less than ordinary activity causes fatigue, palpitation, or dyspnea. Class IV. Unable to carry on any physical activity without discomfort. Symptoms of heart failure at rest. If any physical activity is undertaken, discomfort increases. Patients in Stages II-IV of the NYHA classification were enrolled in the Phase III DAPA-HF trial described in Example 1.

As used herein, "standard of care HF agents" include at least one standard of care HF agent, for example, at least two or at least three or more medications or medication classes, other than SGLT2 inhibitors, that are used to treat HF, for instance, HFrEF. The standard of care HF agents, as described herein, may be used prior to and/or during administration of the SGLT2 inhibitor, e.g., dapagliflozin. Standard of care HF medications and their dosages are well-known to cardiologists and other medical practitioners who examine and treat patients with HFrEF. Exemplary standard of care HF agents include: Angiotensin-converting enzyme (ACE) inhibitors; Angiotensin receptor blockers (ARBs); beta blockers; mineralocorticoid receptor agents like mineralocorticoid receptor antagonists (MRA), and neprilysin inhibitors.

Other medications that may be used to treat HFrEF, and thus can also be considered "standard of care HF agents," include diuretics, and loop diuretics (e.g., furosemide, bumetanide, and torsemide), digoxin, heart pump medication, selective sinus node inhibitors, ivabradine (a sino-atrial (SA) node modulator), aldosterone antagonists, blood vessel dilators, calcium channel blockers (unless the patient has systolic heart failure), hydralazine/isosorbide dinitrate, or other HF medications within practice guidelines. See Yancy C. W. et al., "ACC/AHA/HFSA focused update of the 2013 ACCF/AHA guideline for the management of heart failure: A report of the American College of Cardiology/American Heart Association task force on clinical practice guidelines and the Heart Failure Society of America, *J Am Coll Cardiol*. 70(6):776-803 (2017).

The terms "administer," "administering," "administration," and the like, as used herein, refer to methods that may be used to enable delivery of a drug, e.g., a SGLT2 inhibitor, as described herein. Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa. In at least one embodiment, the SGLT2 inhibitor is administered orally.

Administration of the SGLT2 inhibitor "in combination with one or more other therapeutic agents" includes simultaneous (concurrent) or consecutive administration, at the same or different time, and in the same or different pharmaceutical composition (e.g., pill, tablet, capsule). "Other therapeutic agents" include the standard of care HF medications, discussed above, or any of the following other therapeutic agents, such as an antidiabetic agent, anti-obesity agent, anti-hyperlipidemic agent, anti-atherosclerotic agent, anti-hypertensive agent, anti-platelet agent, anti-thrombotic agent, or anticoagulant agent. The "other therapeutic agent" may be in the form of a pharmaceutically acceptable salt, solvate, mixed solvate, complex, or prodrug.

In some instances, the other therapeutic agent is an antidiabetic agent such as a biguanide (e.g., metformin) and/or a DPP4 inhibitor (e.g., saxagliptin, linagliptin, or sitagliptin). Representative examples of combination SGLT2 inhibitor+antidiabetic agent products include: dapagliflozin/metformin extended release (XIGDUO XR®), dapagliflozin/saxagliptin (QTERN®), dapagliflozin/saxagliptin/metformin (QTERNMET®), canagliflozin/metformin (INVOKAMET®), canagliflozin/metformin extended release (INVOKAMET XR®), empagliflozin/linagliptin (GLYXAMBI®), empagliflozin/metformin (SYNJARDY®), empagliflozin/metformin extended release (SYNJARDY XR®), ertugliflozin/metformin (STEGLUROMET®), and ertugliflozin/sitagliptin (STEGLUJAN®).

As used herein, a "heart failure event" refers to a hospitalization for HF and/or an urgent HF medical visit.

As used herein, a "hospitalization for HF" or an "HF hospitalization" refers to an admission to a hospital for at least 24 hours with a primary diagnosis of HF. In some embodiments, the hospitalized patient exhibits new or worsening symptoms due to HF on presentation. In some embodiments, the hospitalized patient has objective evidence of new or worsening HF. In some embodiments, the hospitalized patient receives initiation or intensification of treatment specifically for HF. In some embodiments, the hospitalized patient has all of the foregoing criterion.

As used herein, "symptoms due to HF" include at least one symptom of dyspnea, decreased exercise tolerance, fatigue, or other symptoms of end-organ perfusion or volume overload. In some embodiments, the symptoms due to HF are new or worsened from a prior period of time, medical or hospital visit.

As used herein, the "Kansas City Cardiomyopathy Questionnaire (KCCQ)" refers to a questionnaire used by medical practitioners to assess a patient's HF symptoms and/or to determine whether a patient's HF symptoms are improving or worsening. The KCCQ uses a scale from 0 to 100, with a higher score indicating fewer HF symptoms and a 5 or greater point change considered clinically meaningful. See Green, C. P., "Development and evaluation of the Kansas City Cardiomyopathy Questionnaire: a new health status measure for heart failure," *J Am Coll Cardiol.* 35: 1245-1255 (2000). The KCCQ was administered in the DAPA-HF clinical trial (Example 1) as an indicator of health-related quality of life (HRQL). The analysis presented in Example 2 demonstrates that dapagliflozin reduced cardiovascular death and worsening HF across the range of baseline KCCQ values, and improved symptom burden, physical function, and quality of life in patients with HFrEF.

As used herein, "objective evidence of new or worsening HF" refers to physical examination findings by a medical practitioner considered to be due to HF and/or laboratory evidence of new or worsening HF. In some embodiments, the objective evidence of new or worsening HF consists of at least two physical examination findings. In some embodiments, the objective evidence of new or worsening HF consists of one physical examination finding and at least one laboratory evidence.

As used herein, "physical examination findings considered to be due to HF" (including new or worsened HF), refers to at least one finding of: peripheral edema; increasing abdominal distention or ascites; pulmonary rales/crackles/crepitations; increased jugular venous pressure and/or hepatojugular reflux; S3 gallop; and/or clinically significant or rapid weight gain thought to be related to fluid retention.

As used herein, "laboratory evidence of new or worsening HF" refers to at least one finding of: increased B-type natriuretic peptide (BNP)/N-terminal pro-BNP (NT-proBNP) concentrations consistent with decompensation of heart failure (such as BNP >500 pg/mL or NT-proBNP >2,000 pg/mL); radiological evidence of pulmonary congestion; non-invasive diagnostic evidence of clinically significant elevated left- or right-sided ventricular filling pressure or low cardiac output or invasive diagnostic evidence with right heart catheterization showing a pulmonary capillary wedge pressure (pulmonary artery occlusion pressure) ≥18 mmHg, central venous pressure ≥12 mmHg, or a cardiac index <2.2 L/min/m².

As used herein, "initiation or intensification of treatment specifically for HF," refers to at least one of the following: augmentation in oral diuretic therapy; intravenous diuretic or vasoactive agent (e.g., inotrope, vasopressor, or vasodilator); mechanical or surgical intervention (e.g., mechanical circulatory support, such as, e.g., intra-aortic balloon pump, ventricular assist device, extracorporeal membrane oxygenation, total artificial heart) and/or mechanical fluid removal (e.g., ultrafiltration, hemofiltration, dialysis).

As used herein, an "urgent HF medical visit" refers to an urgent, unscheduled medical office visit or an emergency department/emergency room visit for a primary diagnosis of HF, but the visit does not meet the criteria for a HF hospitalization. In some embodiments, the patient at the urgent HF medical visit will have HF symptoms and/or physical examination findings and/or laboratory evidence of new or worsening HF, as described above, and/or receives initiation or intensification of treatment specifically for HF, as described above.

As used herein, "cardiovascular (CV) death" refers to death of the patient undergoing treatment for HFrEF, as described herein, due to the following: acute myocardial infarction (MI), sudden cardiac death, heart failure or cardiogenic shock, stroke (cerebrovascular event), cardiovascular procedures, cardiovascular hemorrhage, other cardiovascular causes (refers to a CV death not included in the above categories but with a specific, known cause (e.g., pulmonary embolism or peripheral arteria disease).

As used herein, "non-cardiovascular (CV) death" refers to any death not covered by "cardiovascular (CV) death."

As used herein, the term "primary composite outcome" or "primary composite endpoint" refers to the composite of the following HF events (as defined above) occurring in HFrEF patients administered the SGLT2 inhibitor (e.g., dapagliflozin) along with standard of care HF agents:

Cardiovascular (CV) death;
HF hospitalization; or
Urgent HF medical visit (defined above to include ER visit(s) and urgent, unscheduled medical office visits)

and the determination of relative risk reduction in patients taking the SGLT2 inhibitor (e.g., dapagliflozin) compared to patients taking standard of care HF agents alone. (See Example 1).

As used herein, the term "secondary outcome" refers to the composite of the following HF events: CV death or HF hospitalization (as defined above) and the determination of relative risk reduction in patients taking the SGLT2 inhibitor (e.g., dapagliflozin) compared to patients taking standard of care HF agents alone. (See Example 1).

The use of comparative phrases, such as "reduction," "was reduced," "worsened," "was decreased," "worsening," "extension," "was extended," in relation to, e.g., HF symptoms, HF events, HF hospitalizations, CV deaths, or non-CV deaths, as described herein, is intended to indicate a comparison of the patient with HFrEF administered the SGLT2 inhibitor (e.g., dapagliflozin) relative to any of the following:
- a patient (or population of patients) not taking a SGLT2 inhibitor;
- a patient (or population of patients) taking standard of care HF agents only;
- a patient (or population of patients) taking a placebo over the same time period;
- a patient (or population of patients) taking a placebo and standard of care HF agents over the same time period;
- the patient prior to administration of the SGLT2 inhibitor;
- the average prognostic expectation for a population of patients with HFrEF.

II. SGLT2 Inhibitors

As provided herein, SGLT2 inhibitors can be used in the methods described herein to treat established HFrEF in patients with and without Type 2 diabetes.

Sodium-glucose cotransporter 2 (SGLT2) is a sodium-dependent renal protein that is responsible for reabsorbing glucose back into the blood. SGLT2 inhibitors (also known as "Gliflozins") are a class of medicine used to lower blood glucose in patients with type 2 diabetes by inhibiting renal SGLT2 proteins. As a result, more glucose is excreted in the urine.

SGLT2 inhibitors that may be used in the disclosed methods of treating patients with HFrEF include dapagliflozin (FARXIGA®), canagliflozin (INVOKANA®), empagliflozin (JARDIANCE®), ertugliflozin (STEGLATRO®), sotagliflozin, or ipragliflozin, or a pharmaceutically acceptable salt, solvate, mixed solvate, complex, or prodrug.

In a at least one embodiment, the SGLT2 inhibitor used in the disclosed methods of treating patients with HFrEF is dapagliflozin such as described in U.S. Pat. Nos. 6,414,126 and 6,515,117, which are incorporated by reference in their entireties. FARXIGA® was approved by the U.S. FDA in 2014 as a monotherapy and later in 2017-2019 as part of combination therapy (XIGDUO®, QTERN®, QTERNMET®) with diet and exercise to improve glycemic control in adults with type 2 diabetes. Dapagliflozin may be administered in doses of 2.5 mg, 5.0 mg, or 10 mg. In at least one embodiment, a dosage of 10 mg is administered for use in the disclosed methods.

In some embodiments, "dapagliflozin" refers to the FDA approved formulation, FARXIGA®, or it can refer to a pharmaceutically acceptable salt, solvate, mixed solvate, complex, or prodrug. In some embodiments, dapagliflozin is in the form of a (S)-propylene glycol ((S)-PG) solvate, which has the structure:

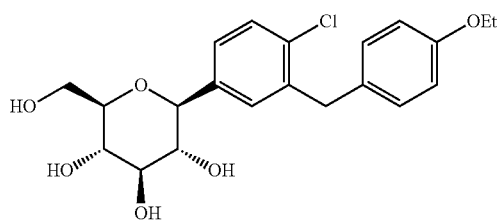

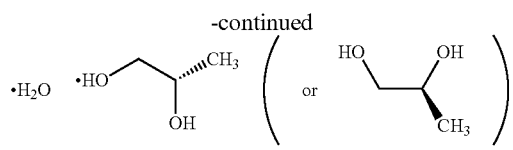

In some embodiments, dapagliflozin is in the form of a crystalline solid or non-crystalline solid.

In some embodiments, "dapaglifozin" is formulated as a fixed-dose combination product with another therapeutic agent, such as, e.g., another antidiabetes drug. Dapagliflozin/metformin extended release (XIGDUO®) and dapagliflozin/saxagliptin (QTERN®) and dapagliflozin/saxagliptin/metformin (QTERNMET®) are examples of combination products comprising dapagliflozin.

III. Standard of Care HF Agents

As used herein, "standard of care HF agents" include at least one, such as least two, at least three or more medications or medication classes, other than SGLT2 inhibitors, that are used to treat HF, such as HFrEF. The standard of care HF agents, as described herein, may be used prior to and/or during administration of the SGLT2 inhibitor, e.g., dapagliflozin. In some embodiments, the standard of care HF agents and the SGLT2 inhibitor are administered together, at the same or different times.

Exemplary standard of care HF agents include: angiotensin-converting enzyme (ACE) inhibitors; angiotensin receptor blockers (ARBs); beta blockers; mineralocorticoid receptor agents like mineralocorticoid receptor antagonists (MRAs), and neprilysin inhibitors. Standard of care HF agents and their dosages are well-known to cardiologists and other medical practitioners who examine and treat patients with HFrEF. A brief description of these standard of care HF agents follows:

ACE inhibitors cause vasodilation in both the venous and arterial systems, so they decrease both preload and afterload, increasing blood flow to vital organ systems and improving ejection fraction. These medications also block the enzyme needed to convert angiotensin I to angiotensin II. Angiotensin II is a strong vasoconstrictor that raises blood pressure, releases aldosterone, and leads to sodium and water retention. ACE inhibitors prevent this cascade of effects. Representative examples of ACE inhibitors include captopril, enalapril, and lisinopril.

ARBS, like ACE inhibitors, block the action of angiotensin II. ARBs block angiotensin II receptors in the blood vessels and the adrenal glands. In the blood vessels, ARBs cause venous and arterial dilation to reduce both preload and afterload. Blocking angiotensin II receptors in the adrenal glands decreases the release of aldosterone, which in turn increases the excretion of sodium and water. Representative examples of ARBs include valsartan, losartan, and irbesartan Beta blockers decrease sympathetic nervous system stimulation, lowering heart rate and blood pressure and improving left ventricular function, hemodynamics, and exercise tolerance. Representative examples of beta blockers include atenolol, propranolol, bisoprolol, carvedilol, and sustained-release metoprolol.

Mineralocorticoid receptor antagonist (MRA) or "aldosterone antagonists" are diuretic drugs, which antagonize the action of aldosterone at mineralocorticoid receptors. This group of drugs is often used as adjunctive therapy, in combination with other drugs, for the management of chronic heart failure. Representative examples of MRAs include spironolactone and eplerenone.

Mineralocorticoid receptor modulator (MRM) is used to describe a compound that exhibit tissue or cell specific receptor antagonism, either full antagonism, or partial antagonism.

Neprilysin Inhibitors break down natriuretic peptides, which are responsible for sodium and water loss when heart ventricles are overloaded. Delaying their breakdown lengthens their effects and removes more sodium and water from the body, decreasing intravascular volume and blood pressure, resulting in decreased preload and afterload. A representative example of a neprilysin inhibitor is Sacubitril. Neprilysin inhibitors may be also combined with ARBs in a new class of heart failure medications called angiotensin receptor neprilysin inhibitors. A first in class medication, Sacubitril/Valsartan, combines an ARB (Valsartan) with a neprilysin enzyme inhibitor (Sacubitril).

Other medications that may be used to treat HFrEF, and thus may also be considered "standard of care HF agents," include diuretics, and loop diuretics such as (e.g., furosemide, bumetanide, and torsemide), digitalis or other heart pumping medications, hydralazine/isosorbide dinitrate, ivabradine (a sino-atrial (SA) node modulator), or other HF medications within practice guidelines. See Yancy C. W. et al., "ACC/AHA/HFSA focused update of the 2013 ACCF/AHA guideline for the management of heart failure: A report of the American College of Cardiology/American Heart Association task force on clinical practice guidelines and the Heart Failure Society of America, *J Am Coll Cardiol.* 70(6):776-803 (2017).

IV. Other Therapeutic Agents

Administration of the SGLT2 inhibitor, as described herein, may also be in combination with one or more "other therapeutic agents." As used herein, the phrase "other therapeutic agents" typically does not include the standard of care HF agents, discussed above, unless the context indicates otherwise.

Other therapeutic agents that can be administered with the SGLT2 inhibitor, described herein, include antidiabetic agents, anti-obesity agents, anti-hyperlipidemic agents, anti-atherosclerotic agents, anti-hypertensive agents, anti-platelet agents, antithrombotic agents, or anticoagulant agents. The "other therapeutic agent" may be in the form of a pharmaceutically acceptable salt, solvate, mixed solvate, complex, or prodrug.

Administration of the SGLT2 inhibitor in combination with one or more "other therapeutic agents." includes simultaneous (concurrent) or consecutive administration, at the same or different time, and in the same or different pharmaceutical composition (e.g., pill, tablet, capsule).

In some instances, the other therapeutic agent is an antidiabetic agent such as a biguanide (e.g., metformin) and/or a DPP4 inhibitor (e.g., saxagliptin, linagliptin, or sitagliptin). Representative examples of combination SGLT2 inhibitor+antidiabetic agent products include: dapagliflozin/metformin extended release (XIGDUO®), dapagliflozin/saxagliptin (QTERN®), dapagliflozin/saxagliptin/metformin (QTERNMET®), canagliflozin/metformin (INVOKAMET®), canagliflozin/metformin extended release (INVOKAMET XR®), empagliflozin/linagliptin (GLYXAMBI®), empagliflozin/metformin (SYNJARDY®), empagliflozin/metformin extended release (SYNJARDY XR®), ertugliflozin/metformin (STEGLUROMET®), and ertugliflozin/sitagliptin (STEGLUJAN®).

V. Methods of Treating HFrEF by Administering an SGLT2 Inhibitor

The present disclosure provides a method of treating HFrEF in a patient, comprising administering to the patient an effective amount of a sodium-glucose cotransporter 2 (SGLT2) inhibitor, as described herein. In some embodiments, the patient also has Type 2 diabetes. In some embodiments, the patient does not have Type 2 diabetes.

The present disclosure also provides a method of treating HFrEF in a patient without T2D, comprising administering to the patient an effective amount of a SGLT2 inhibitor, wherein the patient experiences no adverse events related to renal dysfunction while under treatment.

The present disclosure also provides a method of treating HFrEF in a patient with T2D, comprising administering to the patient an effective amount of a SGLT2 inhibitor, wherein the patient experiences no adverse events related to renal dysfunction while under treatment.

In some embodiments, "no adverse events related to renal dysfunction" comprises no or minimal reduction in a patient's Estimated Glomerular Filtration Rate (eGFR) levels, no end-stage renal disease (ESRD), and/or no death from renal causes while undergoing SGLT2 inhibitor therapy.

In some embodiments, the SGLT2 inhibitor is dapagliflozin, canagliflozin, empagliflozin, sotagliflozin, ipragliflozin, or ertugliflozin, or a pharmaceutically acceptable salt, solvate, mixed solvate, complex, or prodrug.

In at least one embodiment, the SGLT2 inhibitor is dapagliflozin, or a pharmaceutically acceptable salt, solvate, mixed solvate, complex, or prodrug. In some embodiments, dapagliflozin is in the form of a non-crystalline solid. In some embodiments, dapagliflozin is in the form of a crystalline solid. In some embodiments, dapagliflozin is in the form of a (S)-propylene glycol ((S)-PG) solvate, which has the structure:

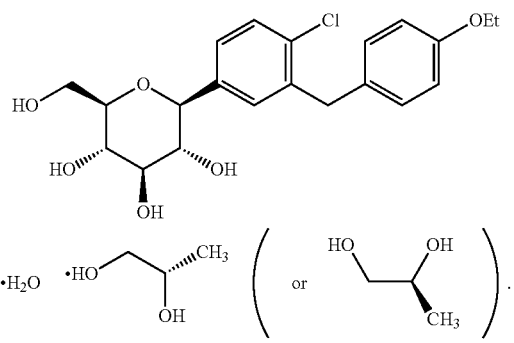

In some embodiments, the SGLT2 inhibitor (e.g., dapagliflozin) is administered orally to the patient, one time a day. In some embodiments, dapagliflozin is administered to the patient at a dose of 2.5 mg, 5.0 mg, or 10 mg, once a day. In at least embodiment, the dose of dapagliflozin administered is 10 mg.

In some embodiments, the method of treating HFrEF in a patient further comprises administering at least one other therapeutic agent to the patient. The other therapeutic agent is administered with the SGLT2 inhibitor in the same or different pharmaceutical composition, and at the same or different time.

In some embodiments, the other therapeutic agent is an antidiabetic agent, anti-obesity agent, anti-hyperlipidemic agent, anti-atherosclerotic agent, anti-hypertensive agent, anti-platelet agent, antithrombotic agent, or anticoagulant agent.

In some embodiments, the other therapeutic agent is an antidiabetic agent. In some embodiments, the antidiabetic agent is a biguanide and/or a DPP4 inhibitor. In some embodiments, the biguanide is metformin or a pharmaceutically acceptable salt thereof. In some embodiments, the DPP4 inhibitor is saxagliptin, linagliptin, or sitagliptin, or a pharmaceutically acceptable salt thereof.

In some embodiments, the HFrEF patient is receiving one or more standard of care HF agents to treat HF prior to or during administration of the SGLT2 inhibitor. In some embodiments, the standard of care HF agents are selected from the group consisting of angiotensin-converting enzyme (ACE) inhibitors, angiotensin II receptor blockers (ARB), beta blockers, mineralocorticoid receptor agents like mineralocorticoid-receptor antagonists (MRA), neprilysin inhibitors, and diuretics.

In certain embodiments, at least one of the standard of care HF agents is a therapeutically effective amount of an angiotensin-converting enzyme (ACE) inhibitor.

In certain embodiments, at least one of the standard of care HF agents is a therapeutically effective amount of an angiotensin II receptor blocker (ARB).

In certain embodiments, at least one of the standard of care HF agents is a beta blocker.

In certain embodiments, at least one of the standard of care HF agents is a mineralocorticoid receptor agents, such as a mineralocorticoid-receptor antagonist (MRA).

In certain embodiments, at least one of the standard of care HF agents is a neprilysin inhibitor. In some embodiments, the neprilysin inhibitor is combined with an angiotensin II receptor blocker (e.g., sacubitril/valsartan).

In certain embodiments, at least one of the standard of care HF agents is a loop diuretic.

In some embodiments, administration of the SGLT2 inhibitor to the patient results in at least one of the following outcomes:
(i) extends the length of time to a first heart failure (HF) event, and/or a fatal cardiovascular (CV) event; and/or
(ii) reduces worsening of heart failure symptoms; and/or
(iii) decreases the number of heart failure events and/or reduces the incidence of a fatal cardiovascular event.

In some embodiments, an "HF event" is a hospitalization for HF or an urgent HF medical visit.

In some embodiments, the hospitalization for HF comprises a hospital admission lasting at least 24 hours with a primary diagnosis of HF.

In some embodiments, administration of the SGLT2 inhibitor reduces the total number of hospitalizations for HF. The total number of hospitalizations for HF includes first and/or recurrent hospitalizations.

In some embodiments, the hospitalization for HF is due to one or more of the following criteria: (i) new or worsening symptoms of HF experienced by the patient; and/or (ii) objective evidence of new or worsening symptoms of HF; and/or (iii) initiation or intensification of treatment specifically for HF. In some embodiments, the hospitalization for HF is due to all of the above criterion. In some embodiments, new or worsening symptoms of HF experienced by the patient comprises dyspnea, decreased exercise tolerance, fatigue, and/or other symptoms of worsened end-organ perfusion or volume overload. In some embodiments, objective evidence of new or worsening symptoms of HF comprise physical examination findings considered to be due to HF and/or laboratory evidence of new or worsening HF. In some embodiments, the physical examination findings comprise at least two of the following findings: peripheral edema, increasing abdominal distention or ascites, pulmonary rales/crackles/crepitations, increased jugular venous pressure and/or hepatojugular reflux, S3 gallop, and/or clinically significant or rapid weight gain related to fluid retention. In some embodiments, laboratory evidence of new or worsening HF comprises at least one of the following findings: increased B-type natriuretic peptide (BNP)/N-terminal pro-BNP (NT-proBNP) concentrations consistent with decompensation of heart failure; radiological evidence of pulmonary congestion; non-invasive diagnostic evidence of clinically significant elevated left- or right-sided ventricular filling pressure or low cardiac output or invasive diagnostic evidence with right heart catheterization. In some embodiments, the initiation or intensification of treatment specifically for HF comprises at least one of the following: augmentation in oral diuretic therapy, intravenous administration of a diuretic or vasoactive agent, or mechanical or surgical intervention. Mechanical or surgical intervention comprises mechanical circulatory support or mechanical fluid removal.

In some embodiments, an urgent HF medical visit is an emergency room visit for a primary diagnosis of HF but does not require hospitalization. In some embodiments, an urgent HF medical visit is an urgent unscheduled visit to a physician's office for a primary diagnosis of HF. In some embodiments, the patient experienced HF symptoms, and/or had physical examination findings and/or laboratory findings of new or worsening HF. In some embodiments, the patient experiences one or more symptoms of HF selected from the group consisting of dyspnea, decreased exercise tolerance, fatigue, and/or other symptoms of worsened end-organ perfusion or volume overload. In some embodiments, the patient receives initiation or intensification of treatment specifically for HF. In some embodiments, the urgent HF medical visit requires intravenous therapy.

In some embodiments, administration of the SGLT2 inhibitor extends the length of time to a fatal CV event.

In some embodiments, the time to a first heart failure event and/or a fatal cardiovascular event is delayed from 6 months-24 months from the first administration of the SGLT2 inhibitor. In some embodiments, the time to a first heart failure event is delayed 6 months-24 months from the first administration of the SGLT2 inhibitor. In some embodiments, the time to a fatal cardiovascular event is delayed from 6 months-24 months from the first administration of the SGLT2 inhibitor.

In some embodiments, administration of the SGLT2 inhibitor reduces the worsening of HF symptoms in the patient being treated. In some embodiments, the reduced worsening of heart failure symptoms in the patient is for a period of 12-36 months.

In some embodiments, the reduced worsening of heart failure symptoms is characterized by the patient's reduced number of hospitalizations for HF. In some embodiments, the reduced worsening of heart failure symptoms is characterized by the patient's reduced number of urgent HF medical visits. In some embodiments, the urgent HF medical visit is an emergency room visit or an urgent outpatient medical office visit.

In some embodiments, the reduced worsening of heart failure symptoms is characterized by a patient's higher score on the Kansas City Cardiomyopathy Questionnaire (KCCQ) compared to the patient's score prior to SGLT2 inhibitor administration. In some embodiments, the higher score on the KCCQ occurs within 8 months from starting SGLT2 inhibitor administration. In some embodiments, the higher score on the KCCQ is at least 5 points higher than the score prior to SGLT2 inhibitor administration. In some embodiments, the higher score on the KCCQ is at least 10 points higher than the score prior to SGLT2 inhibitor administration. In some embodiments, the higher score on the KCCQ is at least 15 points higher than the score prior to SGLT2 inhibitor administration.

In some embodiments, the reduced worsening of heart failure symptoms is characterized by a patient's higher score on the Patient Global Impression of Change (PGIC) questionnaire compared to the patient's score prior to SGLT2 inhibitor administration. In some embodiments, the higher score on the PGIC occurs within 8 months from starting SGLT2 inhibitor administration. In some embodiments, the higher score on the PGIC is at least 1 point higher than the score prior to SGLT2 inhibitor administration. In some embodiments, the higher score on the PGIC is at least 2 points higher than the score prior to SGLT2 inhibitor administration. In some embodiments, the higher score on the PGIC is more than 2 points higher than the score prior to SGLT2 inhibitor administration.

In some embodiments, the reduced worsening of heart failure symptoms is characterized by a patient's higher score on the Patient Global Impression of Severity (PGIS) questionnaire compared to the patient's score prior to SGLT2 inhibitor administration. In some embodiments, the higher score on the PGIS occurs within 8 months from starting SGLT2 inhibitor administration. In some embodiments, the higher score on the PGIS is at least 1 point higher than the score prior to SGLT2 inhibitor administration. In some embodiments, the higher score on the PGIS is at least 2 points higher than the score prior to SGLT2 inhibitor administration. In some embodiments, the higher score on the PGIS is more than 2 points higher than the score prior to SGLT2 inhibitor administration.

In some embodiments, administration of the SGLT2 inhibitor decreases the number of HF events and/or reduces the incidence of a fatal cardiovascular event.

In some embodiments, administration of the SGLT2 inhibitor decreases the number of HF events. In some embodiments, the HF event is a hospitalization for HF or an urgent HF medical visit. In some embodiments, administration of the SGLT2 inhibitor decreases the number of hospitalizations for HF. In some embodiments, administration of the SGLT2 inhibitor decreases the number of urgent HF medical visits. In some embodiments, the urgent HF medical visit is an emergency room visit. In some embodiments, the urgent HF medical visit requires intravenous therapy.

In some embodiments, administration of the SGLT2 inhibitor reduces the incidence of a fatal cardiovascular event.

In some embodiments, administration of the SGLT2 inhibitor decreases the composite of hospitalizations for HF or a fatal cardiovascular event.

In some embodiments, administration of the SGLT2 inhibitor to adults with HFrEF reduces the risk of cardiovascular death and worsening heart failure and improves heart failure symptoms.

In some embodiments, the HFrEF patient has an eGFR of ≥30 ml/min/1.73 m2 prior to administration of the SGLT2 inhibitor. In some embodiments, the patient with HFrEF maintains an eGFR of ≥30 ml/min/1.73 m2 during administration of the SGLT2 inhibitor.

In some embodiments, the HFrEF patient has a plasma N-terminal pro-B-type natriuretic peptide (NT-proBNP) level of at least 400 pg per milliliter, at least 600 pg per milliliter, or at least 900 pg per milliliter prior to SGLT2 inhibitor administration.

In some embodiments, the patient has been medically diagnosed with symptomatic HFrEF prior to SGLT2 inhibitor administration. In some embodiments, the patient was diagnosed with HFrEF at least two months prior to SGLT2 inhibitor administration.

In some embodiments, the HFrEF patient has atrial fibrillation and/or atrial flutter prior to SGLT2 inhibitor administration. In some embodiments, the HFrEF patient does not have an atrial fibrillation or atrial flutter prior to SGLT2 inhibitor administration. In at least one embodiment, the methods disclosed herein reduce the incidence of atrial fibrillation in HFrEF patients that do not have an atrial fibrillation or atrial flutter prior to SGLT2 inhibitor administration.

In some embodiments, the SGLT2 inhibitor administration decreases HbA1c in the HFrEF patient. In some embodiments, the SGLT2 inhibitor administration decreases systolic blood pressure in the HFrEF patient. In some embodiments, the SGLT2 inhibitor administration decreases the weight of the HFrEF patient. In certain embodiments, the disclosed methods result in a decrease in NT-proBNP levels in the patient. In some embodiments, the decrease occurs within 8 months of the start of SGLT2 inhibitor administration. In certain embodiments, the disclosed methods result in a sustained decline in eGFR (per ml/min/1.73 m$^2$) in the patient.

In some embodiments, the SGLT2 inhibitor administration results in an improvement in NYHA HF classification.

In some embodiments, the SGLT2 inhibitor administration results in a decrease in recurrent hospitalizations for HF or a decrease in recurrent HF events. In some embodiments, recurrent HF events comprise a hospitalization for HF or an urgent HF medical visit.

In some embodiments, the SGLT2 inhibitor administration results in a lower incidence of all-cause deaths in either patients with or without T2D, for example, deaths due to cardiovascular causes and non-cardiovascular causes. In some embodiments, the SGLT2 inhibitor administration results in a lower incidence of non-cardiovascular deaths.

In another aspect, the present disclosure provides a method for reducing the rate of a primary composite endpoint of cardiovascular death, HF hospitalization, or an urgent HF medical visit, in a patient with HFrEF being treated with a SGLT2 inhibitor and standard of care HF agents, wherein the rate is reduced relative to a patient being treated with standard of care HF agents alone. In another aspect, the present disclosure provides a method for reducing the rate of a secondary composite endpoint of cardiovascular death or HF hospitalization, in a patient with HFrEF being treated with a SGLT2 inhibitor and standard of care HF medications, wherein the rate is reduced relative to a patient being treated with standard of care HF agents alone. In some embodiments, the SGLT2 inhibitor is dapagliflozin or a pharmaceutically acceptable salt, solvate, mixed solvate, complex, or prodrug. In some embodiments, the dapagliflozin is administered at 10 mg once daily.

In another aspect, the present disclosure provides a method of preventing or delaying a fatal CV event in a patient with HFrEF without T2D comprising administering to the patient an effective amount of a SGLT2 inhibitor, as described herein.

The present disclosure also provides a method of preventing or delaying a fatal CV event in a patient with HFrEF and T2D, comprising administering to the patient an effective amount of a SGLT2 inhibitor, as described herein.

In some embodiments, the SGLT2 inhibitor is dapagliflozin (FARXIGA®), canagliflozin (INVOKANA®), empagliflozin (JARDIANCE®), ertugliflozin (STEGLATRO®), sotagliflozin, or ipragliflozin, or a pharmaceutically acceptable salt, solvate, mixed solvate, complex, or prodrug.

In at least one embodiment, the SGLT2 inhibitor is dapagliflozin, as described herein. In some embodiments, dapagliflozin is administered at a dosage of 2.5 mg, 5 mg, or 10 mg, once a day. In at least one embodiment, dapagliflozin is administered at a dosage of 10 mg, once a day.

In another aspect, the present disclosure also provides a method of reducing the total number of standard of care HF agents taken by a patient with HFrEF without T2D, comprising administering to the patient an effective amount of a SGLT2 inhibitor, as described herein.

The present disclosure also provides a method of reducing the total number of standard of care HF agents taken by a patient with HFrEF and T2D, comprising administering to the patient an effective amount of a SGLT2 inhibitor.

In some embodiments, administering to the patient with HFrEF an effective amount of a SGLT2 inhibitor, as described herein, results in the patient being able to reduce the total number of standard of care HF agents the patient takes. In some embodiments, the total number of standard of care HF agents is reduced to 2, 3, or 4. Reducing the total number of standard HF agents a patient must take improves health-related quality of life for patients with HFrEF, with and without TD2.

The following example further illustrates the disclosure but, of course, should not be construed as in any way limiting its scope.

Example 1

DAPA-HF Phase III Clinical Trial Results

Introduction

Large clinical trials involving participants with type 2 diabetes (T2D), have demonstrated that inhibitors of sodium-glucose cotransporter 2 (SGLT2) reduce the risk of heart failure (HF) hospitalization.[1-4] Notably, however, most patients in these trials did not have HF at baseline and the benefit of SGLT2 inhibitor treatment largely reflected prevention of incident HF events. Of note, the reduction in heart failure hospitalization was observed early after randomization, raising the possibility of a mechanism or mechanisms of action different from those usually postulated to explain the cardiovascular benefits of glucose-lowering therapies.[5-9] In addition to diuretic and related hemodynamic actions of SGLT2 inhibitors, effects on myocardial metabolism, ion transporters, fibrosis, adipokines and uric acid have also been proposed.[5-9] Most of these actions, as well as preservation of renal function, would also presumably benefit patients with established heart failure, including those without diabetes, in which SGLT2 inhibitors have not been tested.[4,10,11]

The DAPA-HF (Dapagliflozin and Prevention of Adverse-outcomes in Heart Failure) clinical trial was designed to prospectively evaluate the efficacy and safety of the SGLT2 inhibitor dapagliflozin in patients with chronic heart failure with reduced ejection fraction (LVEF ≤40%), both with and without T2D.[12,13] In this Example, the results of the DAPA-HF phase III clinical trial are provided.

Methods

Study Design and Oversight

AstraZeneca sponsored the trial and collected and analyzed data.[12,13] The trial was conducted and reported in accordance with the protocol and the statistical analysis plan. The trial was approved by the ethics committee at each study center. The safety of patients in the trial was reviewed at regular intervals by an independent data monitoring committee. The sponsor's analyses were replicated by an independent academic group at the University of Glasgow.

Study Patients

Eligibility requirements included an age of at least 18 years, New York Heart Association (NYHA) class II, III, or IV symptoms, and an ejection fraction of 40% or less. Patients were required to have a plasma N-terminal pro-B-type natriuretic peptide (NT-proBNP) level of at least 600 pg per milliliter or, if they had been hospitalized for heart failure within the previous 12 months, a NT-proBNP of at least 400 pg per milliliter. Patients with atrial fibrillation or atrial flutter on their baseline electrocardiogram were required to have a NT-proBNP level of at least 900 pg/mL, irrespective of history of heart failure hospitalization. Patients were required to receive standard drug and device therapy for heart failure including an angiotensin-converting enzyme (ACE) inhibitor, angiotensin receptor blocker (ARB), or sacubitril/valsartan; a beta-blocker, unless contraindicated or not tolerated, and a mineralocorticoid receptor (MR) agents, if considered appropriate. Doses were required to be individually optimized, in accordance with the targets recommended in guidelines, and stable for at least 4 weeks (excepting diuretics, which could be dosed flexibly). Investigators were advised that patients with type 2 diabetes should continue to take their glucose-lowering therapies, but these could be adjusted as required. Specifically, the protocol stated that the dose of insulin, sulfonylurea treatment, or both, could be reduced to minimize the risk of hypoglycemia, for example in patients with a baseline hemoglobin A1C (HbA1c) level below 7%.

Exclusion criteria included recent treatment with or intolerance of a SGLT2 inhibitor, type 1 diabetes mellitus, symptoms of hypotension or a systolic blood pressure of less than 95 mm Hg, recent worsening heart failure or other cardiovascular events or procedures (or planned procedures), and an estimated glomerular filtration rate (eGFR) below 30 ml per minute per 1.73 m² of body-surface area (or rapidly declining renal function).

Study Procedures

All the patients provided written informed consent and entered a 14-day enrollment period during which the trial inclusion and exclusion criteria were checked and baseline information gathered, including findings from clinical examination and laboratory measurements. After this period, patients were randomly assigned to receive dapagliflozin 10 mg once daily or matching placebo, in accordance with the sequestered, fixed randomization schedule, using balanced blocks to ensure an approximate one-to-one ratio of the two treatments. Investigators used an interactive voice or web response system to obtain treatment assignment. Randomization was stratified based on a diagnosis of type 2 diabetes, defined as either an established diagnosis or a HbA1c level of 6.5% or greater (≥48 mmol/mol) confirmed in a central laboratory at screening. Patients were evaluated at 14 days and 60 days after randomization, with a focus on assessment of heart failure and volume status, adverse events, and checking renal function and potassium. Further study visits took place at 4 months and at 4-month intervals thereafter. The protocol required that study drug be permanently discontinued if pregnancy or diabetic ketoacidosis occurred. Dose reduction (to dapagliflozin 5 mg daily or matching placebo) or temporary discontinuation, was permitted for any of an acute, unexpected, decline in eGFR, volume depletion or hypotension (or to avoid these), with subsequent increase in dose (or restarting treatment) advised, where possible.

Study Outcomes

The primary outcome was a composite of a first episode of worsening heart failure or death from cardiovascular causes. An episode of worsening heart failure was either an unplanned hospitalization for heart failure or an urgent heart failure visit requiring intravenous therapy.[14] The first of the secondary outcomes was the composite of heart failure hospitalization or cardiovascular death. The additional secondary outcomes were: total number of recurrent heart failure hospitalizations (including repeat admissions) and cardiovascular deaths; change from baseline to 8-months in the total symptom score of the Kansas City Cardiomyopathy Questionnaire (KCCQ) using a scale from 0 to 100, with a higher score indicating fewer symptoms and a 5 or greater point change considered clinically meaningful[15]; the incidence of a composite worsening renal function outcome consisting of a 50% or greater sustained decline in eGFR, end-stage renal disease (defined as a sustained eGFR <15 mL/min/1.73 m$^2$, sustained dialysis treatment or renal transplantation) or renal death; and death from any cause; in all cases sustained meant lasting for at least 28 days.[12]

Outcomes were adjudicated by a clinical-end-points committee, blinded to treatment assignment, according to pre-specified criteria.

Statistical Analysis

A hazard ratio (HR) of 0.80 for dapagliflozin compared with placebo was presumed for the primary outcome. Using a two-sided alpha of 5%, we calculated that 844 primary endpoints would provide a statistical power of 90% for the test of the hypothesis. With an expected annual event rate of 11% in the placebo treatment group, approximately 4500 patients were estimated to provide the required number of primary events, based on an anticipated recruitment period of 18 months and an average follow-up period of approximately 24 months. A closed testing procedure was used, including a prespecified hierarchical testing of the primary and secondary endpoints in the order specified above. Type I error was controlled at a two-sided 0.0499 alpha level for multiplicity across primary and secondary endpoints and taking account of one interim efficacy analysis.

Data from all randomly assigned patients were included in the analyses of the primary and secondary outcomes, according to the intention-to-treat principle. Baseline characteristics were summarized as means and standard deviations, medians and inter-quartile ranges, or percentages. Longitudinal measures, such as glycated hemoglobin level (HbA1c) and body weight, were analyzed using mixed model for repeated measurements, and the least-squares mean differences between treatment groups were estimated, together with 95% confidence intervals. Time-to-event data were evaluated with the use of Kaplan-Meier estimates and Cox proportional hazards models, stratified by diabetes status, with history of heart failure hospitalization and treatment as fixed-effect factors (for the renal endpoint, baseline eGFR was included instead of history of heart failure hospitalization); hazard ratios, 95% confidence intervals, and two-sided P values were calculated with the use of the Cox models.

Total (including recurrent) events were analyzed using a semi-parametric proportional rates model to test the treatment effect and to quantify the treatment difference.[16]

KCCQ total symptom score was analyzed as a composite rank-based endpoint, incorporating patient vital status at 8 months along with change in score from baseline to 8 months in surviving patients, using the rank analysis of covariance method, with a corresponding win ratio used to estimate the magnitude of treatment effect.[17] The consistency of the treatment effect among 14 prespecified subgroups were assessed. The prespecified safety analyses included: serious adverse events; adverse events associated with discontinuation of study treatment; "adverse events of interest" i.e., volume depletion, renal events, major hypoglycemic events, bone fractures, diabetic ketoacidosis, amputations; Fournier's gangrene; and laboratory findings of note. Other adverse events were not routinely collected in view of the extensive prior collective of prior safety data for dapagliflozin. The safety analyses were performed in patients who underwent randomization and received at least one dose of dapagliflozin or placebo. Fisher's exact test was used to compare rates of adverse events. Analyses were performed using Stata, version 15 (College Station Tex., USA) and R version 3.5.1 (R Foundation for Statistical Computing, Vienna, Austria).

Results

Study Patients

From Feb. 15, 2017, through Aug. 17, 2018, 4744 patients were randomly assigned to receive dapagliflozin 10 mg once daily or matching placebo at 410 centers in 20 countries (FIG. 1). The characteristics of the patients and therapies for heart failure were well balanced between the trial groups at baseline (Table 1).

TABLE 1

Characteristics of the Patients at Baseline*

| Characteristic | Dapagliflozin (N = 2373) | Placebo (N = 2371) |
|---|---|---|
| Age - yr | 66.2 ± 11.0 | 66.5 ± 10.8 |
| Female sex - no (%) | 564 (23.8) | 545 (23.0) |
| Race - no. (%)† | | |
| White | 1662 (70.0) | 1671 (70.5) |
| Black or African American | 122 (5.1) | 104 (4.4) |
| Asian | 552 (23.3) | 564 (23.8) |
| Other | 37 (1.6) | 32 (1.3) |
| Region - no. (%) | | |
| North America | 335 (14.1) | 342 (14.4) |
| South America | 401 (16.9) | 416 (17.5) |

TABLE 1-continued

Characteristics of the Patients at Baseline*

| Characteristic | Dapagliflozin (N = 2373) | Placebo (N = 2371) |
|---|---|---|
| Europe | 1094 (46.1) | 1060 (44.7) |
| Asia-Pacific | 543 (22.9) | 553 (23.3) |
| NYHA functional classification - no. (%) | | |
| II | 1606 (67.7) | 1597 (67.4) |
| III | 747 (31.5) | 751 (31.7) |
| IV | 20 (0.8) | 23 (1.0) |
| Heart rate - beats/min | 71.5 ± 11.6 | 71.5 ± 11.8 |
| Systolic blood pressure - mm Hg | 122.0 ± 16.3 | 121.6 ± 16.3 |
| Left ventricular ejection fraction - % | 31.2 ± 6.7 | 30.9 ± 6.9 |
| Median NT-proBNP (IQR) - pg/ml | 1428 (857,2655) | 1446 (857,2641) |
| Body-mass index‡ | 28.2 ± 6.0 | 28.1 ± 5.9 |
| Principal cause of heart failure - no. (%) | | |
| Ischemic | 1316 (55.5) | 1358 (57.3) |
| Non-ischemic | 857 (36.1) | 830 (35.0) |
| Unknown | 200 (8.4) | 183 (7.7) |
| Medical history - no. (%) | | |
| Hospitalization for heart failure | 1124 (47.4) | 1127 (47.5) |
| Atrial fibrillation | 916 (38.6) | 902 (38.0) |
| Diabetes mellitus¶ | 993 (41.8) | 990 (41.8) |
| Estimated GFR - ml/min/1.73 m² of body-surface area | 66.0 ± 19.6 | 65.5 ± 19.3 |
| Estimated GFR rate < 60 ml/min/1.73 m² - no. (%) | 964 (40.7) | 967 (40.7) |
| Device therapy - no (%) | | |
| Implantable cardioverter-defibrillator‡ | 622 (26.2) | 620 (26.1) |
| Cardiac-resynchronization therapy ** | 190 (8.0) | 164 (6.9) |
| Heart failure medication at randomization visit - no (%) | | |
| Diuretic | 2216 (93.4) | 2217 (93.5) |
| ACE inhibitor | 1332 (56.1) | 1329 (56.1) |
| ARB | 675 (28.4) | 632 (26.7) |
| Sacubitril/valsartan | 250 (10.5) | 258 (10.9) |
| Beta-blocker | 2278 (96.0) | 2280 (96.2) |
| Mineralocorticoid receptor antagonist | 1696 (71.5) | 1674 (70.6) |
| Digitalis | 445 (18.8) | 442 (18.6) |
| Glucose-lowering medication at randomization visit - no (%)‡‡ | | |
| Biguanide | 504 (50.8) | 512 (51.7) |
| Sulfonylurea | 228 (23.0) | 210 (21.2) |
| DPP-4 inhibitor | 161 (16.2) | 149 (15.1) |
| GLP-1 receptor agonist | 11 (1.1) | 10 (1.0) |
| Insulin | 274 (27.6) | 266 (26.9) |

*Plus-minus values are means ±SD. There were no significant differences between the two groups for any variable.

Percentages may not total 100 because of rounding.

ACE denotes angiotensin-converting enzyme, ARB angiotensin-receptor blocker, DPP-4 dipeptidyl peptidase 4, GFR glomerular filtration rate, GLP-1 glucagon-like peptide 1, IQR interquartile range, LVEF left ventricular ejection fraction, MRA mineralocorticoid receptor antagonist, N-terminal pro-B-type natriuretic peptide and NYHA New York Heart Association.

†Race was reported by the investigators.

§The body-mass index is the weight in kilograms divided by the square of the height in meters.

¶An additional 82 patients in the dapagliflozin group and 74 in the placebo group had previously undiagnosed diabetes defined as a glycated hemoglobin level of 6.5% or greater (≥48 mmol/mol) measured in a central laboratory at both screening and randomization.

†† In patients with a history of diabetes at baseline: 993 in the dapagliflozin group and 990 in the placebo group.

‡Either implantable cardioverter-defibrillator or cardiac resynchronization therapy with a defibrillator.

**Cardiac-resynchronization therapy with or without a defibrillator.

Study-Drug Administration and Follow-Up

Except for discontinuations owing to death, the study drug was stopped in 249 patients (10.5%) receiving dapagliflozin and 258 patients (10.9%) receiving placebo (P=0.71). At the last assessment, among patients taking the study medication, 2039 (98.1%) in the dapagliflozin group remained on 10 mg daily; 1993 (98.2%) were on the equivalent dose of placebo. No patients in the dapagliflozin group and 2 patients in the placebo group had unknown vital status at the end of the trial (FIG. 1). The median duration of follow-up was 18.2 months.

Study Outcomes

Figures 2A, 2B, 2C, 2D:
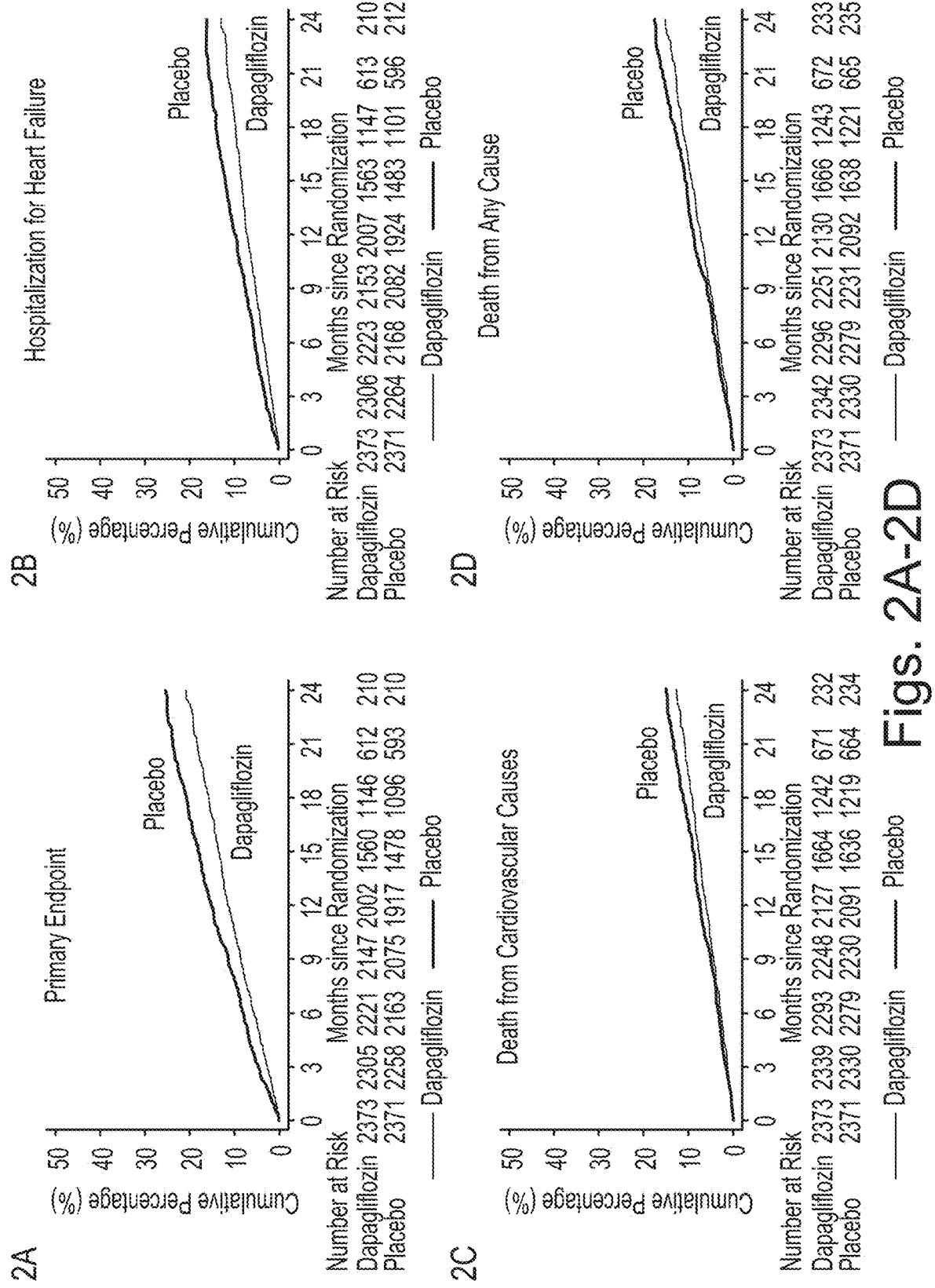
FIGS. 2A-2D are graphs depicting cardiovascular outcomes from the DAPA-HF phase 3 clinical trial (See Example 1).

A worsening heart failure event or death from cardiovascular causes (the primary end point) occurred in 386 patients (16.3%) in the dapagliflozin group and 502 patients (21.2%) in the placebo group (hazard ratio, 0.74; 95% confidence interval [CI], 0.65 to 0.85; P<0.001 (FIG. 2A and Table 2). Event rates for all three components of the composite outcome favored dapagliflozin; most worsening heart failure events were hospitalizations (FIG. 2 and Table 2). Of the patients receiving dapagliflozin, 231 (9.7%) were hospitalized for heart failure, as compared with 318 patients (13.4%) receiving placebo (hazard ratio, 0.70; 95% CI, 0.59 to 0.83; P<0.001) (FIG. 2B and Table 2). Death due to cardiovascular causes occurred in 227 patients (9.6%) in the dapagliflozin group and 273 patients (11.5%) in the placebo group (hazard ratio, 0.82; 95% CI, 0.69 to 0.98; P<0.03) (FIG. 2C and Table 2). Over the duration of the trial, the numbers of patients who would need to have been treated with dapagliflozin to prevent one primary event was 21.

The secondary composite outcome of heart failure hospitalization or death from cardiovascular causes was reduced by dapagliflozin (hazard ratio, 0.75; 95% CI, 0.65 to 0.85; P<0.001) (Table 2). There were 567 total first and recurrent events (340 hospitalizations for heart failure and 227 deaths from cardiovascular causes in 382 patients) in the dapagliflozin arm and 742 total events (469 hospitalizations for heart failure and 273 deaths from cardiovascular causes in 495 patients) in the placebo arm, yielding a rate ratio of 0.75 (95% CI 0.65, 0.88; P<0.001) (Table 2).

The KCCQ total symptom score increased from baseline to month 8 by a mean of 6.1±18.6 points in the dapagliflozin group and 3.3±19.2 points in the placebo group (between-group difference, 2.8 points; 95% CI, 1.6 to 4.0 (win ratio, 1.18; 95% CI 1.11, 1.26; P<0.001) (Table 2). Compared with placebo, more patients in the dapagliflozin group had a five or greater point improvement in score (58% vs. 51%; OR 1.15, 95% CI 1.08, 1.23; P<0.001) and fewer had a deterioration (25% vs. 33%; OR 0.84, 95% CI 0.78, 0.90; P<0.001).

The prespecified renal composite outcome occurred in 28 patients (1.2%) taking dapagliflozin and 39 (1.6%) taking placebo (hazard ratio, 0.71; 95% CI, 0.44 to 1.16; P=0.17) (Table 2).

Figure 3:
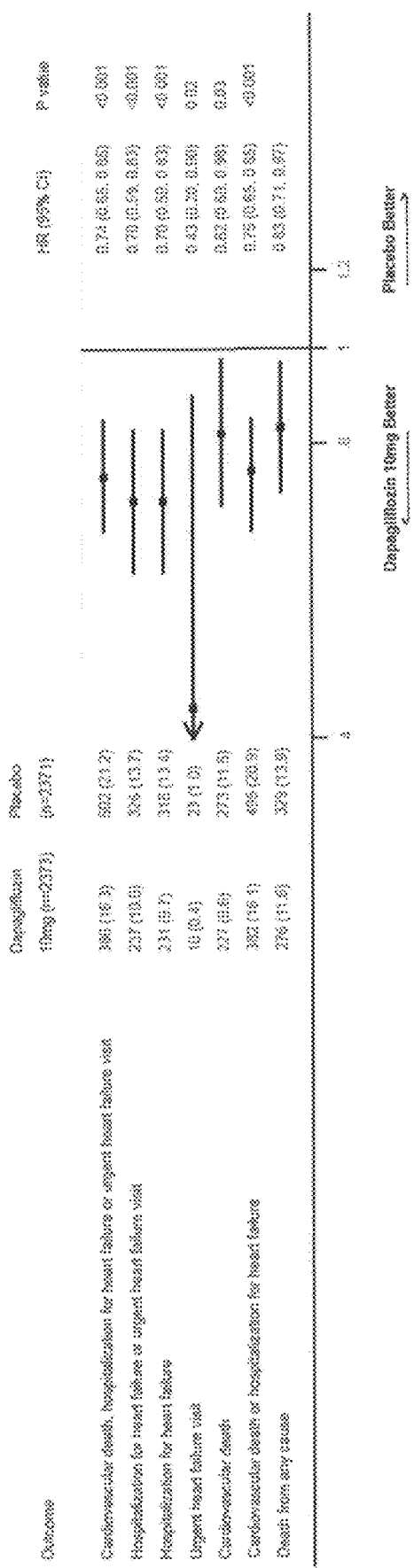
FIG. 3 provides a summary of the effects of dapagliflozin on worsening heart failure and mortality from the DAPA-HF phase 3 clinical trial (See Example 1). This figure shows the primary composite endpoint, which was a composite of death from cardiovascular causes, hospitalization for heart failure, or an urgent heart failure visit requiring intravenous therapy, and each of its components. The narrower composite of death from cardiovascular causes or hospitalization for heart failure and death from any cause, which were secondary outcomes, are also shown.

A total of 276 patients (11.6%) in the dapagliflozin group and 329 patients (13.9%) in the placebo group died from any cause (hazard ratio 0.83; 95% CI, 0.71 to 0.97) (FIG. 2D and Table 2). The effects of dapagliflozin of worsening heart failure and death are summarized in FIG. 3.

Figure 4:
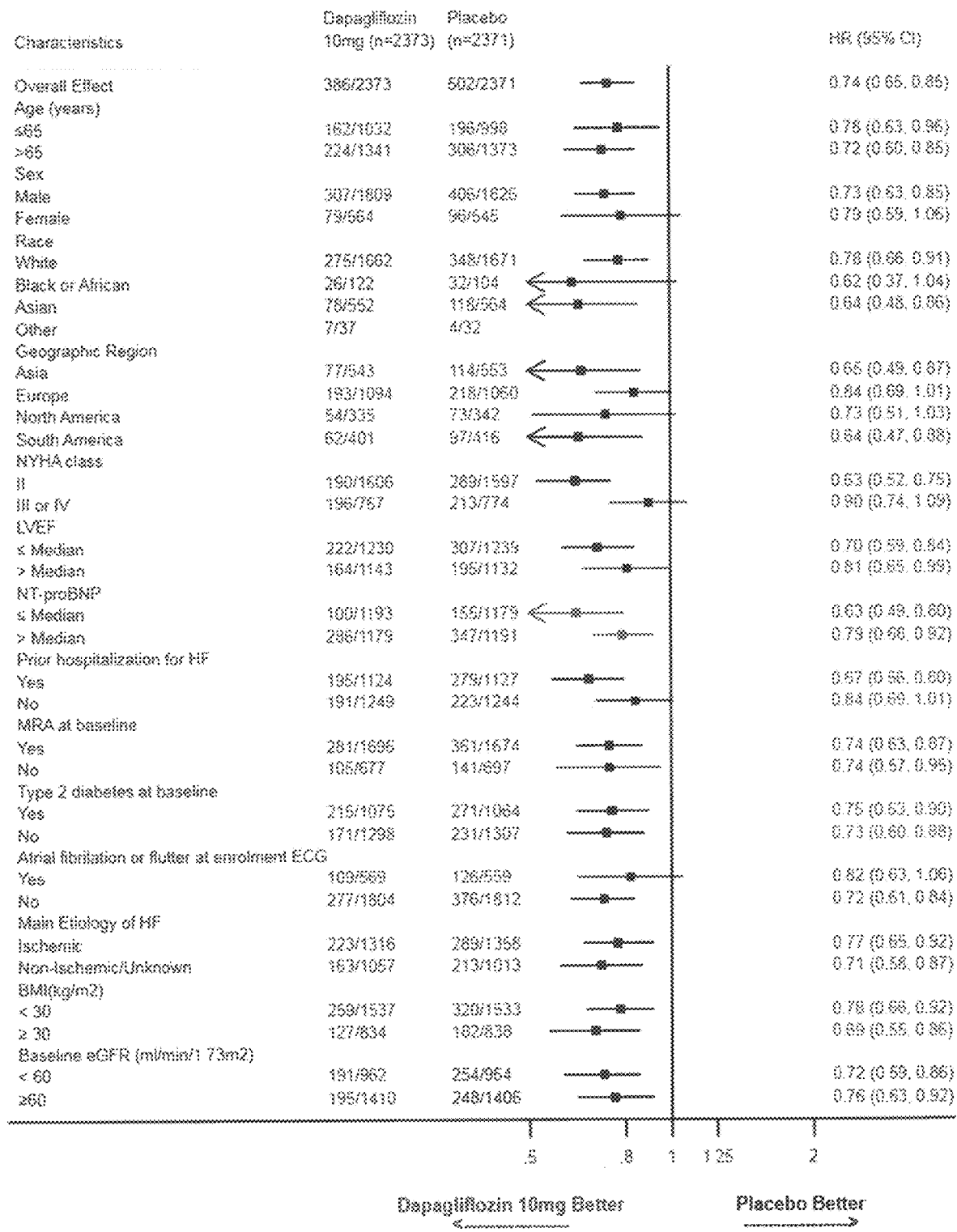
FIG. 4 depicts the primary composite outcome according to prespecified subgroups, from the DAPA-HF phase 3 clinical trial ((See Example 1). Race was reported by the investigators. The body-mass index (BMI) is the weight in kilograms divided by the square of the height in meters. NYHA=New York Heart Association; LVEF=left ventricular ejection fraction; NT-proBNP=N-terminal pro-B-type natriuretic peptide; MRA=mineralocorticoid receptor antagonist; and eGFR=estimated glomerular filtration rate.

The effect of dapagliflozin on the primary outcome was generally consistent across prespecified subgroups, including in patients without diabetes at baseline, although the benefit appeared less in patients in NYHA functional class III and IV compared with class II (FIG. 4). In a post hoc subgroup analysis of patients taking sacubitril-valsartan at baseline, the dapagliflozin to placebo hazard ratio for the primary outcome was 0.75 (95% CI, 0.50, 1.13) compared with 0.74 (0.65, 0.86) in those not taking sacubitril-valsartan.

TABLE 2

Efficacy and Safety

| Variable | Dapagliflozin (N = 2373) | | Placebo (N = 2371) | | Hazard Ratio, Rate Ratio‡ or Win ratio† | P Value |
|---|---|---|---|---|---|---|
| | No. (%) | Events/100 Patient-Yr | No. (%) | Events/100 Patient-Yr | (95% CI) | |
| Efficacy Outcomes | | | | | | |
| Primary composite outcome* | 386 (16.3) | 11.6 | 502 (21.2) | 15.6 | 0.74 (0.65-0.85) | <0.001 |
| Hospitalization for heart failure or an urgent heart failure visit | 237 (10.0) | 7.1 | 326 (13.7) | 10.1 | 0.70 (0.59-0.83) | <0.001 |
| Hospitalization for heart failure | 231 (9.7) | 6.9 | 318 (13.4) | 9.8 | 0.70 (0.59-0.83) | <0.001 |
| Urgent heart failure visit | 10 (0.4) | 0.3 | 23 (1.0) | 0.7 | 0.43 (0.20-0.90) | 0.02 |
| Cardiovascular death | 227 (9.6) | 6.5 | 273 (11.5) | 7.9 | 0.82 (0.69-0.98) | 0.03 |
| Secondary outcomes | | | | | | |
| Cardiovascular death or hospitalization for heart failure | 382 (16.1) | 11.4 | 495 (20.9) | 15.3 | 0.75 (0.65-0.85) | <0.001 |
| Total number of (first and recurrent) heart failure hospitalizations and cardiovascular death‡ | 567 | — | 742 | — | 0.75 (0.65-0.88)‡ | <0.001 |
| Change in KCCQ total symptom score at 8 mo.† | 6.1 ± 18.6 | — | 3.3 ± 19.2 | — | 1.18 (1.11-1.26)† | <0.001 |
| Worsening renal function†† | 28 (1.2) | 0.8 | 39 (1.6) | 1.2 | 0.71 (0.44-1.16) | 0.17 |
| Death from any cause | 276 (11.6) | 7.9 | 329 (13.9) | 9.6 | 0.83 (0.71-0.97) | NA |
| Safety Outcomes‖ | | | | | | |
| Any serious adverse event (including death) | 895 (37.8) | — | 994 (42.0) | — | | <0.01 |
| Discontinuation of study drug due to adverse event | 111 (4.7) | — | 116 (4.9) | — | | 0.79 |
| Adverse events of interest | | | | | | |
| Volume depletion | 178 (7.5) | — | 162 (6.8) | — | | 0.40 |
| Renal adverse event | 153 (6.5) | — | 170 (7.2) | — | | 0.36 |

TABLE 2-continued

Efficacy and Safety

| Variable | Dapagliflozin (N = 2373) | | Placebo (N = 2371) | | Hazard Ratio, Rate Ratio‡ or Win ratio† | P Value |
|---|---|---|---|---|---|---|
| | No. (%) | Events/100 Patient-Yr | No. (%) | Events/100 Patient-Yr | (95% CI) | |
| Fracture | 49 (2.1) | — | 50 (2.1) | — | — | 1.00 |
| Amputation | 13 (0.5) | — | 12 (0.5) | — | — | 1.00 |
| Major hypoglycemia‡‡ | 4 (0.2) | — | 4 (0.2) | — | — | NA |
| Diabetic Ketoacidosis** | 3 (0.1) | — | 0 (0) | — | — | NA |
| Fournier gangrene | 0 (0) | — | 1 (0.04) | — | — | NA |

NA denotes not applicable because P values are reported only for outcomes that were included in the hierarchical-testing strategy and hazard ratios and 95% confidence intervals (CI) are not reported for outcomes with 10 events or fewer.
*Primary composite outcome - analyzed as time-to-first occurrence of urgent heart failure visit, hospitalization for heart failure or death from cardiovascular causes.
‡Total number of (first and recurrent) heart failure hospitalizations and cardiovascular death analyzed by the semi-parametric proportional rates model (Lin et al, 2000[16]; known as the LWYY method) - the treatment effect is a rate ratio
†Scores on the Kansas City Cardiomyopathy Questionnaire (KCCQ) range from 0 to 100, with higher scores indicating fewer symptoms and physical limitations associated with heart failure. The treatment effect is shown as a win-ratio. A value greater than 1 indicates superiority.
††Worsening renal function - composite outcome analyzed as time-to-first occurrence of 50% or greater reduction in eGFR sustained for at least 28 days, end-stage renal disease (ESRD) or death from renal causes. ESRD consisted of eGFR below 15 ml/min/1.73 m$^2$ sustained for at least 28 days, chronic dialysis treatment (sustained for at least 28 days) or kidney transplantation. Acute kidney injury serious adverse events: dapagliflozin 20 (0.8%) and placebo 41 (1.7%), p = 0.007
||The safety population included patients receiving at least one dose of trial medication: dapagliflozin n = 2368 and placebo n = 2368. The numbers reported are patients.
‡‡Major hypoglycemia was defined as hypoglycemia requiring the assistance of another person to actively administer carbohydrates, glucagon, or take other corrective action. All cases occurred in patients with diabetes at baseline.
**All cases of diabetic ketoacidosis occurred in patients with diabetes at baseline.

Other Outcomes

Figure 15:
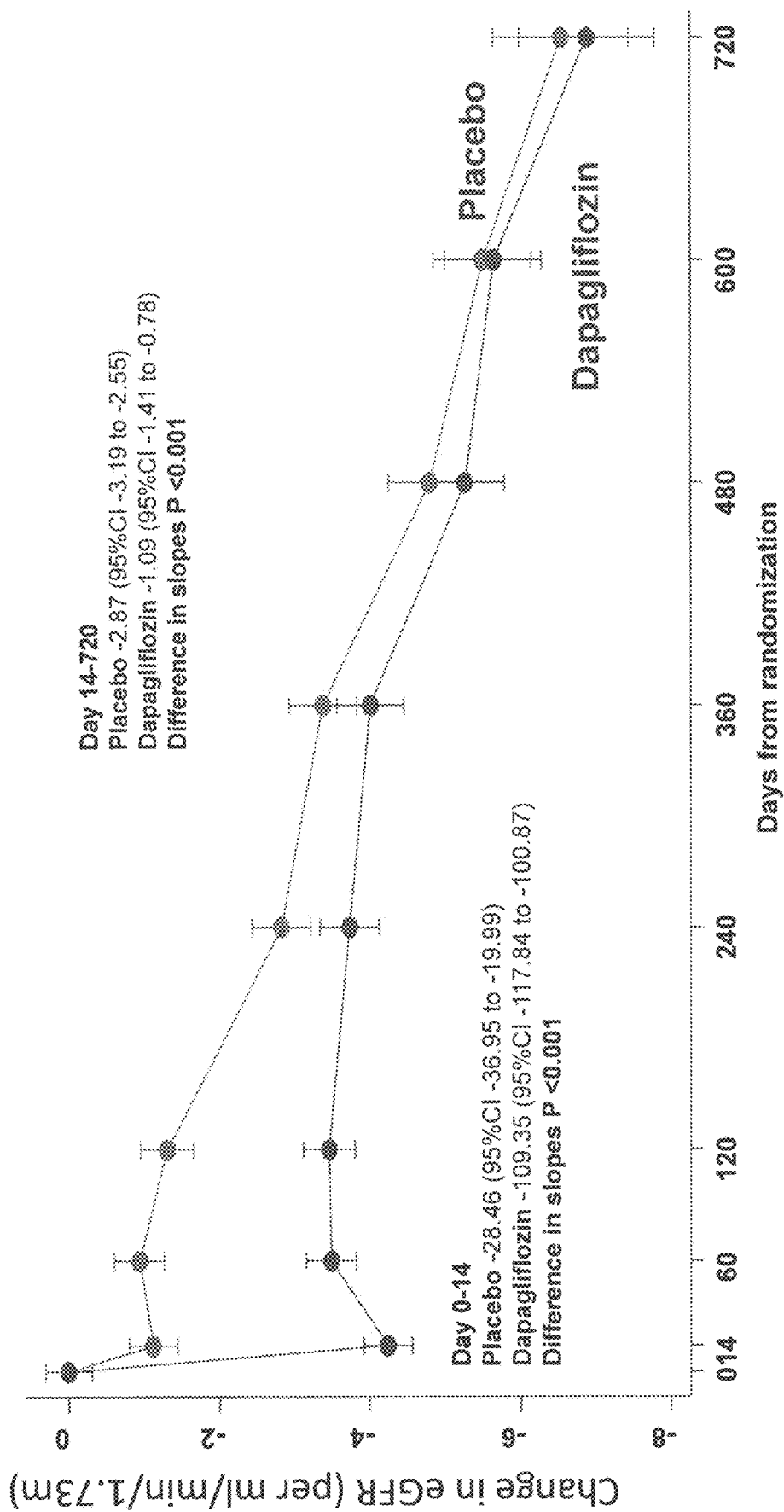
Figure 16:
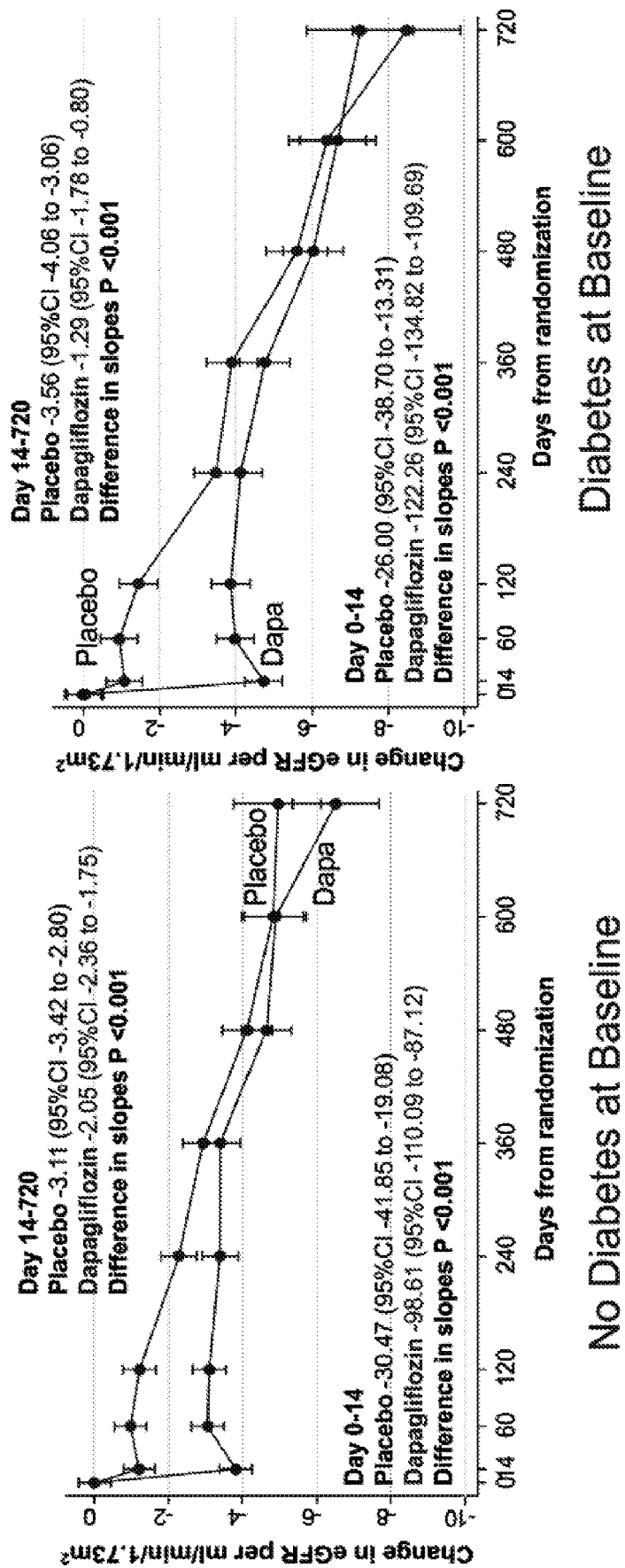

Changes from baseline to 8 months in glycated hemoglobin, hematocrit, plasma potassium, systolic blood pressure, and weight are shown in Table 3. Mean creatinine concentration increased from baseline to 2 weeks by 0.08±0.19 mg per deciliter in the dapagliflozin group and by 0.01±0.17 mg per deciliter in the placebo group (between-group difference, 0.07 mg per deciliter; 95% CI, 0.05 to 0.08; P<0.001); the corresponding changes at 8 months were 0.07±0.24 and 0.04±0.25 mg per deciliter, respectively (difference, 0.02 mg per deciliter; 95% CI, 0.01 to 0.04; P=0.04). Changes from baseline to 720 days in eGFR per ml/min/1.73$^2$ per year were also measured and shown in FIGS. 15 and 16.

TABLE 3

Change in weight and laboratory variables from baseline to 8 month (Visit 6)

| Variable | Dapagliflozin 10 mg | Placebo | Between group difference (95% CI) | |
|---|---|---|---|---|
| HbA1c (%)* | −0.21 ± 1.14 | 0.04 ± 1.29 | −0.25 (−0.36 to −0.14), p < 0.001 | |
| Hematocrit (%) | 2.31 ± 3.90 | −0.19 ± 3.81 | 2.49 (2.26 to 2.73), p < 0.001 | |
| Potassium | 0.07 ± 0.53 | 0.09 ± 0.53 | −0.02 (−0.05 to 0.01), p = 0.298 | |
| Systolic BP (mmHg) | −1.92 ± 14.92 | −0.38 ± 15.27 | −1.41 (−2.31 to −0.52), p = 0.002 | |
| Weight (kg) | −0.88 ± 3.86 | 0.10 ± 4.09 | −0.98 (−1.22 to −0.74), p < 0.001 | |
| Creatinine mg/dL | | | | |
| 14 days | 0.08 ± 0.19 | 0.01 ± 0.17 | 0.07(0.05 to 0.08), p < 0.001 | |
| 8 months | 0.07 ± 0.24 | 0.04 ± 0.25 | 0.02 (0.01 to 0.04), p = 0.001 | |

*Calculated only in patients with diabetes at baseline.

Safety

Prespecified safety outcomes of special interest are shown in Table 2. Five patients assigned to dapagliflozin and 3 assigned to placebo did not receive study treatment and were excluded from the safety analyses. In the dapagliflozin group, 178 patients (7.5%) had an adverse event related to volume depletion, compared to 162 (6.8%) of those assigned to placebo (P=0.40). Serious adverse events related to volume depletion occurred in 29 dapagliflozin treated patients (1.2%) and 40 patients (1.7%) in the placebo group, P=0.23.

Adverse events related to renal dysfunction occurred in 153 patients (6.5%) in the dapagliflozin group versus 170 patients (7.2%) (P=0.36) (Table 2). Serious renal adverse events occurred in 38 dapagliflozin treated patients (1.6%) and 65 patients (2.7%) in the placebo group, P=0.009.

Adverse events rarely required discontinuation of treatment (Table 2). Lower limb amputation and fracture were infrequent and the incidence of each was similar in the two treatment groups (Table 2). Major hypoglycemia (4 patients in the dapagliflozin group and 4 in the placebo group) and diabetic ketoacidosis (3 versus 0) were also uncommon (Table 2). No case of Fournier's gangrene was reported in the dapagliflozin group, compared with one in the placebo group. There was no notable excess of any serious adverse events (SAE) in the dapagliflozin group.

Discussion

In this multicenter randomized placebo-controlled trial of patients with chronic heart failure with reduced left ventricular ejection fraction, dapagliflozin reduced the risk of the primary composite outcome of a first episode of worsening heart failure (hospitalization for heart failure or an urgent heart failure visit requiring intravenous therapy) or death from cardiovascular causes. Each of the three components of this outcome was reduced, as was the total number of heart failure hospitalizations and deaths from cardiovascular causes. Dapagliflozin also improved symptoms of heart failure, as measured by the total symptom score of the Kansas City Cardiomyopathy Questionnaire (KCCQ). The observed benefits, which were substantial and clinically important, occurred early after randomization and were obtained in participants receiving recommended background therapy for heart failure, including renin-angiotensin system blockers, beta-blockers and mineralocorticoid receptor antagonists in a high proportion of patients.

Notably, dapagliflozin was as effective in the 55 percent of patients without type 2 diabetes, as in participants with diabetes. This first demonstration of cardiovascular benefits of a SGLT2 inhibitor in patients without diabetes provides support for prior suggestions that this type of treatment may have beneficial actions other than glucose lowering.[4-11] The findings from the DAPA-HF, therefore, potentially extend the therapeutic role of dapagliflozin beyond diabetes.

The reduction in the primary outcome was generally consistent across the remaining prespecified subgroups although one subgroup suggested possible heterogeneity of treatment effect, with less benefit in patients in NYHA functional class III and IV, compared with class II. However, other subgroups also reflecting more advanced disease, such as lower ejection fraction, worse renal function, and higher NT-proBNP were not consistent with the finding for NYHA class.

The population studied in the DAPA-HF trial was quite distinct from the prior SGLT2 inhibitor trials in that DAPA-HF patients were at much higher risk of heart failure hospitalization and death from cardiovascular causes. Most were already treated with a loop diuretic and a mineralocorticoid receptor antagonist and it was not known whether dapagliflozin would cause the expected initial natriuresis and diuresis seen in other patient groups. It was considered that such effects might lead to volume depletion and worsening renal function, especially as many of our patients had chronic kidney disease. Neither of these two adverse effects turned out to be common (each occurring in less than 8 percent of patients in either treatment group) and serious renal adverse events were uncommon generally, and significantly less frequent in the dapagliflozin group. Overall, few patients stopped study treatment because of any adverse effect (less than 5 percent of patients in either treatment group). Major hypoglycemia was rare, as was diabetic ketoacidosis, and all cases of both adverse events occurred in patients with diabetes.

The baseline use of sacubitril-valsartan, which is more effective than renin-angiotensin system blockade alone at reducing heart failure hospitalization and death from cardiovascular causes, was low.[18] However, the postulated mechanisms of action of SGLT2 inhibition and neprilysin inhibition are distinct and in a post hoc subgroup analysis the benefit of dapagliflozin was similar in patients treated with and without sacubitril-valsartan.[19,20]

In conclusion, the SGLT2 inhibitor dapagliflozin reduced the risk of worsening heart failure and death from cardiovascular causes, and improved symptoms, in patients with heart failure and reduced ejection fraction, including those without Type 2 diabetes.

REFERENCES

[1] Zinman B. et al., "Empagliflozin, Cardiovascular Outcomes, and Mortality in Type 2 Diabetes," *N Engl J Med.* 373(22):2117-2128 (2015).

[2] Neal B. et al., "Canagliflozin and Cardiovascular and Renal Events in Type 2 Diabetes," *N Engl J Med.* 377(7):644-657 (2017).

[3] Wiviott S. D. et al., "Dapagliflozin and Cardiovascular Outcomes in Type 2 Diabetes, *N Engl J Med.* 380: 347-357 (2019).

[4] Perkovic V. et al., Canagliflozin and Renal Outcomes in Type 2 Diabetes and Nephropathy, *N Engl J Med.* 380: 2295-2306 (2019).

[5] Packer M. et al., "Effects of Sodium-Glucose Cotransporter 2 Inhibitors for the Treatment of Patients With Heart Failure: Proposal of a Novel Mechanism of Action," *JAMA Cardiol.* 2(9):1025-1029 (2017).

[6] Verma S. and McMurray J. J. V., "SGLT2 inhibitors and mechanisms of cardiovascular benefit: a state-of-the-art review," *Diabetologia* 61(10):2108-2117 (2018).

[7] Inzucchi S. E. et al., "Improvement in Cardiovascular Outcomes With Empagliflozin Is Independent of Glycemic Control," *Circulation* 138(17):1904-1907 (2018).

[8] Lytvyn Y. et al., "Sodium Glucose Cotransporter-2 Inhibition in Heart Failure: Potential Mechanisms, Clinical Applications, and Summary of Clinical Trials," *Circulation* 136(17):1643-1658 (2017).

[9] Bonnet F. and Scheen A. J., "Effects of SGLT2 inhibitors on systemic and tissue low-grade inflammation: The potential contribution to diabetes complications and cardiovascular disease," *Diabetes Metab.* 44: 457-464 (2018).

[10] Wanner C. et al., "Empagliflozin and Progression of Kidney Disease in Type 2 Diabetes," *N Engl J Med.* 375: 323-334 (2016).

[11] Zelniker T. A. et al., "SGLT2 inhibitors for primary and secondary prevention of cardiovascular and renal outcomes in type 2 diabetes: a systematic review and meta-analysis of cardiovascular outcome trials," *Lancet* 393: 31-39 (2019).

[12] McMurray J. J. V. et al., "DAPA-HF design paper—A trial to evaluate the effect of the sodium glucose co-transporter 2 inhibitor dapagliflozin on morbidity and mortality in patients with heart failure and reduced left ventricular ejection fraction (DAPA-HF), *Eur J Heart Fail.* 21: 665-675 (2019).

[13] McMurray J. J. V. et al., "The Dapagliflozin and Prevention of Adverse-Outcomes in Heart Failure (DAPA-HF) trial: baseline characteristics," *Eur J Heart Fail.*, doi: 10.1002/ejhf.1548. [Epub ahead of print] (2019 Jul. 15).

[14] Hicks K. A. et al., "Standardized Data Collection for Cardiovascular Trials Initiative (SCTI) 2017 Cardiovascular and Stroke Endpoint Definitions for Clinical Trials," *Circulation* 137:961-972 (2018).

[15] Green C. P., "Development and evaluation of the Kansas City Cardiomyopathy Questionnaire: a new health status measure for heart failure," *J Am Coll Cardiol.* 35: 1245-1255 (2000).

[16] Lin D. Y. et al., "Semiparametric regression for the mean and rate functions of recurrent events," *J R Stat Soc Series B Stat Methodol* 62: 711-730 (2000).

[17] Wang D. and Pocock S., "A win ratio approach to comparing continuous non-normal outcomes in clinical trials." *Pharm Stat.* 15:238-245 (2016).

[18] McMurray J. J. et al., "Angiotensin-neprilysin inhibition versus enalapril in heart failure," *N Engl J Med.* 371:993-1004 (2014).

[19] McMurray J. J., "Neprilysin inhibition to treat heart failure: a tale of science, serendipity, and second chances," *Eur J Heart Fail.* 17:242-247 (2015).

[20] Packer M., "Reconceptualization of the Molecular Mechanism by Which Sodium-Glucose Cotransporter 2 Inhibitors Reduce the Risk of Heart Failure Events," *Circulation* 140:443-445 (2019).

Example 2

DAPA-HF Phase III Clinical Trial Results—Effect of Dapagliflozin on HF Symptoms, Health Status, and Quality of Life Introduction Patients with HF and HFrEF are at high risk of disease progression, resulting in clinical deterioration, repeat hospitalizations, and death. Bui, A. L. et al., *Nat Rev Cardiol* 8:30-41 (2011). Importantly, they also experience a high burden of debilitating symptoms, which impact their daily function and quality of life. Indeed, some treatments for HFrEF that have a favorable effect on death and hospitalizations do not improve health status (Reddy, P. and Dunn, A. B., *Pharmacotherapy* 20:679-689 (2000), highlighting the high unmet need for additional efficacious therapies that not only improve clinical events, but also reduce symptom burden and physical limitations, and improve the quality of life. In fact, improving patients' health status is a key goal of heart failure management, increasingly recognized by practice guidelines (Tsevat, J. et al., *J Gen Intern Med.* 9:576-582 (1994); Lewis, E. F. et al., *J Heart Lung Transplant* 20:1016-1024 (2001)), and acknowledged by regulators as an important outcome. US FDA, "Treatment for Heart Failure: Endpoints for Drug Development Guidance for Industry," https://wwwfdagov/regulatory-information/search-fda-guidance-documents/treatment-heart-failure-endpoints-drug-development-guidance-industry (2019).

In the DAPA-HF trial, discussed in Example 1, the SGLT2 inhibitor, dapagliflozin, added to other guideline-recommended therapies, reduced the risk of mortality and HF hospitalization, and improved symptoms in 4,744 patients with HFrEF. See also McMurray, J. J. V. et al., *N Engl J Med*, doi: 10.1056/NEJMoa1911303 [Epub ahead of print] (2019 Sep. 19); McMurray, J. J. V. et al., *Eur J Heart Fail* 21: 665-675 (2019); McMurray J. J. V. et al., *Eur J Heart Fail.*, doi: 10.1002/ejhf.1548. [Epub ahead of print] (2019 Jul. 15), incorporated by reference in their entireties. To better understand the effects of dapagliflozin on the broad range of health status outcomes, its effects on the various domains of the KCCQ—a validated, self-administered instrument that quantifies heart failure related symptoms, function and quality of life, were examined.

Methods

The design, baseline characteristics of study patients, and primary results of the DAPA-HF trial were as described in Example 1 and McMurray, J. J. V. et al., *N Engl J Med*, doi: 10.1056/NEJMoa1911303 [Epub ahead of print] (2019 Sep. 19); McMurray, J. J. V. et al., *Eur J Heart Fail* 21: 665-675 (2019); and McMurray J. J. V. et al., *Eur J Heart Fail.*, doi: 10.1002/ejhf.1548. [Epub ahead of print] (2019 Jul. 15). The primary clinical outcome in the DAPA-HF trial was the composite of an episode of worsening heart failure (HF hospitalization or urgent HF visit) or cardiovascular (CV) death, whichever occurred first. Additional clinical outcomes assessed were the occurrence of HF hospitalization or CV death; worsening HF events (HF hospitalizations or urgent HF visits), hospitalization for HF, cardiovascular death, and all-cause death.

Kansas City Cardiomyopathy Questionnaire

The KCCQ was completed electronically by patients, without assistance by site study staff (as validated), and evaluated at randomization, 4-months, and 8-months. The KCCQ is a 23-item, self-administered disease-specific instrument that quantifies symptoms (frequency, severity and recent change), physical function, quality of life, and social function over the prior 2 weeks. In the KCCQ, the total symptom score (TSS) quantifies the symptom frequency and severity, KCCQ clinical summary score (KCCQ-CSS) includes the physical function and symptoms domains, and KCCQ overall summary score (OSS) is derived from the following domains (total symptom score, physical function, quality of life and social function). For each domain, the validity, reproducibility, responsiveness and interpretability have been independently established. Scores are transformed to a range of 0-100, in which higher scores reflect better health status.

Statistical Analysis

In this study, patients were divided into three subgroups, based on the tertiles of baseline KCCQ-TSS (which was the KCCQ domain prespecified as the secondary endpoint): (i) ≤65.6, (ii) 65.7-87.5, (iii) >87.5 points. Baseline characteristics were summarized as means and standard deviations, medians, and interquartile ranges, or percentages. The rates of CV death and worsening HF across the tertiles of KCCQ-TSS (regardless of treatment allocation) were calculated and compared using Kaplan-Meier estimates.

To compare the effects of dapagliflozin vs. placebo on clinical outcomes across the KCCQ-TSS tertiles, we evaluated time-to-event data with the use of Kaplan-Meier estimates and used Cox proportional-hazards models, stratified according to diabetes status, with a history of HF hospitalization and treatment-group assignment as fixed-effect factors to calculate hazard ratios, 95% confidence intervals, and two-sided P values.

The differences between treatment groups in mean KCCQ-TSS, CSS, and OSS at 4 months and 8 months in surviving patients were analyzed, using a mixed model for repeated measurements and estimated the least-squares mean differences between treatment groups adjusted for baseline values. Responder analyses were conducted examining proportions of patients with a deterioration, and clinically important improvements in KCCQ at 8 months. Established, clinically meaningful thresholds for KCCQ (≥5 point (at least small), ≥10 point (moderate), and ≥15 point (large) change) were used for all responder analyses across the KCCQ domains. The proportion of responders was compared between those treated with dapagliflozin versus placebo using multiple imputation to account for missing KCCQ values (see below).

Odds ratios to estimate differences between treatment groups, and their corresponding 95% confidence intervals and 2-sided p-values were estimated from logistic regression models (which included treatment group, stratification variable (T2D at randomization) and baseline KCCQ values); the models used imputed data accounting for missing KCCQ values and estimates were combined using Rubin's rules. Missing data were imputed using a missing at random assumption and a predictive mean matching multiple imputation model, and a method of Fully Conditional Specification as implemented in the SAS Procedure MI (FCS statement). The imputation model included the treatment group, type 2 diabetes randomization stratum, KCCQ scores at baseline, 4 months, and 8 months, and a categorical variable representing the number of investigator reported HF events (0, 1, ≥2 events) in the interval from randomization to 4 months, and in the interval from 4 to 8 months. Deaths were handled by assigning a worst rank value. Patients with a baseline KCCQ score which was too high for them to experience an improvement according to a certain threshold (e.g., baseline score ≥95 points for the 5-point threshold) were defined as improved if their score remained high (i.e., ≥95 points) at 8 months. Similarly, patients with at KCCQ score at baseline which was too low for them to experience a deterioration were defined as deteriorated if their score remained low at 8 months. All analyses were conducted using STATA version 15.1 (College Station, Tex., USA) and SAS version 9.4 (SAS Institute, Cary, N.C., USA). A P-value of 0.05 was considered statistically significant.

Results

Overall, 4744 patients were randomized. Baseline KCCQ TSS was available for 4,443 (93.7%) patients. The median KCCQ TSS was 77.1 (IQR 58.3-91.7). The number and proportion of patients in the KCCQ-TSS tertiles are shown in Table 4.

TABLE 4

| | KCCQ-TSS at Baseline | | | | p-value |
| --- | --- | --- | --- | --- | --- |
| | Tertile 1<br>N = 1,487 | Tertile 2<br>N = 1,564 | Tertile 3<br>N = 1,392 | Total<br>N = 4,443 | for trend |
| Age | 65.8 (11.0) | 66.4 (10.5) | 66.8 (10.5) | 66.3 (10.7) | 0.007 |
| Sex | | | | | <0.001 |
| Female | 414 (27.8%) | 344 (22.0%) | 233 (16.7%) | 991 (22.3%) | |
| Male | 1,073 (72.2%) | 1,220 (78.0%) | 1,159 (83.3%) | 3,452 (77.7%) | |
| Race: | | | | | <0.001 |
| Asian | 183 (12.3%) | 349 (22.3%) | 455 (32.7%) | 987 (22.2%) | |
| African American | 100 (6.7%) | 59 (3.8%) | 52 (3.7%) | 211 (4.7%) | |
| White | 1,175 (79.0%) | 1,141 (73.0%) | 864 (62.1%) | 3,180 (71.6%) | |
| Other | 29 (2.0%) | 15 (1.0%) | 21 (1.5%) | 65 (1.5%) | |
| Geographic Region | | | | | <0.001 |
| Asia/Pacific | 180 (12.1%) | 342 (21.9%) | 447 (32.1%) | 969 (21.8%) | |
| Europe | 803 (54.0%) | 750 (48.0%) | 511 (36.7%) | 2,064 (46.5%) | |
| North America | 226 (15.2%) | 222 (14.2%) | 196 (14.1%) | 644 (14.5%) | |
| South America | 278 (18.7%) | 250 (16.0%) | 238 (17.1%) | 766 (17.2%) | |
| Systolic BP (mmHg) | 121.5 (16.1) | 121.4 (16.3) | 122.6 (16.4) | 121.8 (16.3) | 0.102 |
| Diastolic BP (mmHg) | 73.9 (10.1) | 73.3 (10.4) | 73.5 (10.9) | 73.5 (10.5) | 0.151 |
| Pulse (bpm) | 72.7 (12.1) | 71.0 (11.4) | 70.4 (11.4) | 71.4 (11.7) | <0.001 |
| Body Mass Index | 29.8 (6.6) | 28.0 (5.6) | 27.0 (5.2) | 28.3 (5.9) | <0.001 |
| Creatinine (mg/dL) | 1.2 (0.4) | 1.2 (0.3) | 1.2 (0.3) | 1.2 (0.3) | 0.007 |
| EGFR (mL/min/1.73 m$^2$) | 64.2 (19.1) | 65.9 (19.2) | 66.9 (19.2) | 65.7 (19.2) | <0.001 |
| NT-proBNP (pmol/L) | 1716.2 (964.0-3274.7) | 1389.0 (827.8-2517.9) | 1291.6 (798.9-2172.4) | 1432.0 (855.1-2635.7) | <0.001 |
| Main etiology of HF | | | | | 0.034 |
| Ischemic | 865 (58.2%) | 886 (56.6%) | 755 (54.2%) | 2,506 (56.4%) | |
| Non-Ischemic | 497 (33.4%) | 565 (36.1%) | 518 (37.2%) | 1,580 (35.6%) | |
| Unknown | 125 (8.4%) | 113 (7.2%) | 119 (8.5%) | 357 (8.0%) | |
| LVEF (%) | 31.2 (6.8) | 31.0 (6.8) | 31.0 (6.7) | 31.1 (6.8) | 0.184 |
| NYHA class | | | | | <0.001 |
| II | 745 (50.1%) | 1,108 (70.8%) | 1,139 (81.8%) | 2,992 (67.3%) | |
| III | 724 (48.7%) | 443 (28.3%) | 242 (17.4%) | 1,409 (31.7%) | |
| IV | 18 (1.2%) | 13 (0.8%) | 11 (0.8%) | 42 (0.9%) | |
| KCCQ TSS | 51.0 (40.6-58.3) | 79.2 (72.4-83.3) | 97.9 (92.7-100.0) | 77.1 (58.3-91.7) | <0.001 |
| Hypertension | 1,185 (79.7%) | 1,144 (73.1%) | 995 (71.5%) | 3,324 (74.8%) | <0.001 |
| History of T2DM | 683 (45.9%) | 618 (39.5%) | 567 (40.7%) | 1,868 (42.0%) | 0.004 |
| History of Atrial fib | 654 (44.0%) | 575 (36.8%) | 493 (35.4%) | 1,722 (38.8%) | <0.001 |
| Prior HF Hosp (N) | 777 (52.3%) | 825 (52.7%) | 715 (51.4%) | 2,317 (52.1%) | 0.642 |
| Prior MI (%) | 678 (45.6%) | 694 (44.4%) | 605 (43.5%) | 1,977 (44.5%) | 0.249 |
| Prior PCI (%) | 476 (32.0%) | 547 (35.0%) | 511 (36.7%) | 1,534 (34.5%) | 0.008 |
| Prior CABG (%) | 253 (17.0%) | 281 (18.0%) | 225 (16.2%) | 759 (17.1%) | 0.56 |
| ACEI | 818 (55.0%) | 887 (56.7%) | 781 (56.1%) | 2,486 (56.0%) | 0.544 |
| ARB | 413 (27.8%) | 428 (27.4%) | 371 (26.7%) | 1,212 (27.3%) | 0.501 |
| ARNI | 170 (11.4%) | 168 (10.7%) | 152 (10.9%) | 490 (11.0%) | 0.654 |
| Diuretic | 1,430 (96.2%) | 1,470 (94.0%) | 1,260 (90.5%) | 4,160 (93.6%) | <0.001 |
| Digoxin | 297 (20.0%) | 287 (18.4%) | 233 (16.7%) | 817 (18.4%) | 0.025 |
| Betablocker | 1,432 (96.3%) | 1,506 (96.3%) | 1,336 (96.0%) | 4,274 (96.2%) | 0.653 |
| MRA | 1,098 (73.8%) | 1,118 (71.5%) | 933 (67.0%) | 3,149 (70.9%) | <0.001 |
| Antiplatelet | 774 (52.1%) | 862 (55.1%) | 781 (56.1%) | 2,417 (54.4%) | 0.028 |
| Anticoagulant | 674 (45.3%) | 642 (41.0%) | 567 (40.7%) | 1,883 (42.4%) | 0.012 |
| Statin | 985 (66.2%) | 1,054 67.4%) | 944 (67.8%) | 2,983 (67.1%) | 0.366 |
| History of ICD | 302 (20.3%) | 336 (21.5%) | 283 (20.3%) | 921 (20.7%) | 0.975 |
| CRT-D | 94 (6.3%) | 96 (6.1%) | 90 (6.5%) | 280 (6.3%) | 0.879 |
| Cardiac Pacemaker | 117 (7.9%) | 119 (7.6%) | 107 (7.7%) | 343 (7.7%) | 0.852 |
| CRT-D or CRT-P | | | | | |
| History of ICD or CRT-D | 396 (26.6%) | 432 (27.6%) | 373 (26.8%) | 1,201 (27.0%) | 0.910 |

Patient Characteristics

Compared to participants with higher KCCQ-TSS scores at baseline, those with lower scores were younger, more often women, white, and enrolled in Europe and the Americas. They also had a higher body mass index, and natriuretic peptide levels; and a lower eGFR (Table 4); more likely to be in NYHA functional class III/IV, than in class II, and to have Type 2 diabetes and atrial fibrillation. With respect to background HF medications, patients with lower baseline KCCQ-TSS were more frequently treated with mineralocorticoid receptor antagonists (MRAs) and diuretics. Baseline use of angiotensin receptor neprilysin inhibitors (ARNI) was generally low but similar across age groups. The proportion of patients treated with implantable cardiac devices was generally comparable across the KCCQ-TSS subgroups.

Clinical Outcomes

Figure 5:
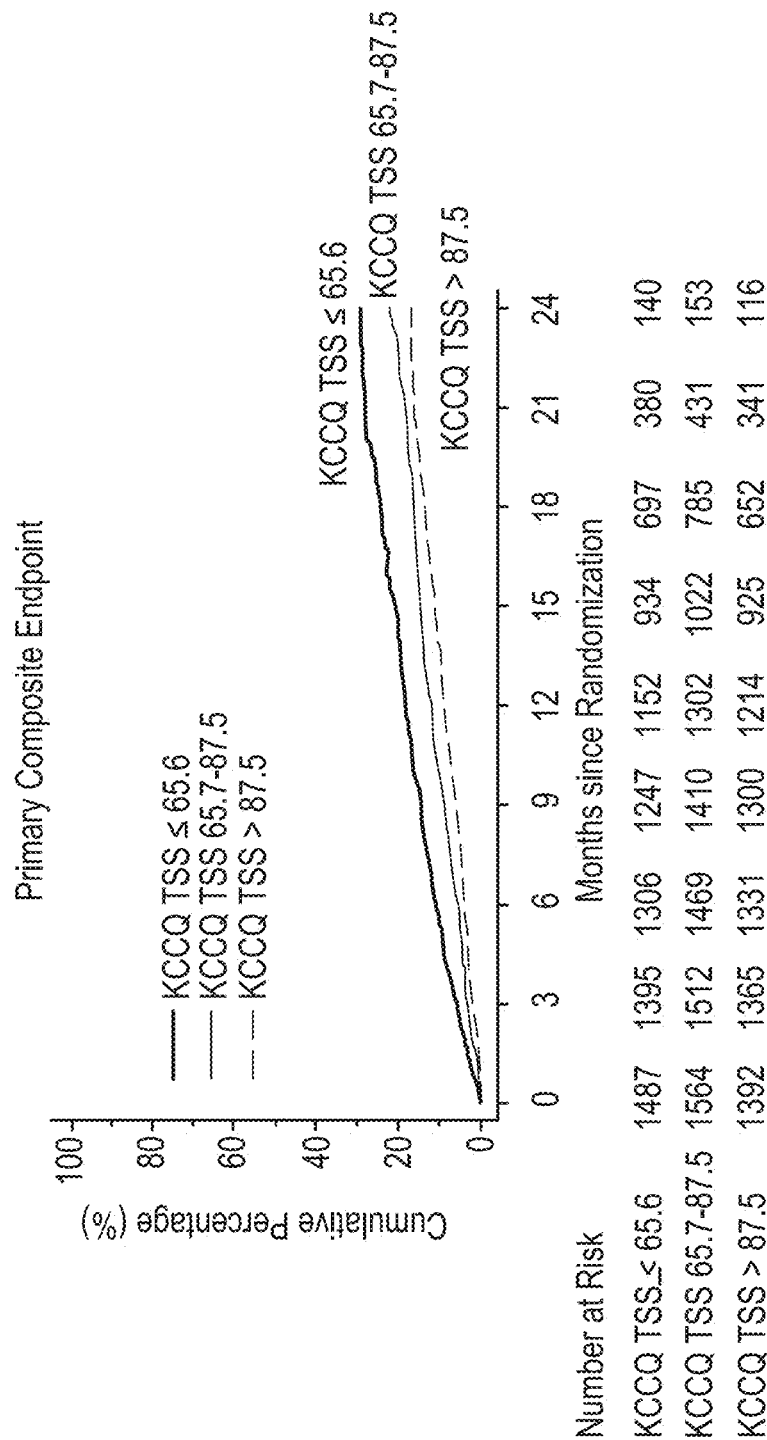
FIG. 5 is a graph depicting baseline KCCQ Total Symptom Scores (TSS) divided into three tertiles (i) ≤65.6, (ii) 65.7-87.5, and (iii) >87.5 points, and showing the changes in cumulative percentage within those tertiles over 24 months since randomization.

Patients with lower baseline KCCQ-TSS experienced higher rates of CV death or worsening HF (25.0%, 17.3%, and 13.6% in patients across KCCQ-TSS tertiles of ≤65.6, 65.7-87.5, >87.5, respectively; P<0.001). In the Cox proportional hazards models, patients with lower baseline KCCQ-TSS had a higher risk of CV death or worsening HF (Tertile >87.5: Referent; Tertile 65.7-87.5: HR 1.30 (95% C: 1.08-1.56), p=0.006; Tertile ≤65.6: HR 1.93 (95% 1.62-2.30), p<0.001; FIG. 5).

Figure 6:
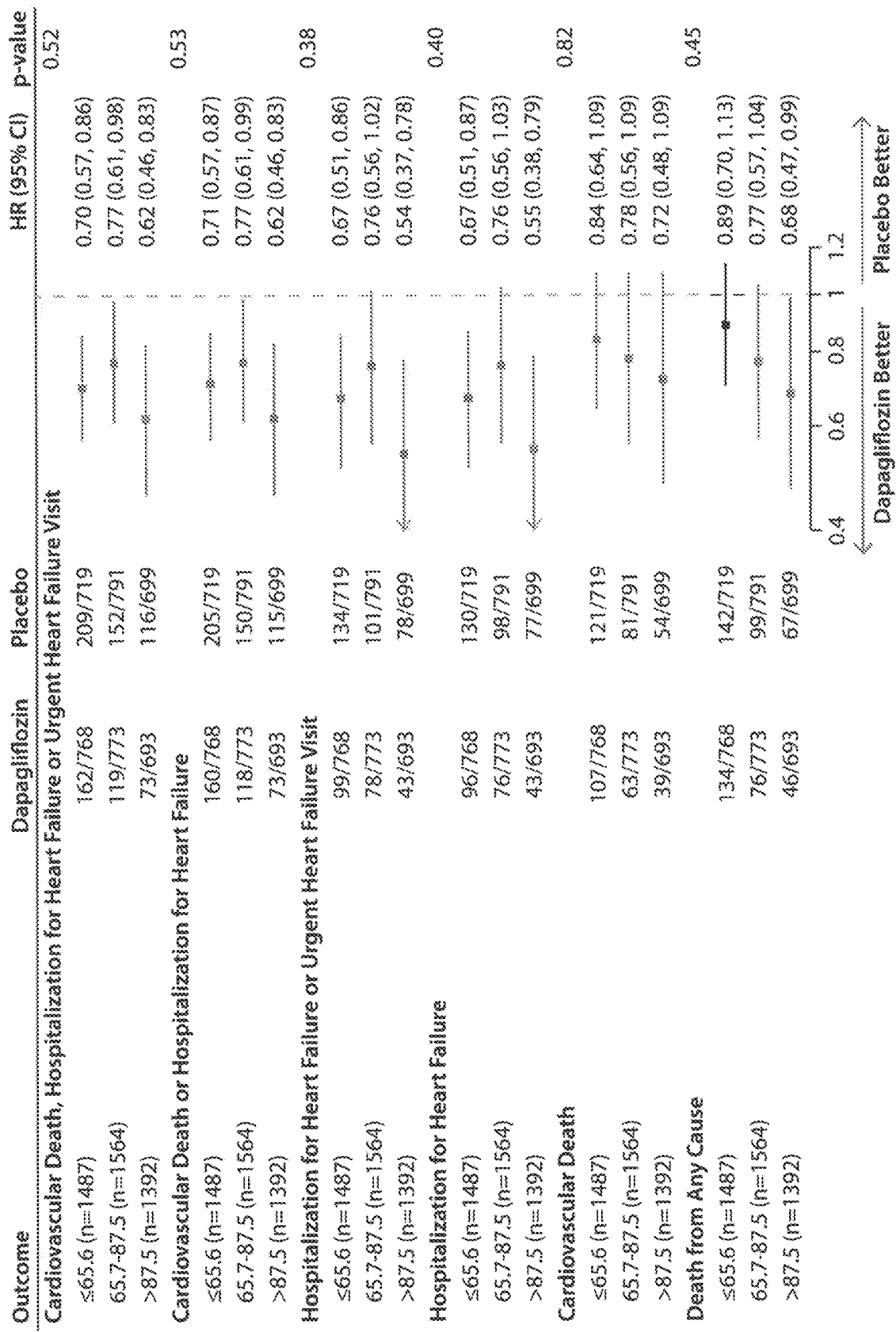
FIG. 6 depicts six clinical outcomes for patients on dapagliflozin vs. placebo in the DAPA-HF trial, including: cardiovascular death, HF hospitalization, or urgent HF visit; cardiovascular death or HF hospitalization; HF hospitalization or urgent HF visit; HF hospitalization; cardiovascular death; and death from any cause.
Figure 9A:
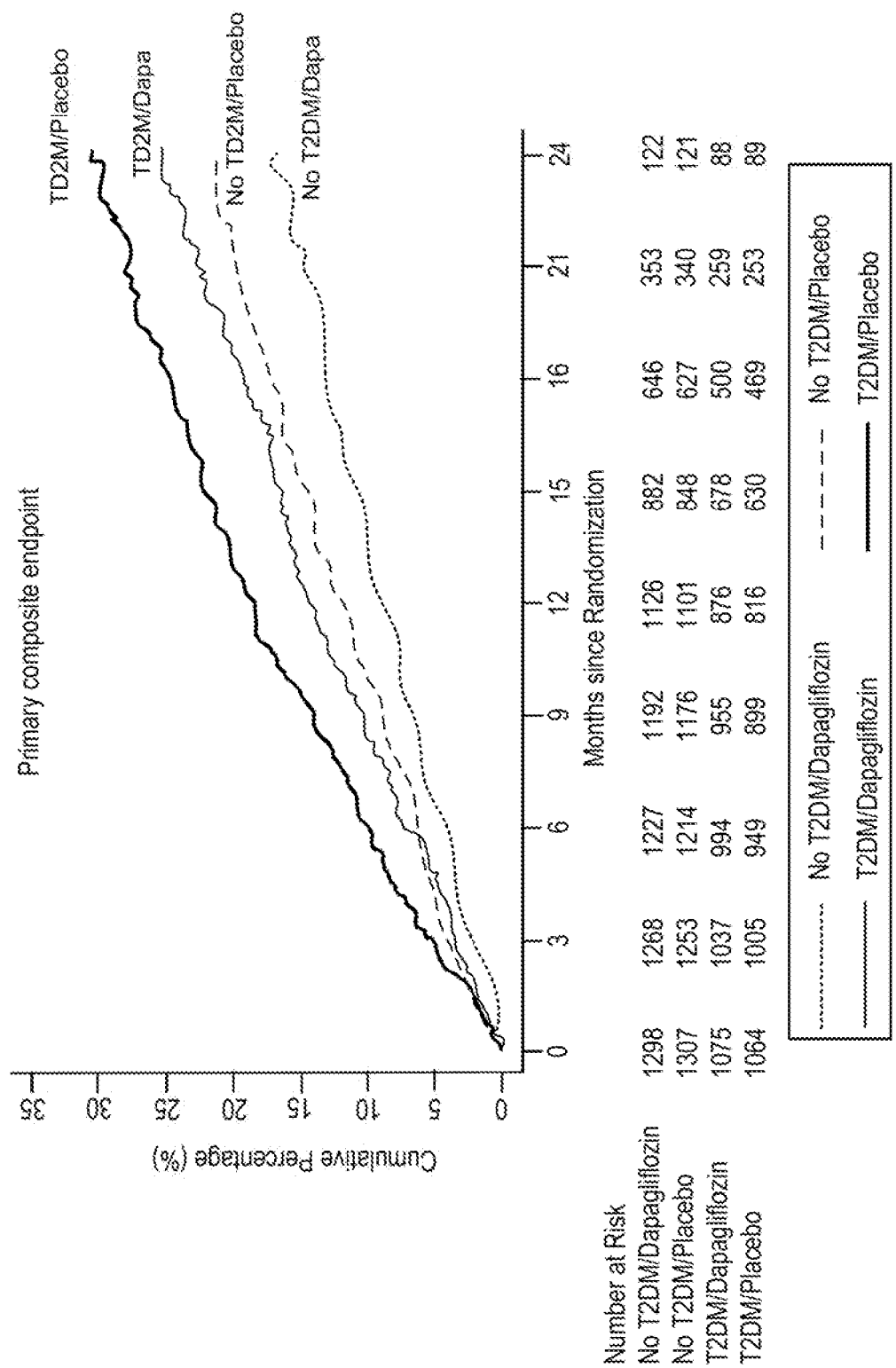
FIGS. 9A-9D are graphs depicting the primary composite endpoint (FIG. 9A) of patients from the DAPA-HF trial, and its components—i.e., hospital admission for heart failure (FIG. 9B), death from cardiovascular causes (FIG. 9C) and death from all causes (FIG. 9D), according to diabetes status at baseline.
Figure 9B:
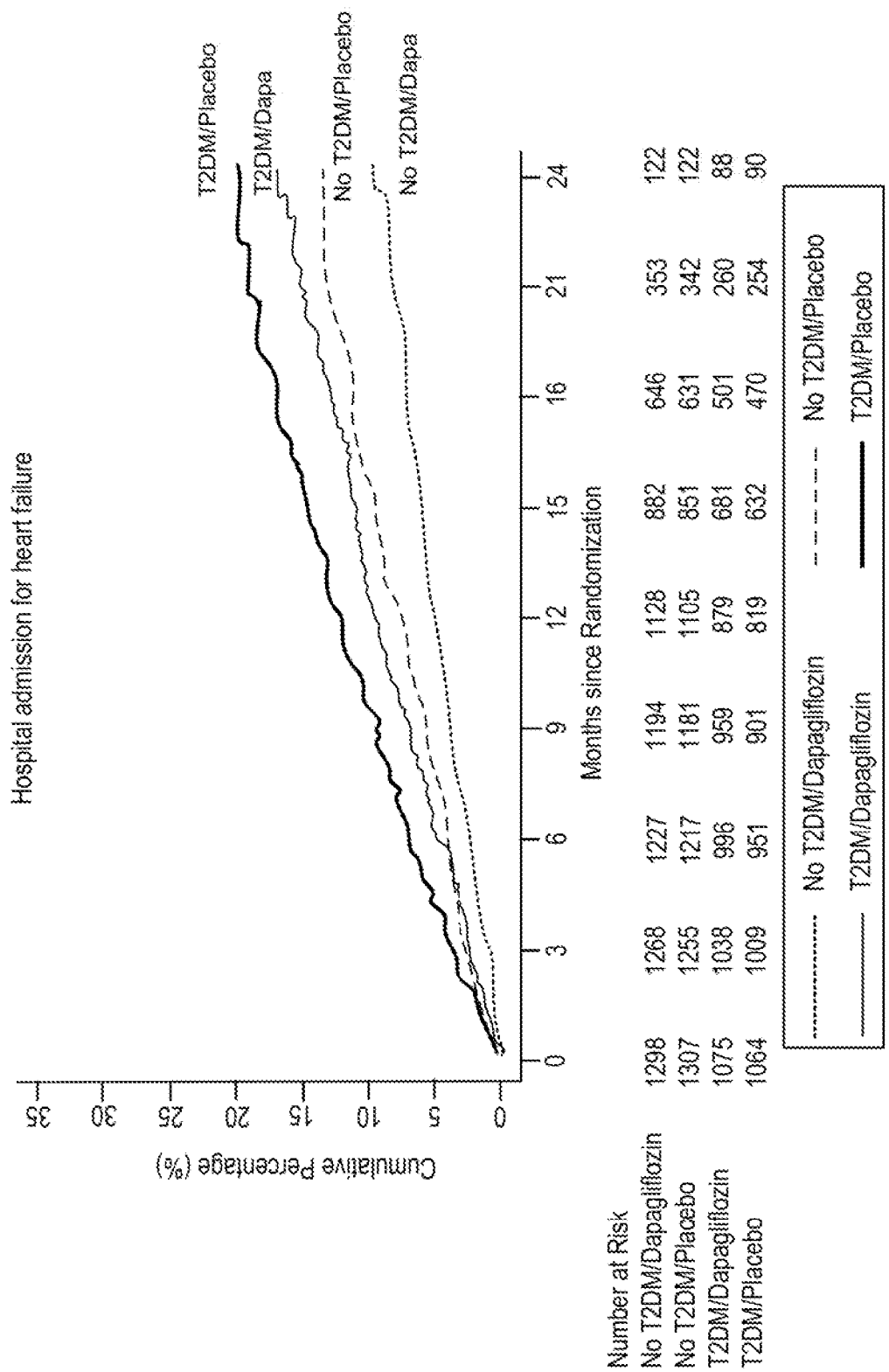
Figure 9C:
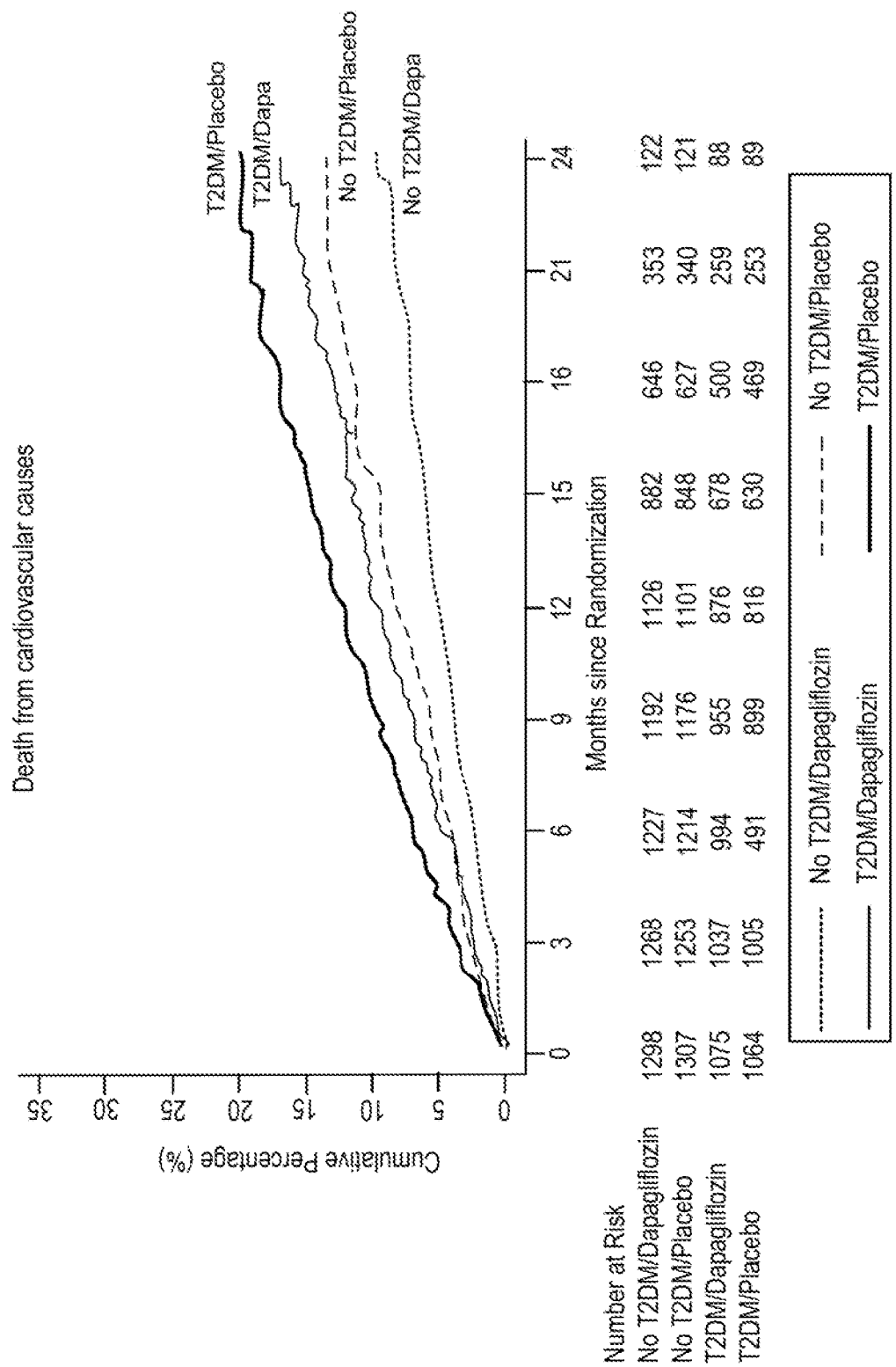
Figure 9D:
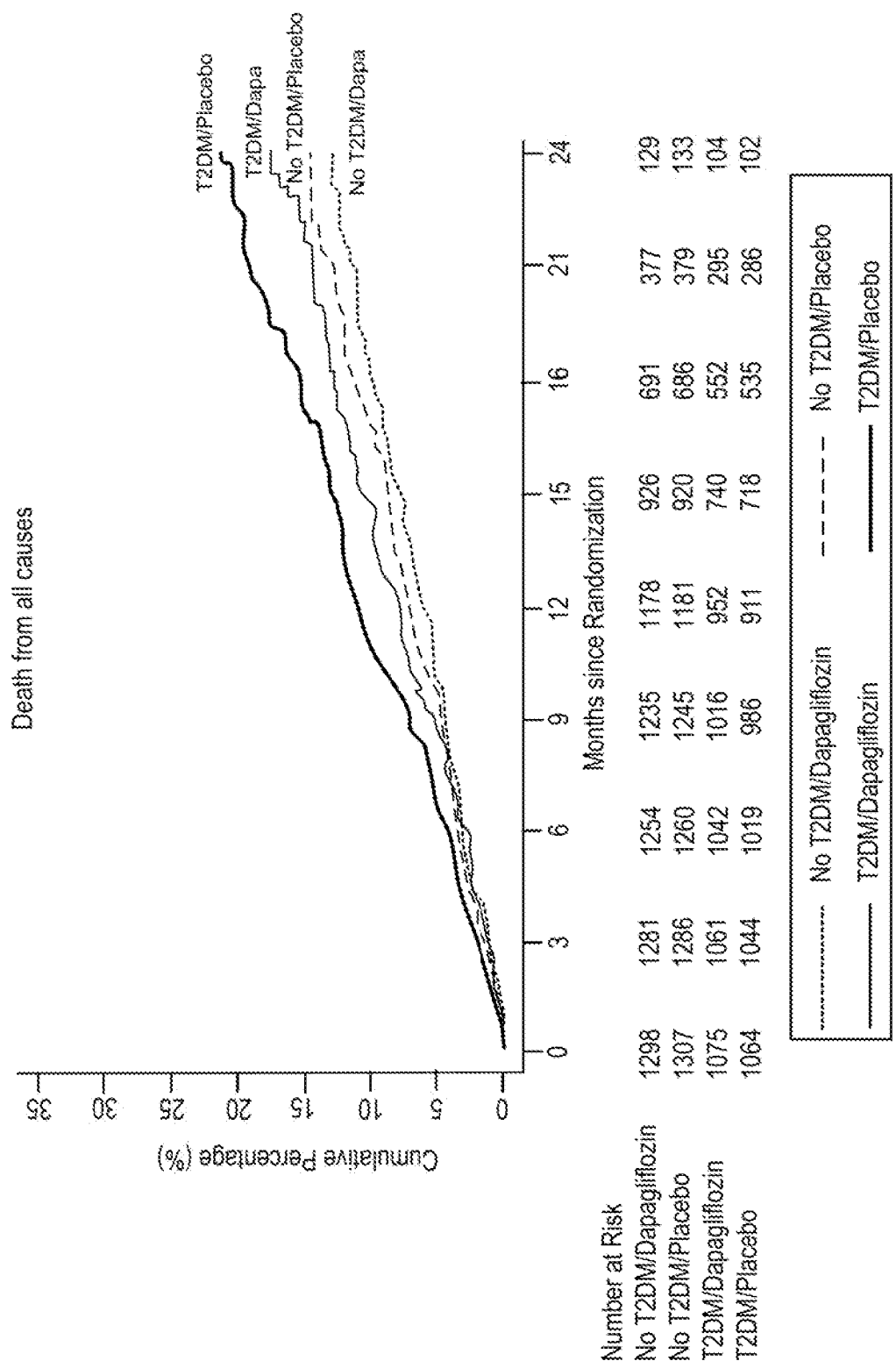

The effects of dapagliflozin on the range of clinical outcomes are summarized in FIG. 6. Dapagliflozin reduced the primary outcome of CV death or worsening HF across the entire range of KKCQ-TSS, with no evidence of treatment effect heterogeneity (HR (95% CIs) from lowest to highest tertile: 0.70 (0.57-0.86), 0.77 (0.61-0.98), and 0.62 (0.46-0.83), respectively; P for heterogeneity=0.52). Similar results were observed for CV death or hospitalization for HF; worsening HF events; HF hospitalizations; CV death; and all-cause death (FIG. 6; all P values for heterogeneity non-significant).

Health Status Outcomes

The mean changes in KCCQ-TSS, CSS, and OSS over time are presented in FIGS. 7A, 7B, and 7C, respectively. Patients treated with dapagliflozin had a modest, but significant, improvement in mean KCCQ-TSS, CSS, and OSS at 4 months (1.9, 1.8, and 1.7 points higher than placebo, respectively; P<0.0001 for all). These beneficial effects were amplified over time, with the corresponding mean differences at 8 months being 2.8, 2.5, and 2.3 points higher in favor of dapagliflozin vs. placebo (P<0.0001 for all).

The results of the responder analysis are shown in FIGS. 8A-8F. Fewer patients treated with dapagliflozin had a clinically significant deterioration (≥5 point decline in KCCQ-TSS (25.3% vs. 32.9%; OR 0.84, 95% CI 0.78-0.90; p<0.0001); and more patients treated with dapagliflozin had at least small (58.3% vs. 50.9%), moderate (54.5% vs. 47.6%), and large (54.0% vs. 48.2%) improvements (corresponding odds ratio (OR), 95% CI: 1.15, (1.08-1.23); 1.15 (1.08-1.22); 1.14 (1.07-1.22); numbers needed to treat (NNT)=14 (10-23), 15 (11-25), and 18 (12-35), respectively; P<0.0001 for all; FIGS. 8A-8B). The findings were similar for KCCQ-CSS and OSS (FIGS. 8C-8F).

Discussion

In this prospective study, which evaluated prespecified assessments of health status using KCCQ in the DAPA-HF trial, treatment with dapagliflozin reduced the risk of all key clinical events, including the primary composite endpoint of CV death or worsening HF, and its components, to a similar extent across the entire range of KCCQ at baseline, indicating that the beneficial effects of dapagliflozin on HF outcomes are independent of the health status impairment at baseline. Furthermore, dapagliflozin significantly improved KCCQ-TSS, CSS, and OSS (which collectively encompass symptoms, physical function, quality of life, and social function), and these effects were amplified over time. Finally, significantly fewer patients treated with dapagliflozin experienced clinically meaningful deterioration, and significantly more experienced at least small, moderate, and large clinically meaningful improvements in health status. These effects were substantial, with numbers needed to treat ranging between 12 and 18 after just 8 months of treatment.

These results have several important implications. First, the analyses of the clinical outcomes across the subgroups of baseline KCCQ-TSS show no evidence of heterogeneity in the benefit of dapagliflozin by the magnitude of symptomatic impairment at baseline. Previously reported prespecified subgroup analyses of the primary endpoint (CV death or worsening HF) suggested that the benefit of dapagliflozin may be more pronounced in patients with NYHA class II vs class III-IV. However, NYHA class, while prognostically important, represents a more subjective, arbitrary, and non-patient-centric assessment of symptom burden; and considering this report, the observation from the prior NYHA class subgroup analysis was likely a chance finding.

Second, the findings substantially expand on the previously reported effects of dapagliflozin on health status, as measured by KCCQ, in patients with HFrEF. In the Dapagliflozin Effects on Biomarkers, Symptoms, and Functional Status in Patients With Heart Failure with Reduced Ejection Fraction (DEFINE-HF) trial, a modestly sized randomized, placebo-controlled trial performed across 26 sites in the United States, dapagliflozin was also shown to have favorable effects on several domains of KCCQ—with slightly greater mean differences in favor of dapagliflozin vs. placebo than those observed in the DAPA-HF trial, but comparable responder analyses and numbers needed to treat, after just 12 weeks of treatment. Nassif, M. E. et al., *Circulation* 140:1463-1476 (September 2019). The findings confirm these beneficial effects on symptoms, function, and quality of life in a much larger, global trial with a longer duration of follow up. Collectively, the findings from both the DEFINE-HF and DAPA-HF trials indicate that dapagliflozin significantly improves heart failure related health status, as measured by KCCQ, with the benefits emerging early and being sustained long-term.

Third, the magnitude of the improvement in KCCQ that was observed with dapagliflozin vs. placebo in the DAPA-HF trial compare favorably with other efficacious therapies for HFrEF. As an example, in the Systolic Heart Failure Treatment With the If inhibitor Ivabradine Trial (SHIFT), ivabradine demonstrated a 2.4 point mean improvement in KCCQ-OSS, and 1.8 point mean improvement in KCCQ-CSS after 12 months of treatment. Ekman, I. et al., *Eur Heart J* 32:2395-2404 (2011). In the PARADIGM-HF trial, Lewis, E. F. et al., *Circ Heart Fail.* 10: doi: 10.1161/CIRCHEARTFAILURE.116.003430 (2017), sacubitril-valsartan demonstrated a 1.3- and 0.9-point improvements in KCCQ-OS and KCCQ-CS respectively, over enalapril after 8 months of treatment. In the HF-ACTION trial, Flynn, K. E. et al., *JAMA* 301:1451-1459 (2009), exercise therapy in HFrEF produced a 1.9 point improvement in KCCQ-OSS. In the MADIT-CRT trial of cardiac resynchronization therapy (CRT) in patients with HFrEF and prolonged QRS interval, Veazie, P. J. et al., *J Am Coll Cardiol.* 60:1940-1944 (2012), treatment with CRT resulted in 2.0, 2.0, and 2.4 point improvements in KCCQ-TSS, CSS, and OSS, respectively in patients with left bundle branch block (LBBB), and no significant improvements in KCCQ among patients without LBBB. Although few responder analyses had been done previously, the magnitude of benefit (including numbers needed to treat) observed with dapagliflozin in the responder analyses of DAPA-HF also compare very favorably with previously observed results. Ekman, I. et al., *Eur Heart J* 32:2395-2404 (2011). It is noted that the numbers needed to treat for clinically meaningful improvements in KCCQ are based on comparisons of dapagliflozin-treated with placebo-treated patients (that also experienced an improvement in health status, consistent with a sizable "placebo effect", seen both in our study and in the DEFINE-HF trial). Therefore, the magnitude of dapagliflozin effects on the health status in clinical practice (where, obviously, no placebo is used) may be even greater than what we observed. Given the importance of reducing symptom burden and functional limitations and improving the quality of life—a key goal of HF management endorsed by the practice guidelines and regulators—our findings provide further support for dapagliflozin as a new treatment option for patients with HFrEF.

Conclusions

In the DAPA-HF trial, treatment with dapagliflozin reduced death and heart failure hospitalizations across the range of baseline KCCQ values, and improved symptom burden, functional status and quality of life in patients with HFrEF. Furthermore, dapagliflozin significantly increased the proportion of patients experiencing small, moderate and large improvements in health status; these effects were substantial and clinically important.

Example 3

DAPA-HF Phase III Clinical Trial Results—Effect of Dapagliflozin on Clinical, Metabolic, Hemodynamic, and Renal Outcomes in HF Patients with and without Diabetes Introduction In the DAPA-HF trial, discussed in Example 1, it was demonstrated that SGLT2 inhibition led to a similar reduction in the primary outcome of a worsening HF event or death from cardiovascular causes in HF patients with and without diabetes. See also McMurray, J. J. V. et al., *Eur J Heart Fail* 21: 665-675 (2019); McMurray, J. J. V. et al., *N Engl J Med* doi: 10.1056/NEJMoa1911303 [Epub ahead of print] (2019 Sep. 19), incorporated by reference in their entireties. In the prespecified analysis presented in this Example, the efficacy and safety of dapagliflozin, along with metabolic and hemodynamic changes is described, in patients with HF, across the range of baseline glycated hemoglobin (a.k.a. hemoglobin A1c or HbA1c) in DAPA-HF.

Methods

The eligibility requirements, baseline characteristics, and exclusion criterion of the DAPA-HF study patients were as described in Example 1 and in McMurray J. J. V. et al., *Eur J Heart Fail.*, doi: 10.1002/ejhf.1548. [Epub ahead of print] (2019 Jul. 15); McMurray, J. J. V. et al., *Eur J Heart Fail* 21: 665-675 (2019); McMurray, J. J. V. et al., *N Engl J Med*, doi: 10.1056/NEJMoa1911303 [Epub ahead of print] (2019 Sep. 19). Study procedures, study outcomes, and statistical analyses were also as described in Example 1 and McMurray, J. J. V. et al., *Eur J Heart Fail* 21: 665-675 (2019); McMurray, J. J. V. et al., *N Engl J Med*, doi: 10.1056/NEJMoa1911303 [Epub ahead of print] (2019 Sep. 19)).

Baseline Categorization of Diabetes Status

Investigators recorded whether patients had a history of diabetes at the enrollment visit (visit 1). Patients also had measurement of a glycated hemoglobin (HbA1c) level in a central laboratory at visit 1 and again at visit 2 (the randomization visit), which occurred 14 (±7) days later. For this prespecified subgroup analysis, patients were categorized as having diabetes if there was a history of diabetes or the glycated hemoglobin was at least 6.5% (≥48 mmol/mol) at both visits 1 and 2. Patients with a glycated hemoglobin level <5.7% (<39 mmol/ml) at both visits 1 and 2 were considered to have a normal glycated hemoglobin. For the purposes of this study, patients with a glycated hemoglobin ≥5.7% and <6.5% were considered to have pre-diabetes. Id.

Results

Patients

Glycemic Status at Baseline

Of the 4,744 patients included, 2605 (55%) did not have diabetes. Of the remainder, 1983 (41.8%) had a history of diabetes at screening and a further 156 (3.3%) were found to have previously undiagnosed diabetes i.e. a glycated hemoglobin of ≥6.5% at both visit 1 (enrolment) and visit 2 (randomization). Of the 2605 patients without diabetes, 1748 (67.1%) had a glycated hemoglobin level of ≥5.7% at either visit 1 or 2 and 839 patients (32.2%) had a glycated hemoglobin level <5.7% at both visits 1 and 2. In addition, 12 patients had only a single glycated hemoglobin measurement of <5.7% and 6 patients had both baseline glycated hemoglobin measurements missing (these 18 patients were included in normal glycated hemoglobin group).

Patient Characteristics According to Baseline Glycemic Status

The baseline characteristics of patients with and without diabetes are shown in Table 5 and these were well balanced between patients assigned to dapagliflozin or placebo within each patient group (Table 6). Patients without diabetes were less likely to be black and to have an ischemic etiology than participants with diabetes (Table 5). Mean body-mass index, heart rate, systolic blood pressure, and NT-proBNP level were lower in participants without diabetes, compared to those with diabetes. Mean eGFR was higher in participants without diabetes, compared to those with diabetes. The mean glycated hemoglobin level in patients without diabetes was 5.8%, compared with 7.4% in those with diabetes. The median duration of diabetes was 7.41 years (IQR 2.75, 13.5).

At baseline, both NYHA functional class and KCCQ-TSS were better in patients without diabetes, compared to those with diabetes.

TABLE 5

Characteristics of patients at baseline according to diabetes status*

| Characteristic | No T2DM (N = 2605) | T2DM¶ (N = 2139) | P-values |
|---|---|---|---|
| Age - yr | 66.2 ± 11.6 | 66.5 ± 9.9 | 0.32 |
| Sex - no (%) | | | 0.11 |
| Female | 632 (24.3) | 477 (22.3) | |
| Male | 1973 (75.7) | 1662 (77.7) | |
| Race - no. (%)† | | | 0.005 |
| White | 1844 (70.8) | 1489 (69.6) | |
| Black or African American | 98 (3.8) | 128 (6.0) | |
| Asian | 625 (24.0) | 491 (23.0) | |
| Other | 38 (1.5) | 31 (1.4) | |
| Region - no. (%) | | | 0.070 |
| North America | 342 (13.1) | 335 (15.7) | |
| South America | 443 (17.0) | 374 (17.5) | |
| Europe | 1203 (46.2) | 951 (44.5) | |
| Asia-Pacific | 617 (23.7) | 479 (22.4) | |
| NYHA functional classification - no. (%) | | | <0.001 |
| II | 1841 (70.7) | 1362 (63.7) | |

TABLE 5-continued

Characteristics of patients at baseline according to diabetes status*

| Characteristic | No T2DM (N = 2605) | T2DM¶ (N = 2139) | P-values |
|---|---|---|---|
| III | 743 (28.5) | 755 (35.3) | |
| IV | 21 (0.8) | 22 (1.0) | |
| Heart rate - beats/min | 70.9 ± 11.9 | 72.3 ± 11.3 | <0.001 |
| Systolic blood pressure - mm Hg | 120.6 ± 16.1 | 123.3 ± 16.5 | <0.001 |
| Left ventricular ejection fraction - % | 30.9 ± 6.9 | 31.2 ± 6.7 | 0.11 |
| HbA1c - % | 5.8 ± 0.4 | 7.4 ± 1.5 | <0.001 |
| Median NT-proBNP (IQR) - pg/ml | 1413 (828-2493) | 1484 (894-2818) | 0.002 |
| KCCQ-TSS | 75.2 (+20.6) | 71.7 (+22.9) | <0.001 |
| Body-mass index§ | 27.2 ± 5.7 | 29.3 ± 6.0 | <0.001 |
| Principal cause of heart failure - no. (%) | | | <0.001 |
| Ischemic | 1341 (51.5) | 1333 (62.3) | |
| Non-ischemic | 1033 (39.7) | 654 (30.6) | |
| Unknown | 231 (8.9) | 152 (7.1) | |
| Medical history - no. (%) | | | |
| Hospitalization for heart failure | 1202 (46.1) | 1049 (49.0) | 0.047 |
| Atrial fibrillation | 1022 (39.2) | 796 (37.2) | 0.15 |
| Estimated GFR - ml/min/1.73 m² of body-surface area | 67.8 ± 19.2 | 63.4 ± 19.4 | <0.001 |
| Estimated GFR rate < 60 ml/min/1.73 m² - no. (%) | 944 (36.3) | 982 (45.9) | <0.001 |
| Device therapy - no (%) | | | |
| Implantable cardioverter-defibrillator‡ | 665 (25.5) | 577 (27.0) | 0.26 |
| Cardiac-resynchronization therapy ** | 203 (7.8) | 151 (7.1) | 0.34 |
| Heart failure medication at randomization visit - no (%) | | | |
| Diuretic | 2405 (92.3) | 2028 (94.8) | <0.001 |
| ACE inhibitor | 1489 (57.2) | 1172 (54.8) | 0.10 |
| ARB | 692 (26.6) | 615 (28.8) | 0.093 |
| Sacubitril/valsartan | 279 (10.7) | 229 (10.7) | 1.00 |
| Beta-blocker | 2491 (95.6) | 2067 (96.6) | 0.074 |
| Mineralocorticoid receptor antagonist | 1841 (70.7) | 1529 (71.5) | 0.54 |
| Digitalis | 458 (17.6) | 429 (20.1) | 0.030 |
| Glucose-lowering medication at randomization visit - no (%) | | | |
| Biguanide | 10 (0.4) | 1020 (47.7) | <0.001 |
| Sulfonylurea | 0 (0.0) | 440 (20.6) | <0.001 |
| DPP-4 inhibitor | 0 (0.0) | 310 (14.5) | <0.001 |
| GLP-1 receptor agonist | 0 (0.0) | 21 (1.0) | <0.001 |
| Insulin | 0 (0.0) | 540 (25.2) | <0.001 |

T2DM = type 2 diabetes mellitus.
*Plus-minus values are means ±SD.
Percentages may not total 100 because of rounding.
ACE = angiotensin-converting enzyme, ARB = angiotensin-receptor blocker, DPP-4 = dipeptidyl peptidase 4, GFR = glomerular filtration rate, GLP-1 = glucagon-like peptide 1, IQR = interquartile range, LVEF = left ventricular ejection fraction, MRA = mineralocorticoid receptor antagonist, NT-proBNP = N-terminal pro-B-type natriuretic peptide, NYHA = New York Heart Association, KCCQ-TSS = Kansas City Cardiomyopathy Questionnaire total symptom score - ranges from 0 to 100, with higher scores indicating fewer symptoms and physical limitations associated with heart failure.
†Race was reported by the investigators.
§The body-mass index is the weight in kilograms divided by the square of the height in meters.
¶993 patients (41.8%) in the dapagliflozin group and 990 in the placebo group (41.8%) had a history of diabetes at baseline. An additional 82 patients in the dapagliflozin group and 74 in the placebo group had previously undiagnosed diabetes defined as a glycated hemoglobin level of 6.5% or greater (≥48 mmol/mol) measured in a central laboratory at both screening and randomization.
‡Either implantable cardioverter-defibrillator or cardiac resynchronization therapy with a defibrillator.
** Cardiac-resynchronization therapy with or without a defibrillator.

TABLE 6

Baseline characteristics by diabetes status and study drug allocation
No Diabetes (n = 2605)

| | Placebo N = 1,307 | Dapagliflozin N = 1,298 | p-value |
|---|---|---|---|
| Age - yr | 66.4 ± 11.5 | 66.0 ± 11.8 | 0.48 |
| Sex - no (%) | | | 0.41 |
| Female | 308 (23.6) | 324 (25.0) | |
| Male | 999 (76.4) | 974 (75.0) | |
| Race - no. (%)† | | | 1.00 |
| White | 926 (70.9) | 918 (70.7) | |
| Black or African American | 48 (3.7) | 50 (3.9) | |

TABLE 6-continued

Baseline characteristics by diabetes status and study drug allocation
No Diabetes (n = 2605)

|  | Placebo<br>N = 1,307 | Dapagliflozin<br>N = 1,298 | p-value |
|---|---|---|---|
| Asian | 314 (24.0) | 311 (24.0) |  |
| Other | 19 (1.5) | 19 (1.5) |  |
| Region - no. (%) |  |  | 0.96 |
| North America | 168 (12.9) | 174 (13.4) |  |
| South America | 226 (17.3) | 217 (16.7) |  |
| Europe | 602 (46.1) | 601 (46.3) |  |
| Asia/Pacific | 311 (23.8) | 306 (23.6) |  |
| NYHA functional classification - no. (%) |  |  | 0.14 |
| II | 903 (69.1) | 938 (72.3) |  |
| III | 391 (29.9) | 352 (27.1) |  |
| IV | 13 (1.0) | 8 (0.6) |  |
| Heart rate - beats/min | 70.9 ± 12.0 | 70.8 ± 11.9 | 0.73 |
| Systolic Blood Pressure - mmHg | 120.1 ± 15.7 | 121.1 ± 16.4 | 0.11 |
| Left ventricular ejection fraction - % | 30.8 ± 6.9 | 31.0 ± 6.8 | 0.40 |
| HbA1c - % | 5.8 ± 0.4 | 5.7 ± 0.4 | 0.07 |
| Median NT-proBNP (IQR) - pg/ml | 1412 (840-2551) | 1414 (821-2424) | 0.49 |
| KCCQ-TSS | 75.8 ± 20.0 | 74.6 ± 21.2 | 0.18 |
| Body-mass index§ | 27.1 ± 5.6 | 27.3 ± 5.9 | 0.40 |
| Principal cause of heart failure - no. (%) |  |  | 0.53 |
| Ischemic | 681 (52.1) | 660 (50.8) |  |
| Non-ischemic | 518 (39.6) | 515 (39.7) |  |
| Unknown | 108 (8.3) | 123 (9.5) |  |
| Medical history - no. (%) |  |  |  |
| Hospitalization for heart failure | 594 (45.4) | 608 (46.8) | 0.48 |
| Atrial fibrillation | 515 (39.4) | 507 (39.1) | 0.86 |
| Estimated GFR - ml/min/1.73 m2 of body-surface area | 67.8 ± 19.1 | 67.8 ± 19.3 | 0.97 |
| Estimated GFR rate < 60 ml/min/1.73 m2 - no. (%) | 464 (35.5) | 480 (37.0) | 0.43 |
| Device therapy - no (%) |  |  |  |
| Implantable cardioverter-defibrillator‡ | 318 (24.3) | 347 (26.7) | 0.16 |
| Cardiac-resynchronization therapy ** | 93 (7.1) | 110 (8.5) | 0.20 |
| Heart failure medication at randomization visit - no (%) |  |  |  |
| Diuretic | 1,214 (92.9) | 1,191 (91.8) | 0.28 |
| ACE inhibitor | 752 (57.5) | 737 (56.8) | 0.70 |
| ARB | 335 (25.6) | 357 (27.5) | 0.28 |
| Sacubitril/valsartan | 141 (10.8) | 138 (10.6) | 0.90 |
| Beta-blocker | 1,251 (95.7) | 1,240 (95.5) | 0.82 |
| Mineralocorticoid receptor antagonist | 928 (71.0) | 913 (70.3) | 0.71 |
| Digitalis | 234 (17.9) | 224 (17.3) | 0.66 |
| Glucose-lowering medication at randomization visit - no (%) |  |  |  |
| Biguanide | 6 (0.5) | 4 (0.3) | 0.53 |

| Diabetes (n = 2139) | Placebo<br>N = 1,064 | Dapagliflozin<br>N = 1,075 | p-value |
|---|---|---|---|
| Age - yr | 66.7 ± 9.8 | 66.3 ± 9.9 | 0.42 |
| Sex - no (%) |  |  | 0.98 |
| Female | 237 (22.3) | 240 (22.3) |  |
| Male | 827 (77.7) | 835 (77.7) |  |
| Race - no. (%)† |  |  | 0.50 |
| White | 745 (70.1) | 744 (69.2) |  |
| Black or African American | 56 (5.3) | 72 (6.7) |  |
| Asian | 250 (23.5) | 241 (22.4) |  |
| Other | 13 (1.2) | 18 (1.7) |  |
| Region - no. (%) |  |  | 0.40 |
| North America | 242 (22.7) | 237 (22.0) |  |
| South America | 458 (43.0) | 493 (45.9) |  |
| Europe | 174 (16.4) | 161 (15.0) |  |
| Asia/Pacific | 190 (17.9) | 184 (17.1) |  |
| NYHA functional classification - no. (%) |  |  | 0.33 |
| II | 694 (65.2) | 668 (62.1) |  |
| III | 360 (33.8) | 395 (36.7) |  |
| IV | 10 (0.9) | 12 (1.1) |  |
| Heart rate - beats/min | 72.3 ± 11.4 | 72.3 ± 11.3 | 0.88 |
| Systolic Blood Pressure - mmHg | 123.4 ± 16.9 | 123.2 ± 16.1 | 0.73 |
| Left ventricular ejection fraction - % | 31.0 ± 6.8 | 31.4 ± 6.6 | 0.20 |
| HbA1c - % | 7.4 ± 1.6 | 7.4 ± 1.5 | 0.55 |
| Median NT-proBNP (IQR) - pg/ml | 1487 (889-2759) | 1479 (903-2885) | 0.82 |
| KCCQ-TSS | 72.1 ± 22.6 | 71.4 ± 23.2 | 0.49 |
| Body-mass index§ | 29.4 ± 6.1 | 29.3 ± 5.9 | 0.58 |

TABLE 6-continued

Baseline characteristics by diabetes status and study drug allocation

No Diabetes (n = 2605)

|  | Placebo<br>N = 1,307 | Dapagliflozin<br>N = 1,298 | p-value |
| --- | --- | --- | --- |
| Principal cause of heart failure - no. (%) |  |  | 0.43 |
| Ischemic | 677 (63.6) | 656 (61.0) |  |
| Non-ischemic | 312 (29.3) | 342 (31.8) |  |
| Unknown | 75 (7.0) | 77 (7.2) |  |
| Medical history - no. (%) |  |  |  |
| Hospitalization for heart failure | 533 (50.1) | 516 (48.0) | 0.33 |
| Atrial fibrillation | 387 (36.4) | 409 (38.0) | 0.42 |
| Estimated GFR - ml/min/1.73 m2 of body-surface area | 62.8 ± 19.1 | 63.9 ± 19.6 | 0.21 |
| Estimated GFR rate < 60 ml/min/1.73 m2 - no. (%) | 500 (47.0) | 482 (44.8) | 0.32 |
| Device therapy - no (%) |  |  |  |
| Implantable cardioverter-defibrillator‡ | 302 (28.4) | 275 (25.6) | 0.14 |
| Cardiac-resynchronization therapy** | 71 (6.7) | 80 (7.4) | 0.49 |
| Heart failure medication at randomization visit - no (%) |  |  |  |
| Diuretic | 1,003 (94.3) | 1,025 (95.3) | 0.26 |
| ACE inhibitor | 577 (54.2) | 595 (55.3) | 0.60 |
| ARB | 297 (27.9) | 318 (29.6) | 0.39 |
| Sacubitril/valsartan | 117 (11.0) | 112 (10.4) | 0.67 |
| Beta-blocker | 1,029 (96.7) | 1,038 (96.6) | 0.85 |
| Mineralocorticoid receptor antagonist | 746 (70.1) | 783 (72.8) | 0.16 |
| Digitalis | 208 (19.5) | 221 (20.6) | 0.56 |
| Glucose-lowering medication at randomization visit - no (%) |  |  |  |
| Biguanide | 515 (48.4) | 505 (47.0) | 0.51 |
| Sulfonylurea | 211 (19.8) | 229 (21.3) | 0.40 |
| DPP-4 inhibitor | 149 (14.0) | 161 (15.0) | 0.52 |
| GLP-1 receptor agonist | 10 (0.9) | 11 (1.0) | 0.84 |
| Insulin | 266 (25.0) | 274 (25.5) | 0.79 |

*Plus-minus values are means +SD.

Percentages may not total 100 because of rounding.

ACE = angiotensin-converting enzyme, ARB = angiotensin-receptor blocker, DPP-4 = dipeptidyl peptidase 4, GFR = glomerular filtration rate, GLP-1 = glucagon-like peptide 1, IQR = interquartile range, LVEF = left ventricular ejection fraction, MRA = mineralocorticoid receptor antagonist, NT-proBNP = N-terminal pro-B-type natriuretic peptide, NYHA = New York Heart Association, KCCQ-TSS = Kansas City Cardiomyopathy Questionnaire total symptom score - ranges from 0 to 100, with higher scores indicating fewer symptoms and physical limitations associated with heart failure.

†Race was reported by the investigators.

§The body-mass index is the weight in kilograms divided by the square of the height in meters.

¶993 patients (41.8%) in the dapagliflozin group and 990 in the placebo group (41.8%) had a history of diabetes at baseline. An additional 82 patients in the dapagliflozin group and 74 in the placebo group had previously undiagnosed diabetes defined as a glycated hemoglobin level of 6.5% or greater (≥48 mmol/mol) measured in a central laboratory at both screening and randomization.

‡Either implantable cardioverter-defibrillator or cardiac resynchronization therapy with a defibrillator.

**Cardiac-resynchronization therapy with or without a defibrillator.

Outcomes
Outcomes According to Baseline Glycemic Status

Figure 10A:
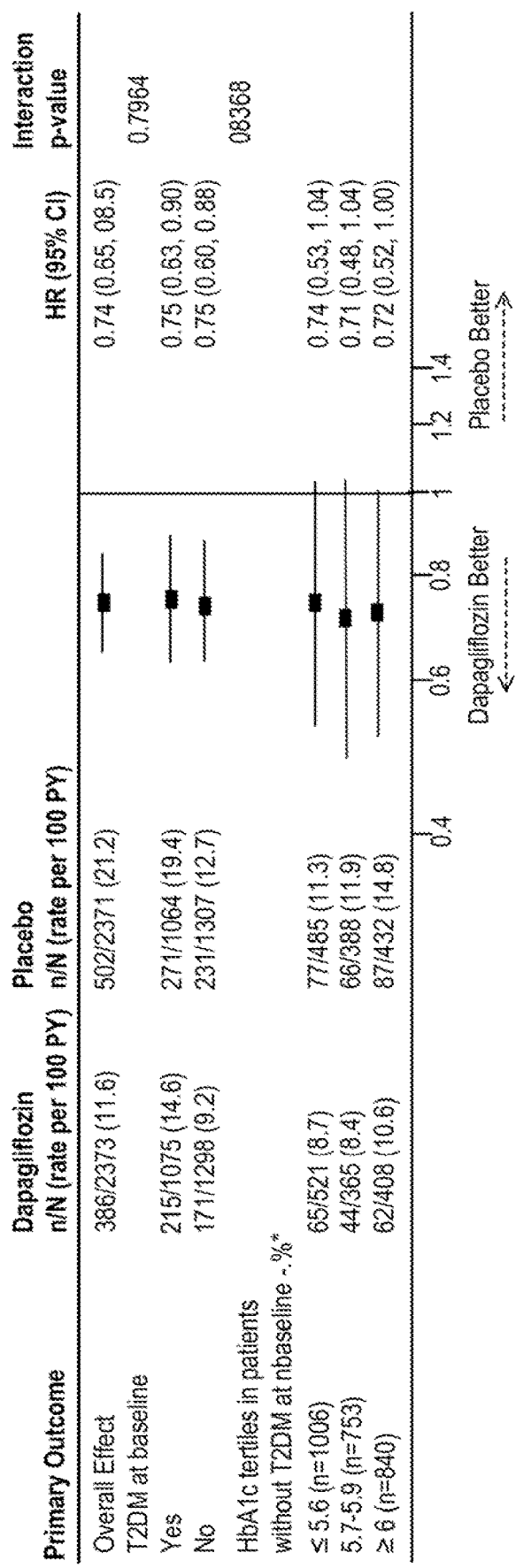
FIGS. 10A-10B depict the effect of dapagliflozin, compared with placebo, on the prespecified primary composite outcome in patients with and without diabetes and according to glycated hemoglobin level in patients without diabetes at baseline (FIG. 10A) and the effect of dapagliflozin, compared with placebo, on the prespecified primary and secondary composite outcomes, their components and all-cause mortality, according to diabetes status at baseline.
Figure 14:
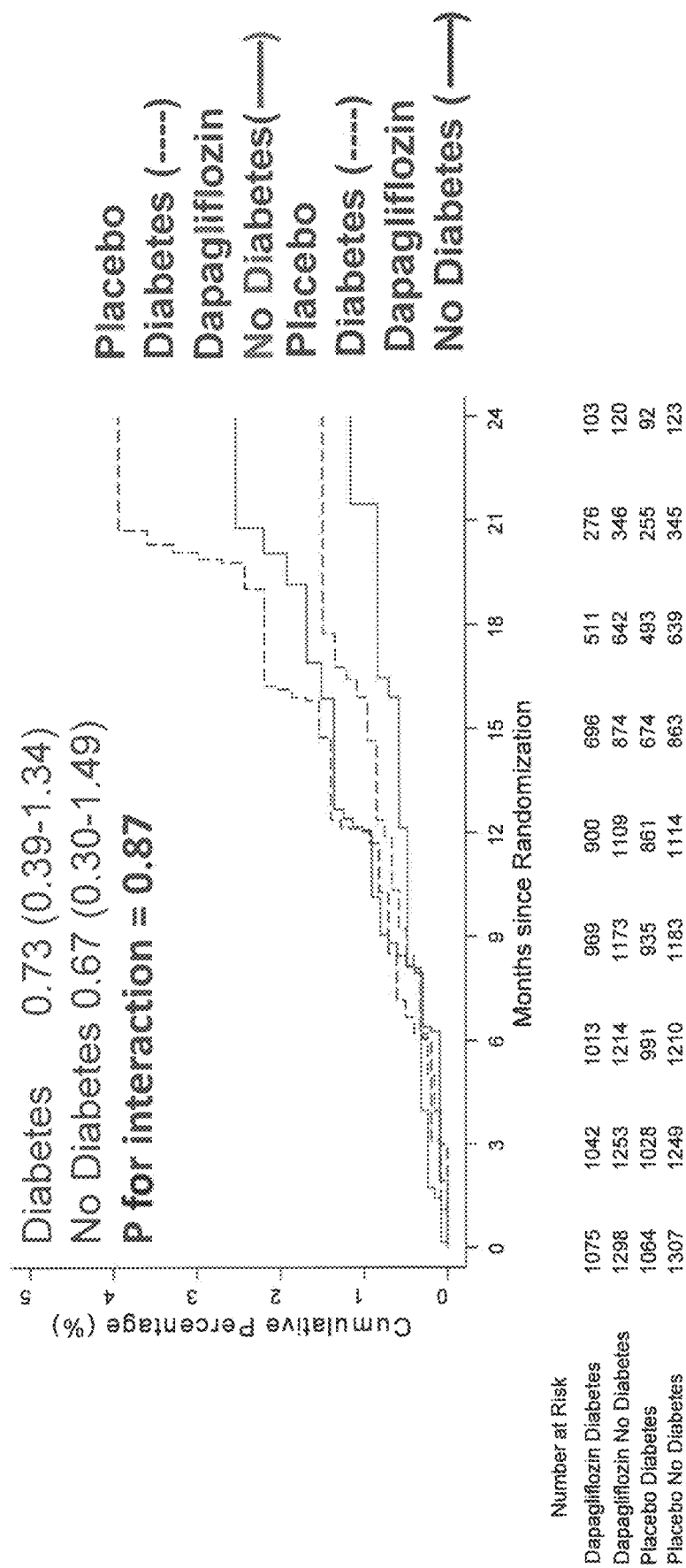
FIG. 14 describes renal composite outcome by diabetes status (includes 82 dapagliflozin and 74 placebo patients with previously undiagnosable diabetes; i.e., two HbA1c ≥6.5% (≥48 mmol/mol) consisting of a 50% or greater sustained decline in eGFR, end-stage renal disease (defined as a sustained eGFR <15 mL/min/1.73 m$^2$) or chronic dialysis or renal transplant FIG. 15 illustrates a sustained decline in eGFR per ml/min/1.73 m$^2$ over time in dapagliflozin patients compared to placebo patients FIG. 16 describes in eGFR per ml/min/1.73 m$^2$ per year by diabetes status at baseline (includes 82 dapagliflozin and 74 placebo patients with previously undiagnosed diabetes, i.e., HbA1c ≥6.5% (≥48 mmol/mol))

Patients without diabetes had lower rates of the prespecified mortality and worsening HF outcomes (Table 7, FIGS. 9A-9D, and FIG. 10A). Among participants without diabetes, the rate of the primary endpoint was highest in those who we're in the top third of baseline glycated hemoglobin (≥6.0%) i.e., individuals with prediabetes (FIG. 10A). The risk of the renal composite endpoint was also lower in participants without diabetes (FIG. 14). By contrast, the overall change from baseline in the KCCQ-TSS did not differ between participants with or without diabetes.

TABLE 7

Prespecified Efficacy Outcomes

| | Dapagliflozin (N = 2373) No T2DM (N = 1298) T2DM (N = 1075) | | Placebo (N = 2371) No T2DM (N = 1307) T2DM (N = 1064) | | | | |
|---|---|---|---|---|---|---|---|
| Variable | No. (%) | Subjects with Event/100 Patient-Yr | No. (%) | Subjects with Event/100 Patient-Yr | Hazard Ratio (95% CI) | P-value | Interaction P-value |
| Efficacy Outcomes | | | | | | | |
| Primary composite outcome* | | | | | | | |
| No T2DM | 171 (13.2) | 9.2 | 231 (17.7) | 12.7 | 0.73 (0.60 to 0.88) | 0.0015 | 0.796 |
| T2DM | 215 (20.0) | 14.6 | 271 (25.5) | 19.4 | 0.75 (0.63 to 0.90) | 0.0018 | |
| Hospitalization for heart failure or an urgent heart failure visit | | | | | | | |
| No T2DM | 95 (7.3) | 5.1 | 150 (11.5) | 8.2 | 0.62 (0.48-0.80) | 0.0003 | 0.225 |
| T2DM | 142 (13.2) | 9.6 | 176 (16.5) | 12.6 | 0.77 (0.61-0.95) | 0.018 | |
| Hospitalization for heart failure | | | | | | | |
| No T2DM | 93 (7.2) | 5.0 | 146 (11.2) | 8.0 | 0.63 (0.48-0.81) | 0.0004 | 0.262 |
| T2DM | 138 (12.8) | 9.3 | 172 (16.2) | 12.2 | 0.76 (0.61-0.95) | 0.017 | |
| Urgent heart failure visit | | | | | | | |
| No T2DM | 3 (0.2) | 0.2 | 12 (0.9) | 0.6 | 0.25 (0.07-0.89) | 0.0318 | 0.250 |
| T2DM | 7 (0.7) | 0.4 | 11 (1.0) | 0.7 | 0.62 (0.24-1.59) | 0.316 | |
| Cardiovascular death | | | | | | | |
| No T2DM | 106 (8.2) | 5.5 | 125 (9.6) | 6.5 | 0.85 (0.66-1.10) | 0.23 | 0.700 |
| T2DM | 121 (11.3) | 7.7 | 148 (13.9) | 9.7 | 0.79 (0.63-1.01) | 0.06 | |
| Secondary outcomes | | | | | | | |
| Cardiovascular death or hospitalization for heart failure | | | | | | | |
| No T2DM | 169 (13.0) | 9.1 | 227 (17.4) | 12.4 | 0.73 (0.60-0.89) | 0.0022 | 0.833 |
| T2DM | 213 (19.8) | 14.4 | 268 (25.2) | 19.1 | 0.75 (0.63-0.90) | 0.0021 | |
| Total number of (first and recurrent) heart failure hospitalizations and cardiovascular death‡ | | | | | | | |
| No T2DM | 239 | | 327 | | 0.73 (0.59, 0.91) | 0.0053 | 0.7403 |
| T2DM | 328 | | 415 | | 0.77 (0.63, 0.94) | 0.0109 | |
| Change in KCCQ total symptom score at 8 mo.† | | | | | | | |
| No T2DM | 5.4 ± 17.7 | | 3.1 ± 17.9 | | 1.15 (1.05, 1.26) | 0.0040 | 0.176 |
| T2DM | 7.0 ± 19.7 | | 3.5 ± 20.8 | | 1.22 (1.11, 1.35) | 0.0001 | |
| Worsening renal function†† | | | | | | | |
| No T2DM | 10 (0.8) | 0.5 | 15 (1.2) | 0.8 | 0.67 (0.30-1.49) | 0.329 | 0.858 |
| T2DM | 18 (1.7) | 1.2 | 24 (2.3) | 1.6 | 0.73 (0.39-1.34) | 0.308 | |
| Death from any cause | | | | | | | |
| No T2DM | 133 (10.3) | 6.9 | 151 (11.6) | 7.8 | 0.88 (0.70-1.12) | 0.301 | 0.446 |
| T2DM | 143 (13.3) | 9.1 | 178 (16.7) | 11.7 | 0.78 (0.63-0.97) | 0.027 | |

T2DM = type 2 diabetes mellitus.
NA denotes not applicable because P values are not reported for outcomes with 10 events or fewer.
*Primary composite outcome - analyzed as time-to-first occurrence of urgent heart failure visit, hospitalization for heart failure or death from cardiovascular causes.
‡Total number of (first and recurrent) heart failure hospitalizations and cardiovascular death analyzed by the semi-parametric proportional rates model (Lin et al., 2000[16]; known as the LWYY method) - the treatment effect is a rate ratio.
†Scores on the Kansas City Cardiomyopathy Questionnaire (KCCQ) total symptom score range from 0 to 100, with higher scores indicating fewer symptoms and physical limitations associated with heart failure. The treatment effect is shown as a win-ratio. A value greater than 1 indicates superiority.
††Worsening renal function - composite outcome analyzed as time-to-first occurrence of 50% or greater reduction in eGFR sustained for at least 28 days, end-stage renal disease (ESRD) or death from renal causes. ESRD consisted of eGFR below 15 ml/min/1.73 m$^2$ sustained for at least 28 days, chronic dialysis treatment (sustained for at least 28 days) or kidney transplantation. Acute kidney injury serious adverse events: dapagliflozin 20 (0.8%) and placebo 41 (1.7%), p = 0.007.

Effect of Dapagliflozin Versus Placebo According to Baseline Glycemic Status

Figure 10B:
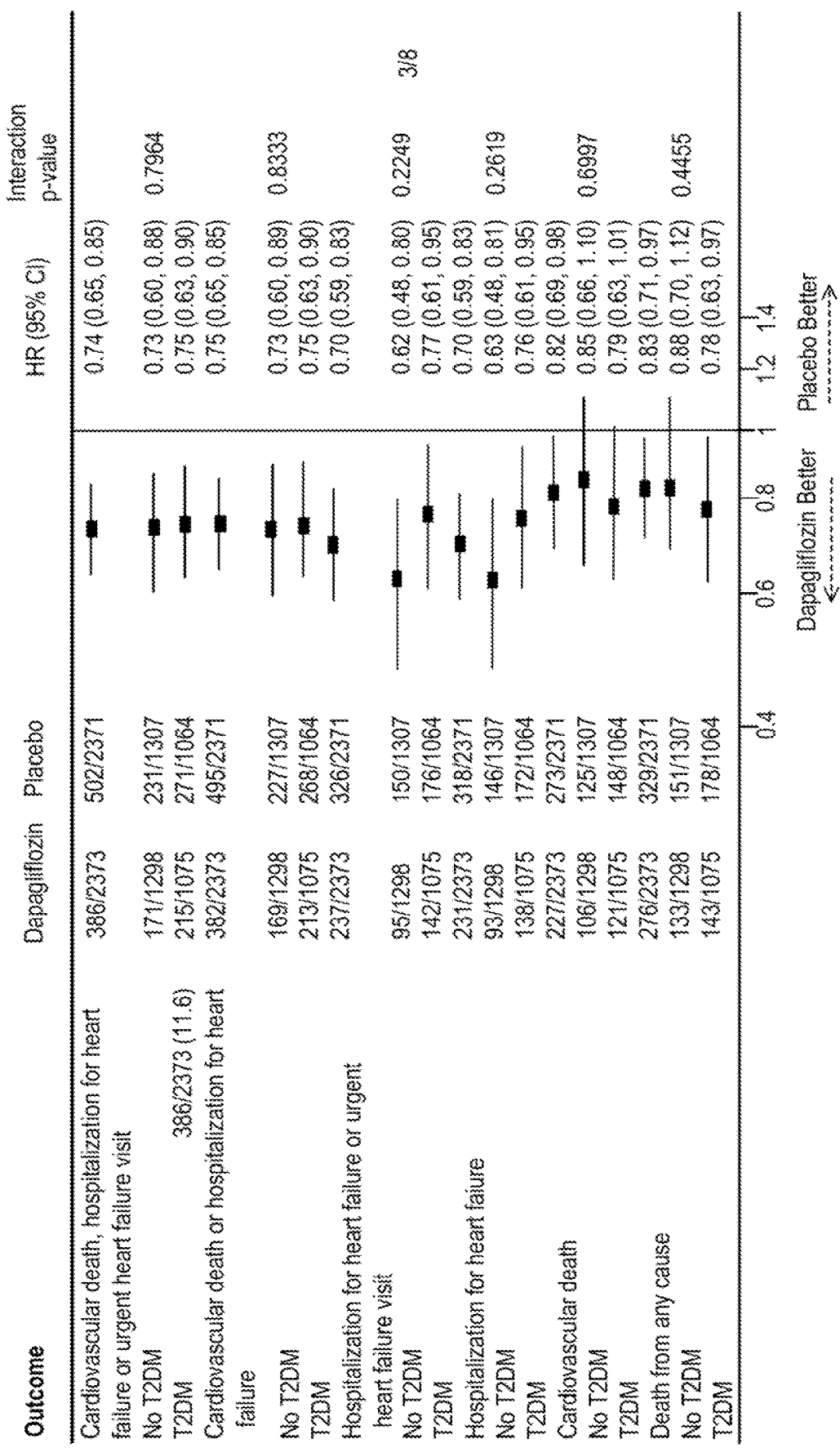

The effect of dapagliflozin on the primary composite outcome, and each of the individual mortality and hospital admission outcomes, as well as urgent visits for worsening heart failure requiring intravenous treatment, is shown in Table 7 and FIG. 10B. The effect of dapagliflozin on each outcome was similar in patients with and without diabetes, as was the effect of study drug on the renal composite outcome.

Among patients without diabetes at baseline, when divided into three equal groups, the effect of dapagliflozin on the primary outcome was consistent across the range of glycated hemoglobin (FIG. 10A). Specifically, for those in the lowest third (glycated hemoglobin level ≤5.6%), the dapagliflozin versus placebo hazard ratio was 0.74 (95% CI 0.53, 1.04) compared with 0.71 (0.48, 1.04) in the middle third (>5.6-<6.0%) and 0.72 (0.52, 1.00) in those in the highest third (≥6.0%); P interaction=0.837. Additional analyses using glycated hemoglobin as a continuous variable demonstrated benefit of dapagliflozin across the range included (FIGS. 12A-12D).

Between baseline and 8 months, the KCCQ-TSS increased by 2.2 (95% CI 0.7-3.7) points more with dapagliflozin, compared to placebo, in patients without diabetes and by 3.5 (95% CI 1.6-5.4) points more in patients with diabetes; P interaction=0.176 (Table 7).

In individuals without diabetes, more patients in the dapagliflozin group than in the placebo group self-reported an increase of at least 5 points (the minimally important difference) in KCCQ-TSS (57.7% vs. 51.7%; odds ratio 1.12 (95% CI 1.03, 1.22) and fewer reported a significant deterioration (26.0% vs. 31.3%; odds ratio 0.88 (0.81, 0.97); P<0.01 for both comparisons. The corresponding proportions in individuals with diabetes were: ≥5-point improvement—58.9% versus 49.9% odds ratio 1.20 (1.09, 1.31); and deterioration 24.5% versus 34.8% odds ratio, 0.78 (0.71, 0.87); P<0.001 for both comparisons (P interaction for improvement=0.294 and P interaction for deterioration=0.075).

Figure 17:
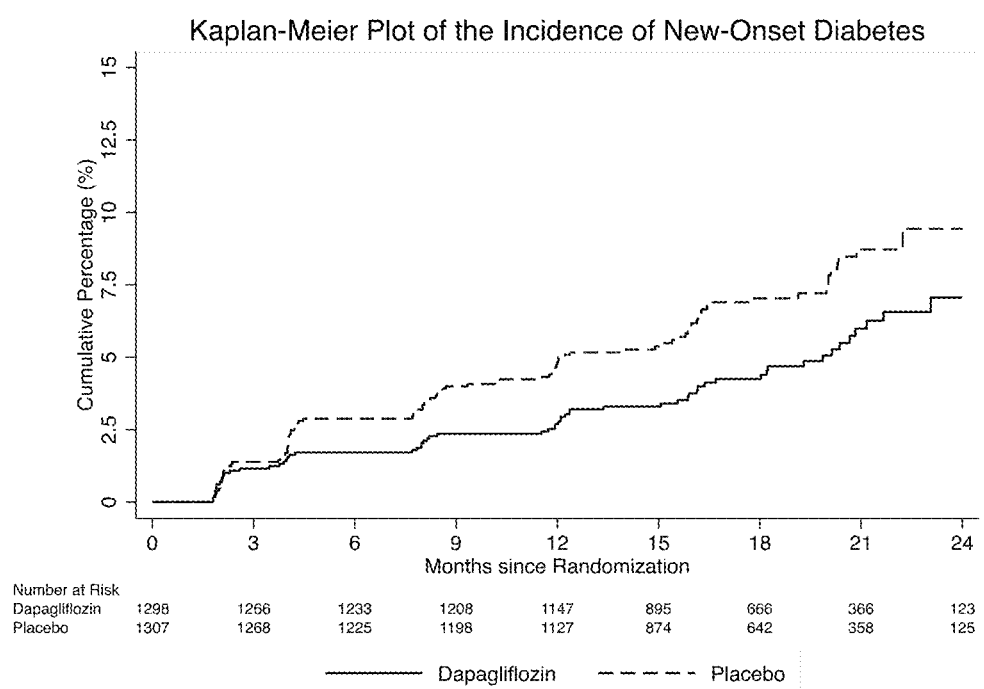
FIG. 17 describes incidence of new onset T2D (HbA1c ≥6.5%) measured at 2 consecutive study visits post-randomization or investigator-reported new T2D vs placebo patients with previously undiagnosed diabetes, i.e., HbA1c ≥6.5%

In individuals without diabetes, 157 developed T2D on trial, 150 (95.5%) of whom had prediabetes (A1c 5.7-6.4%) (136 [86.6%] using the more restrictive 6.0-6.4% criterion.) Those with incident T2D had a higher mean baseline A1c (6.2±0.3 vs 5.7±0.4%; p<0.001), greater BMI (28.5±5.9 vs 27.1±5.7 kg/m$^2$; p=0.003), and lower eGFR (61.5±17.4 vs 68.2±19.3 ml/min/1.73 m$^2$; p<0.001) than those who remained non-diabetic. Dapagliflozin reduced new-onset diabetes by 32%: placebo 93/1307 (7.1%) vs. dapagliflozin 64/1298 (4.9%); HR 0.68 (95% CI, 0.50-0.94; p=0.019) (Cox.) (FIG. 17).

Laboratory Measures, Weight, and Blood Pressure

Figure 11A:
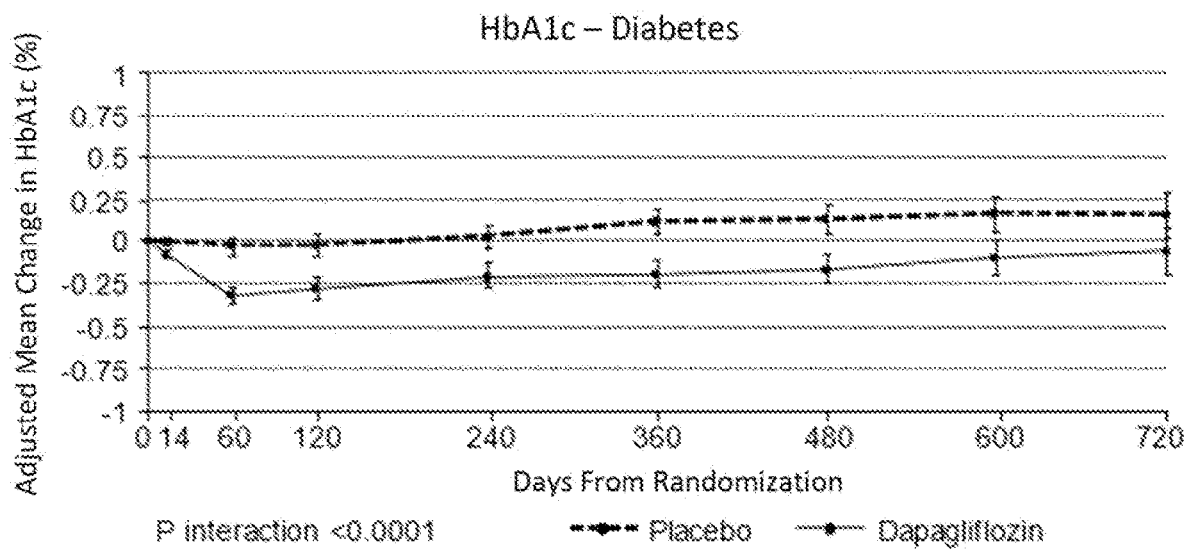
FIGS. 11A-11J are graphs depicting the effects of dapagliflozin, compared with placebo, on laboratory measures, weight, and systolic blood pressure, according to diabetes status (i.e., diabetes or no diabetes) at baseline. Changes from baseline are shown in glycated hemoglobin concentration (%) (HbA1c) (FIGS. 11A-11B); Weight (FIGS. 11C-11D); Systolic blood pressure (FIGS. 11E-11F); Hematocrit (FIGS. 11G-11H); and Creatinine (FIGS. 11I-11J). Least square mean changes along with 95% confidence internal (CI) are shown. The changes are adjusted for baseline values. *History of diabetes (n=1983) and glycated hemoglobin ≥6.5% at baseline (n=156).
Figure 11B:
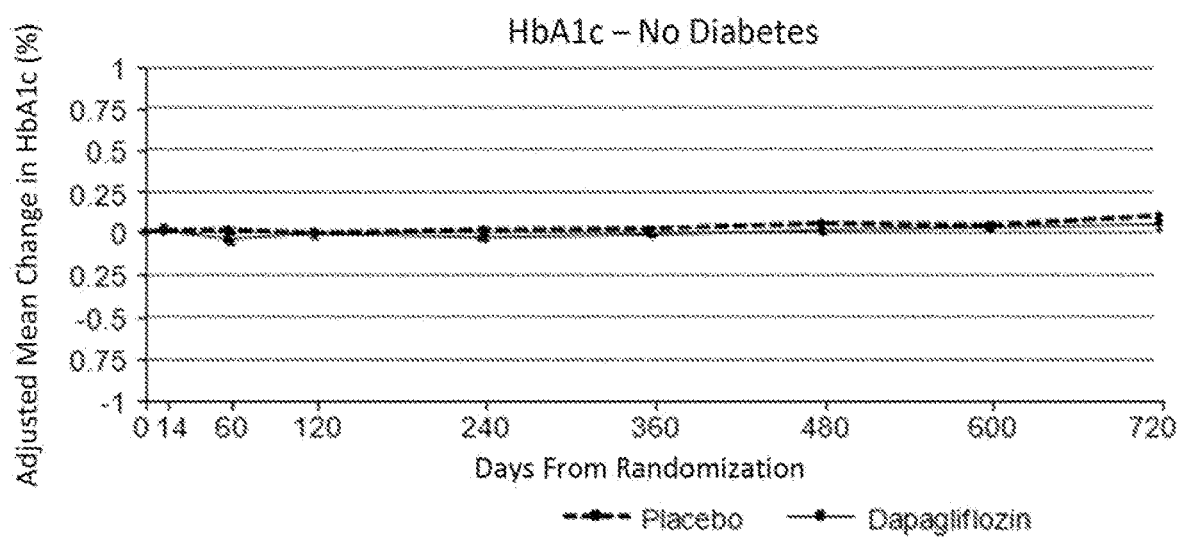
Figure 11C:
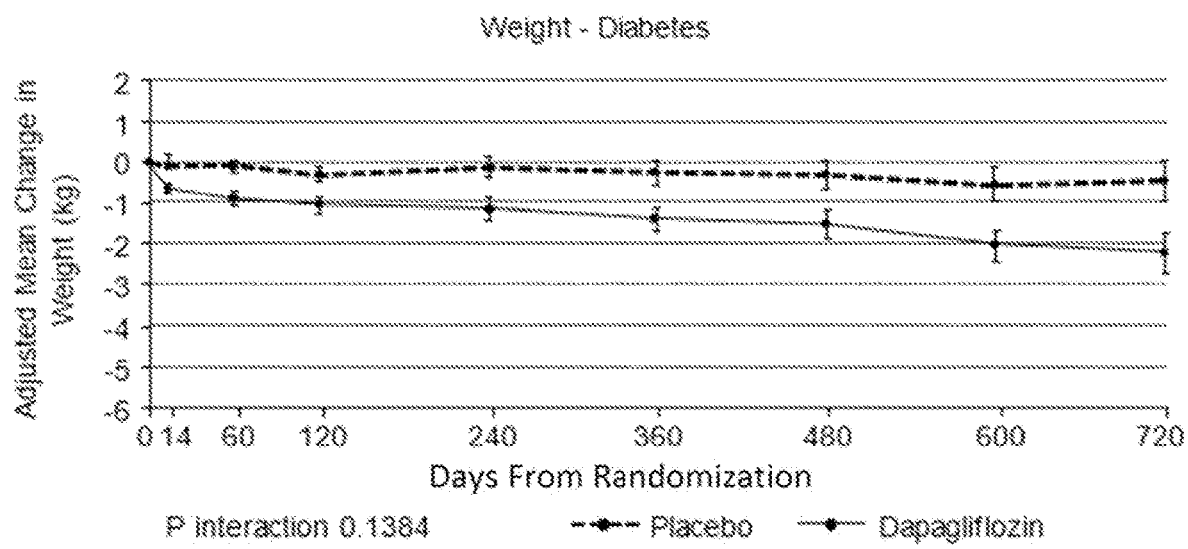
Figure 11D:
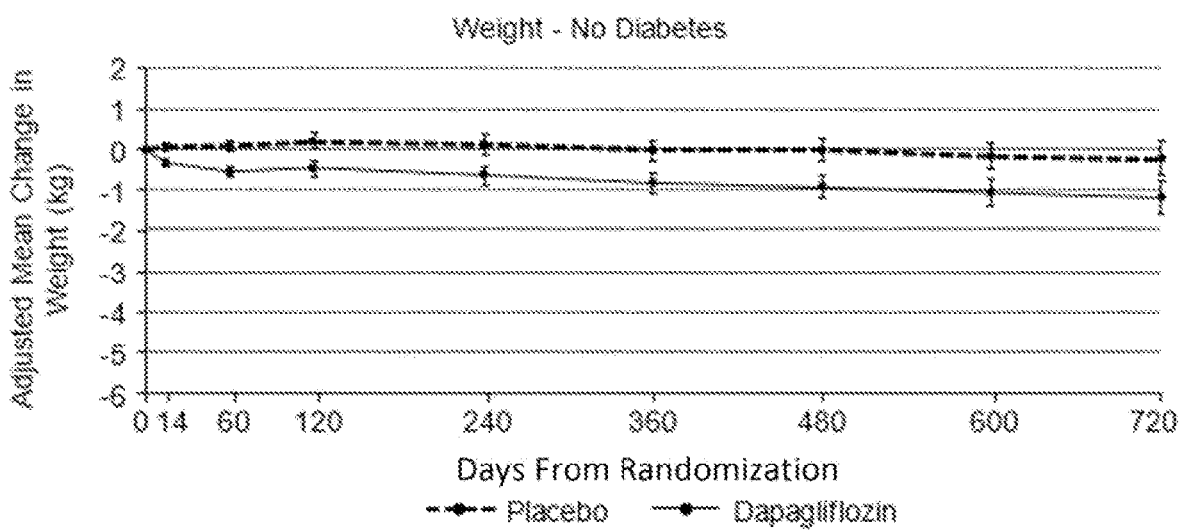
Figure 11E:
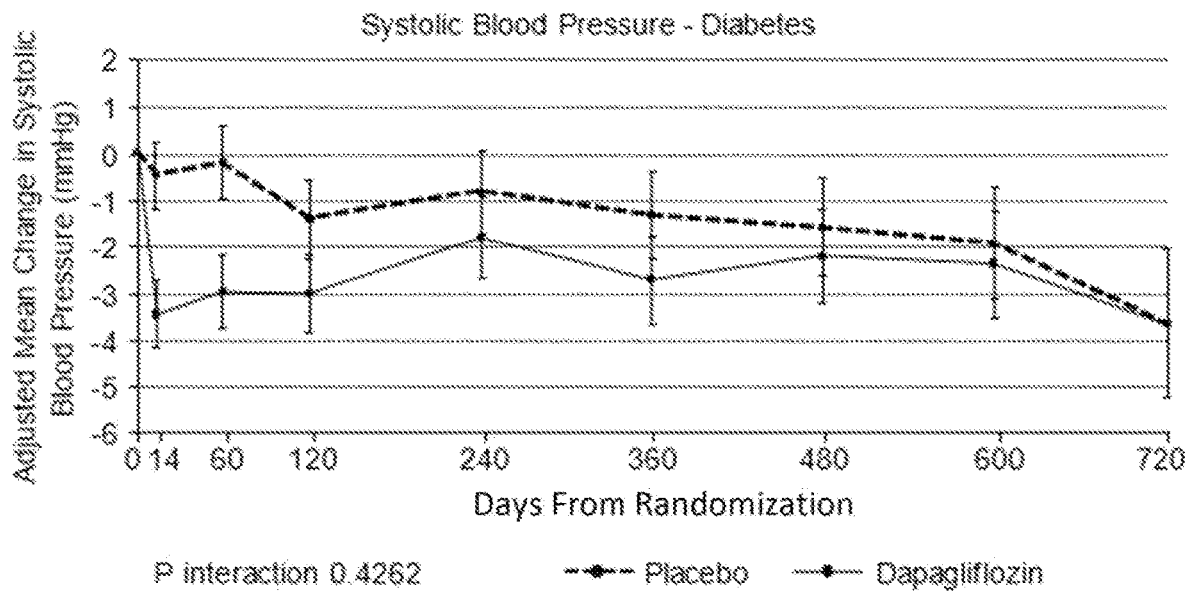
Figure 11F:
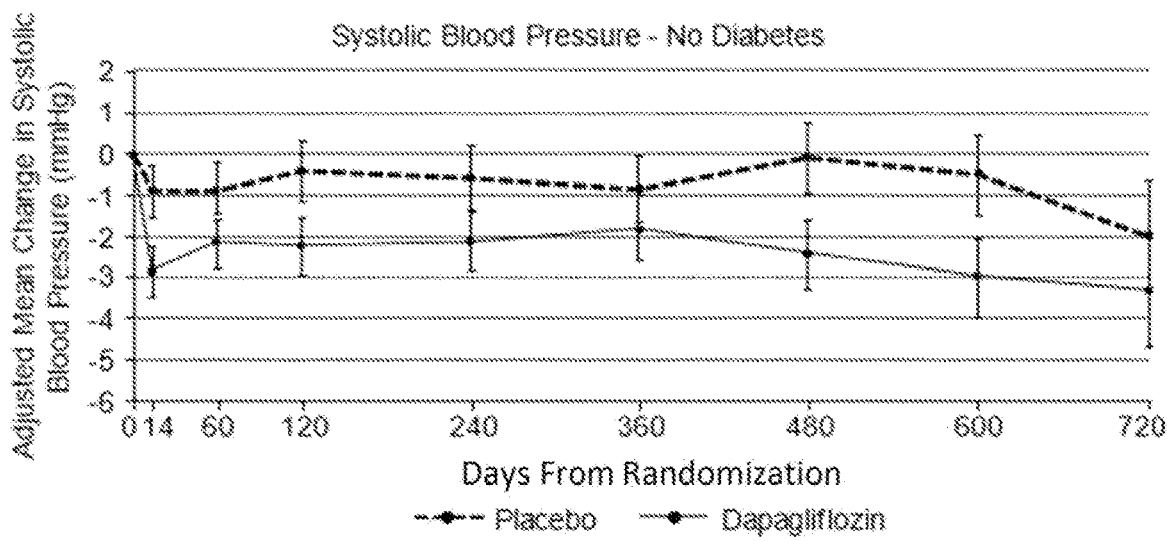
Figure 11G:
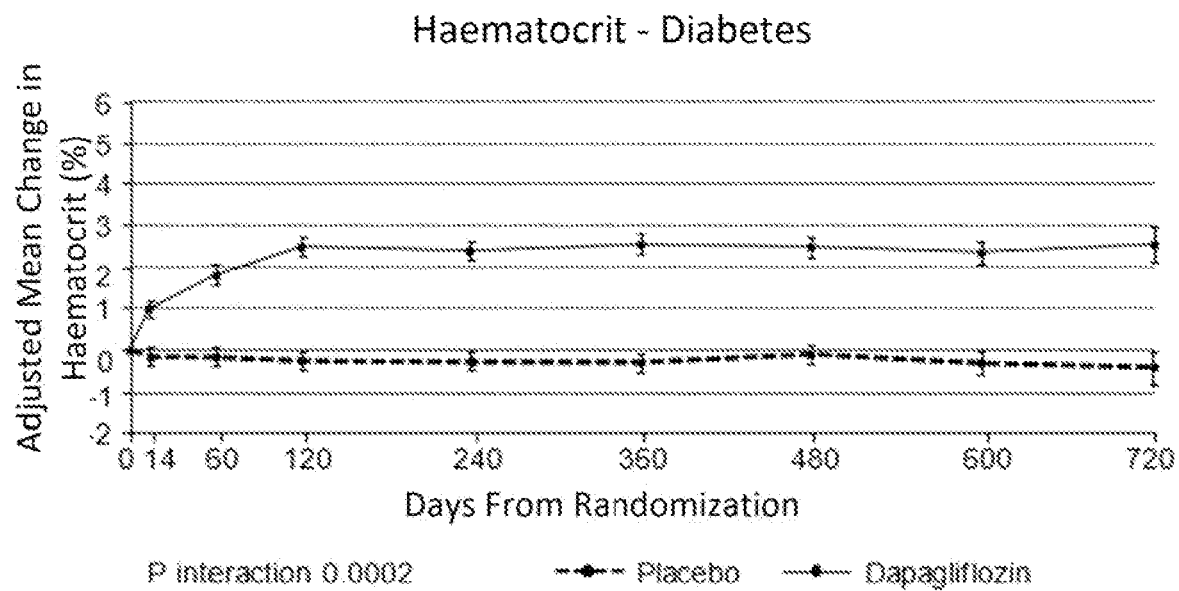
Figure 11H:
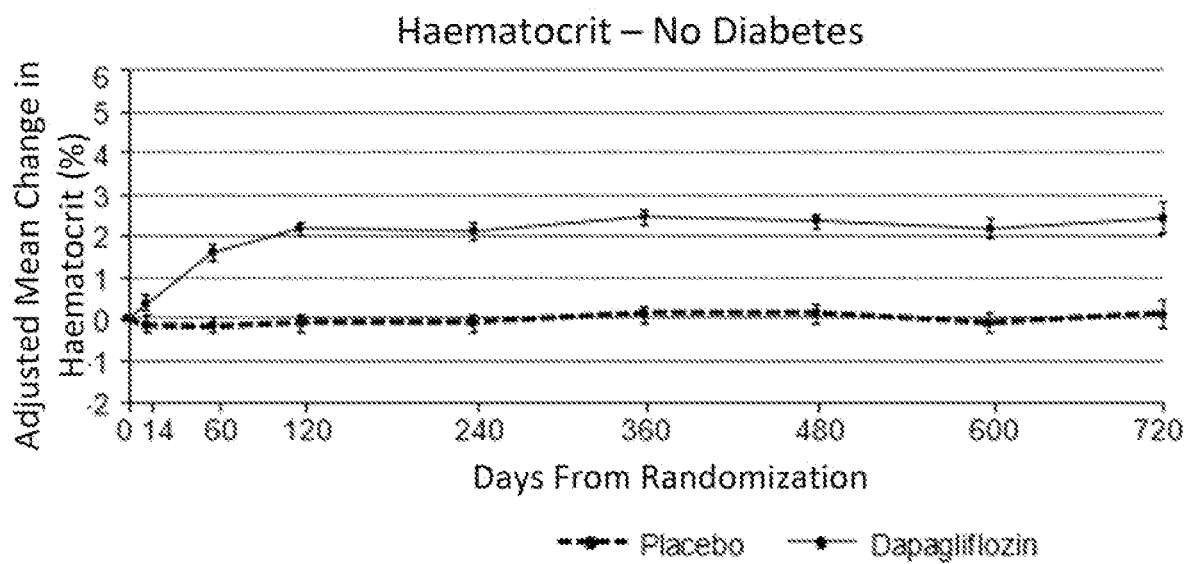
Figure 11I:
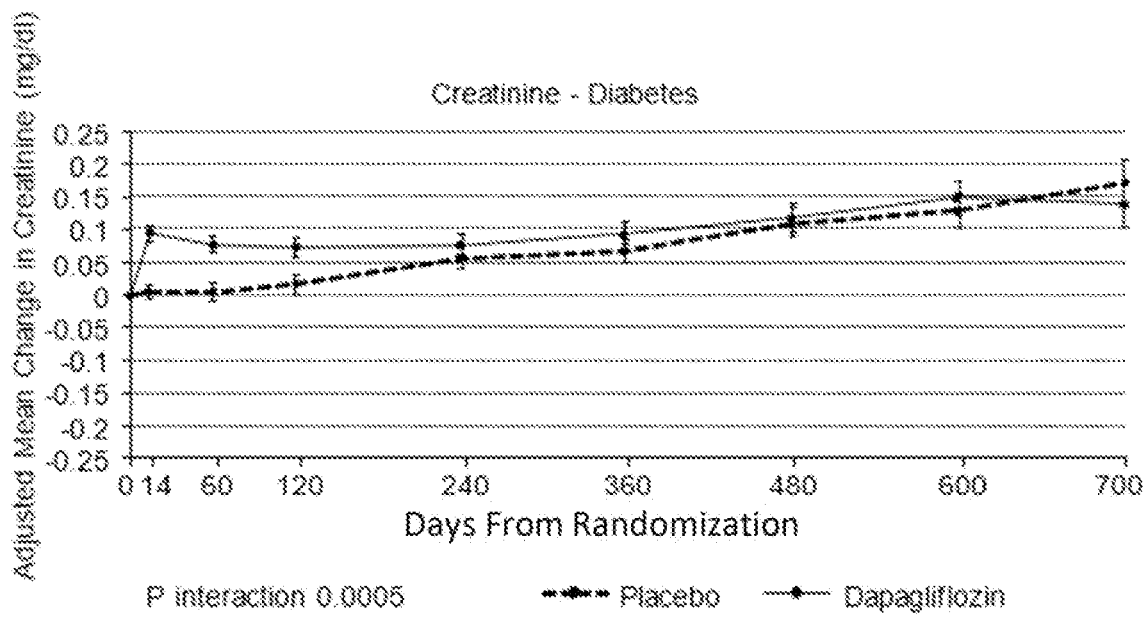
Figure 11J:
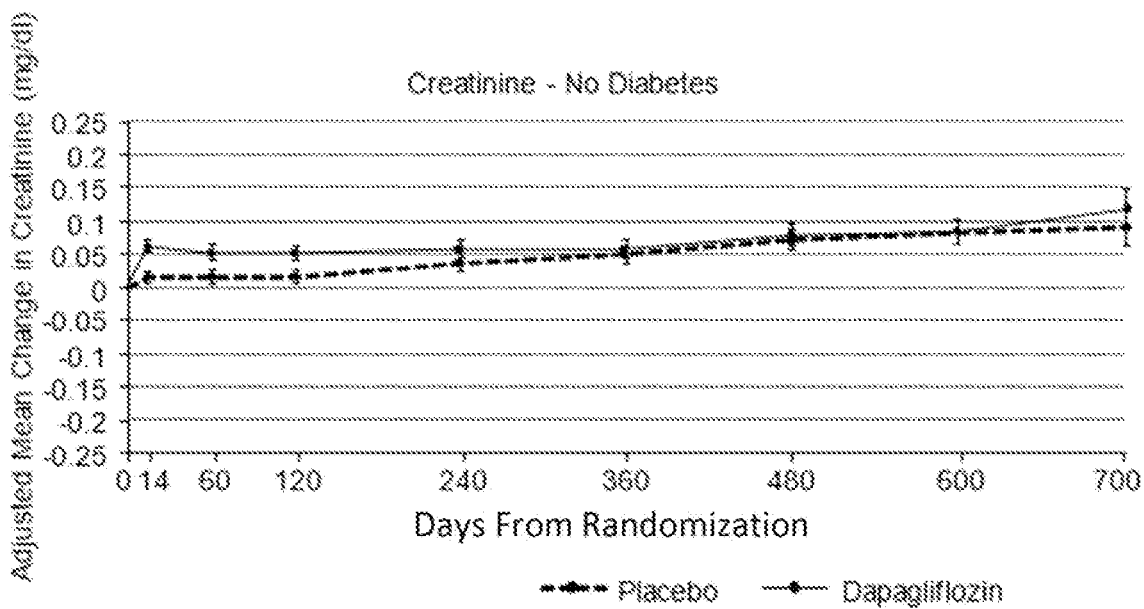
Figure 12A:
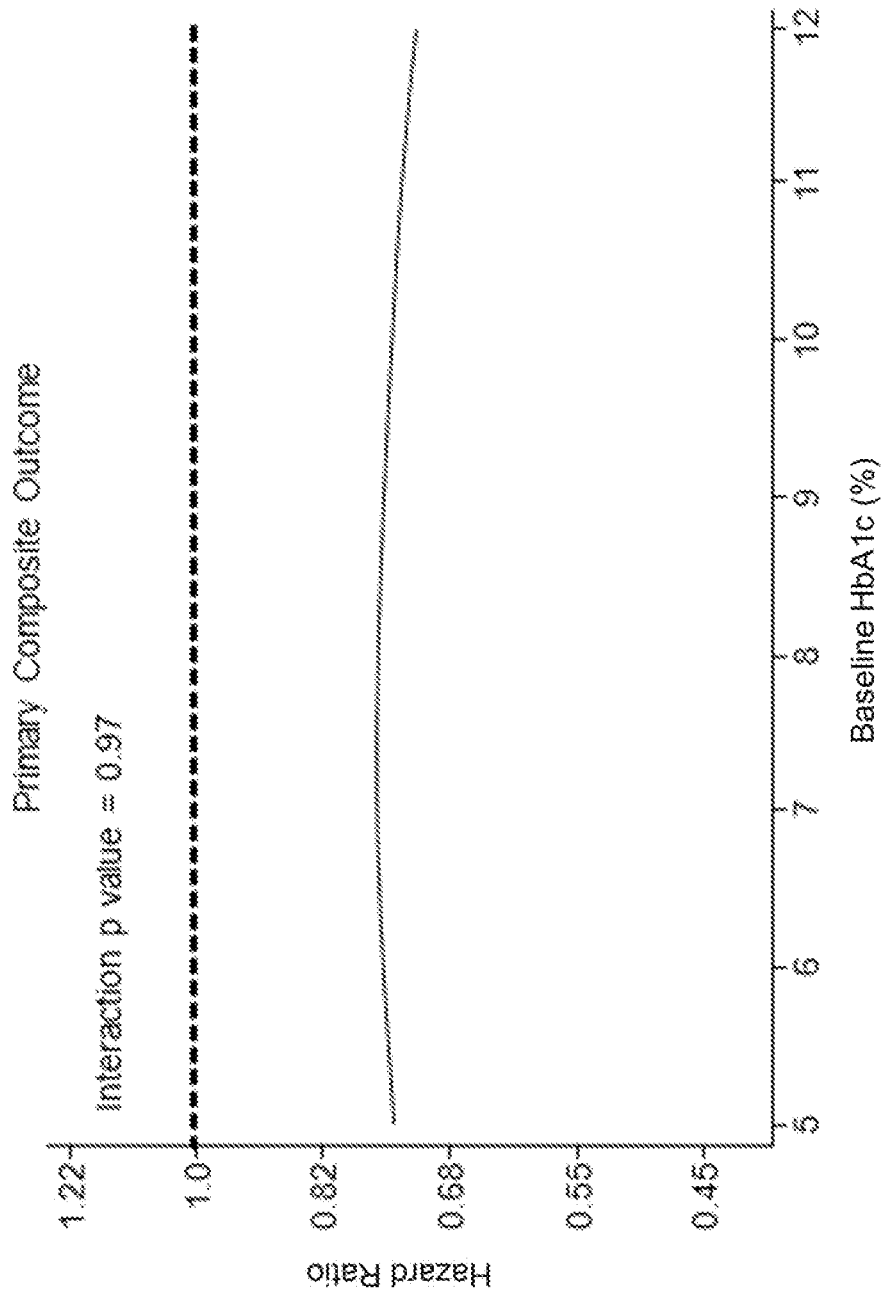
FIGS. 12A-12D are graphs depicting outcomes according to glycated HbA1c levels (as a continuous variable) at baseline, including: primary composite outcome (FIG. 12A); hospitalization or an urgent visit for heart failure (FIG. 12B); death from cardiovascular causes (FIG. 12C); and death from any cause (FIG. 12D).
Figure 12B:
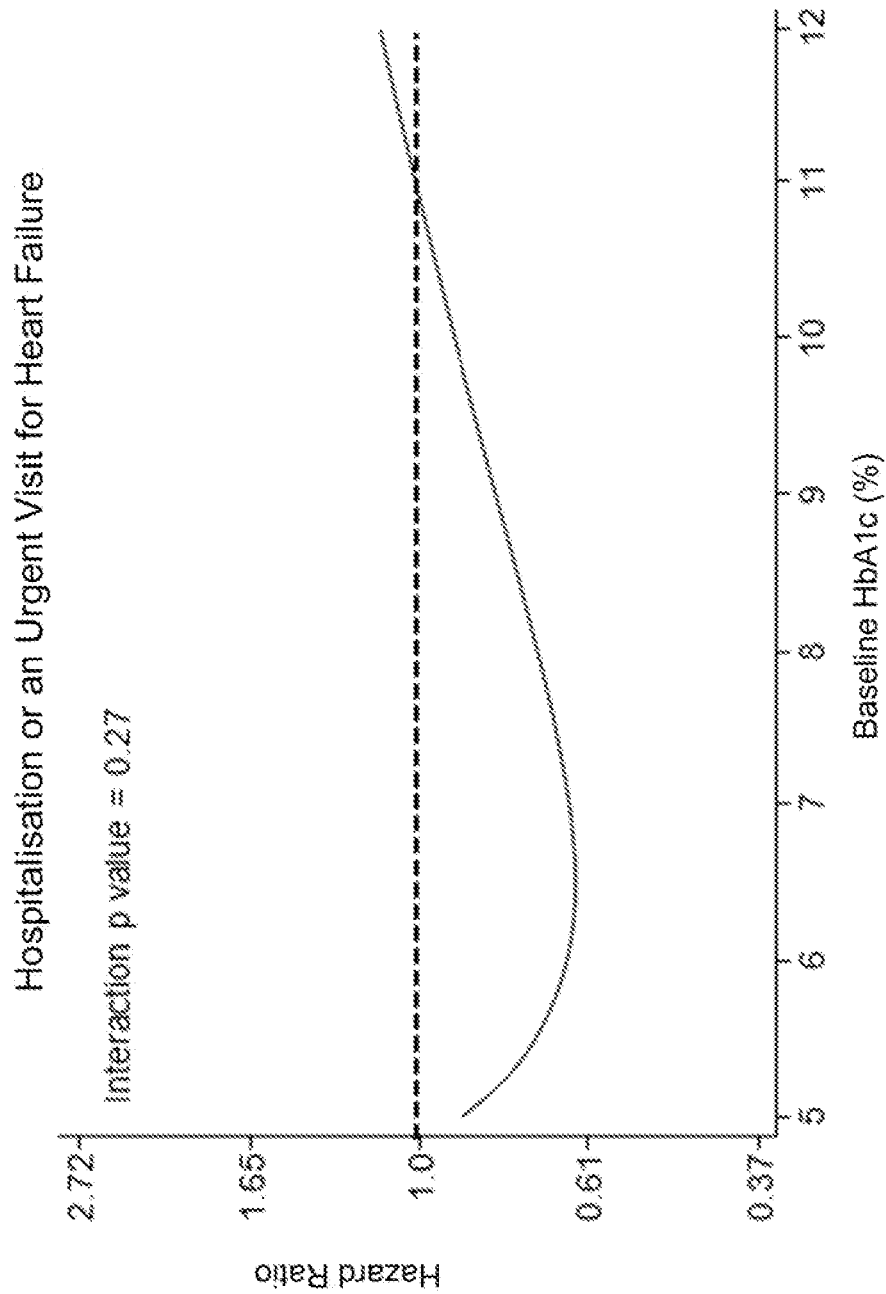
Figure 12C:
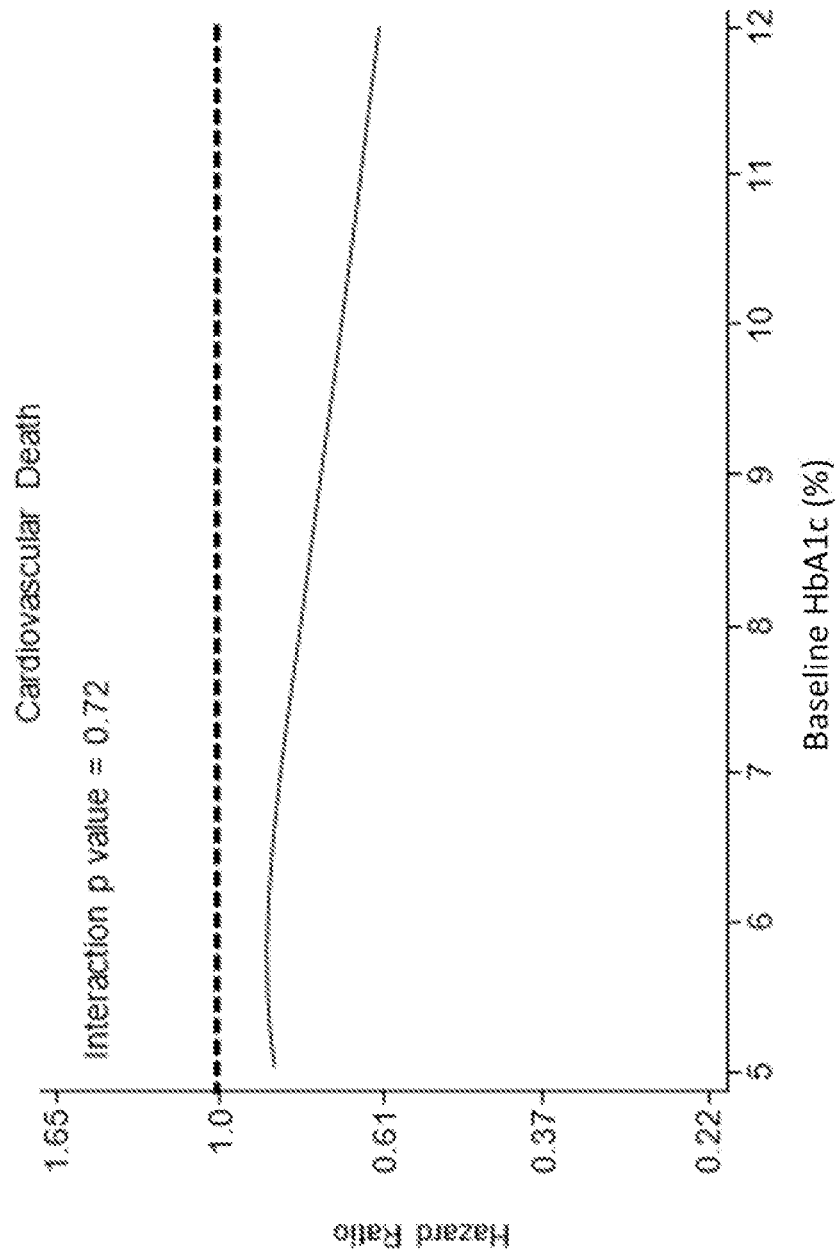
Figure 12D:
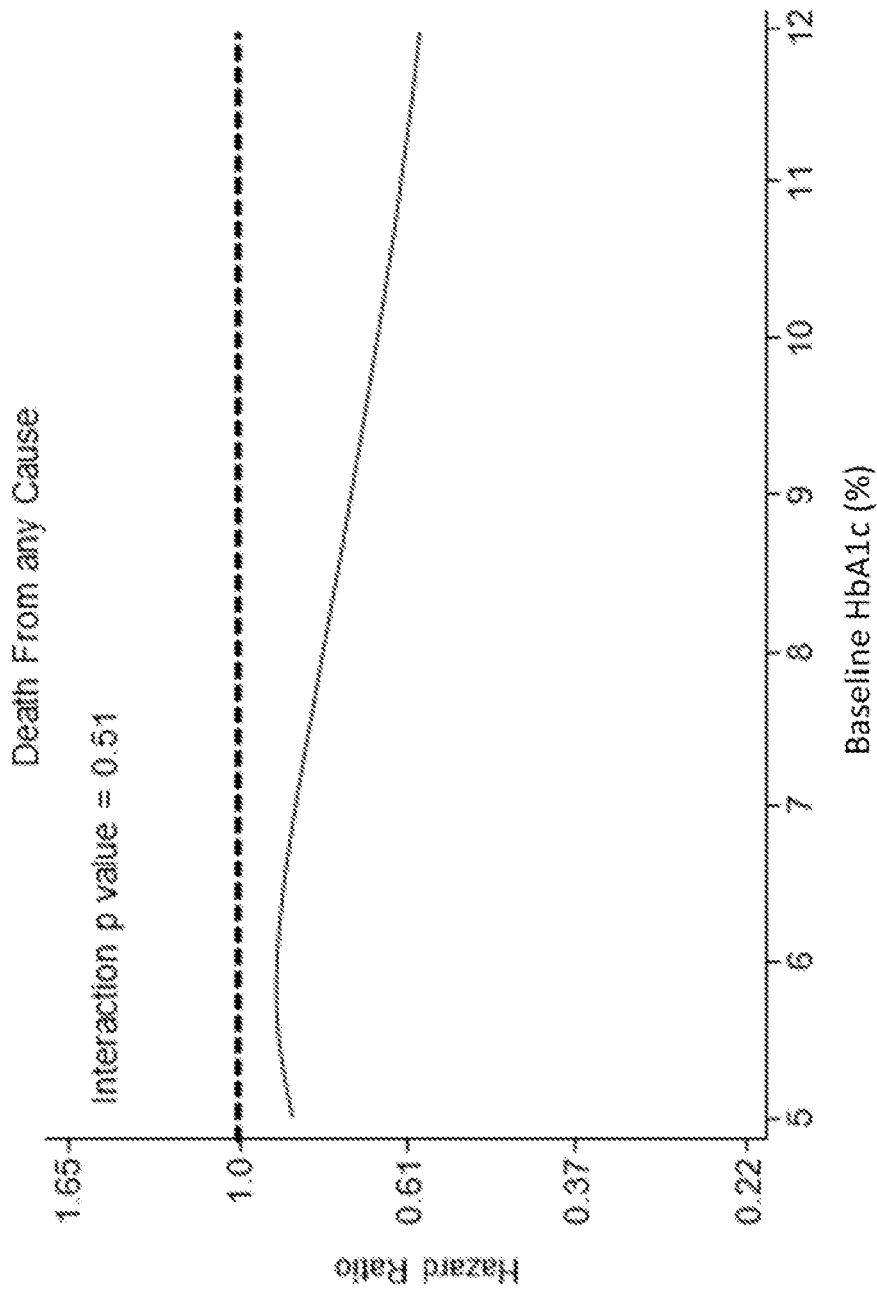
Figure 13:
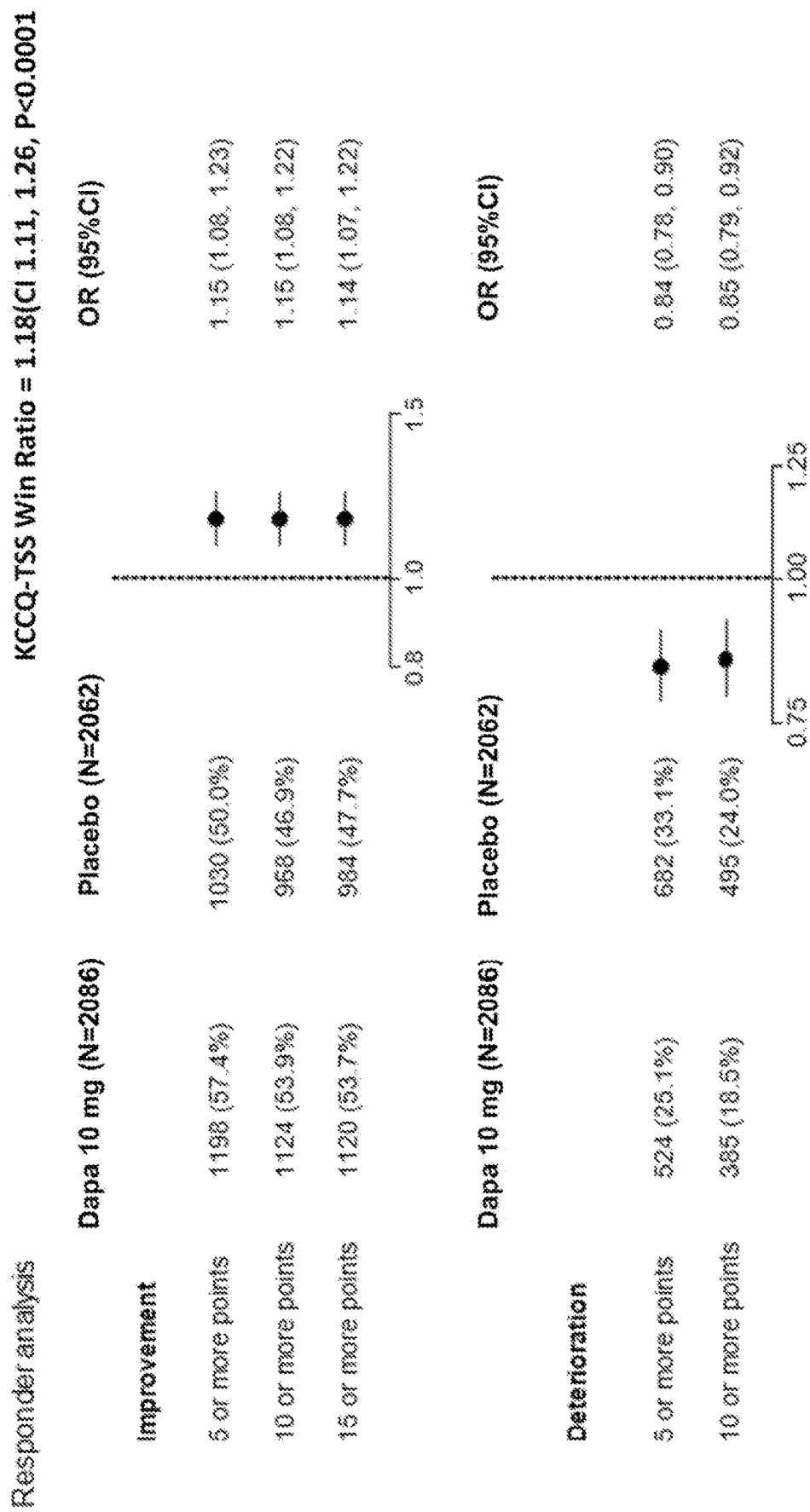
FIG. 13 depicts a responder analysis showing consistent symptom benefit to patients administered dapagliflozin vs. placebo (e.g., 5 or more points, 10 or more points, 15 or more points), irrespective of threshold KCCQ-TSS scores, at 8 months.

FIGS. 11A-11J show changes in laboratory measures, weight, and blood pressure, adjusting for baseline value. There was little change in glycated hemoglobin in patients without diabetes, while in patients with diabetes there was a modest reduction by 60 days (P interaction <0.0001) (FIGS. 11A-11B). Weight and systolic blood pressure declined in both patient groups (FIGS. 11C-11D and FIGS. 11E-11F, respectively). Hematocrit increased with dapagliflozin in both patient groups with plateau reached after approximately 4 months; the increase was less in patients without diabetes than in those with diabetes (P interaction=0.0002) (FIGS. 11G-11H). There was a small initial increase in creatinine with dapagliflozin in both groups although the between-treatment difference had attenuated by 6 months; the increase was less in patients without diabetes than in those with diabetes (P interaction=0.0005) (FIGS. 11I-11J).

N-Terminal Pro-B-Type Natriuretic Peptide

In patients without diabetes, NT-proBNP decreased by 144±2286 pg/ml in the dapagliflozin group and increased by 84±2993 pg/ml in the placebo group, between baseline and 8 months; between-treatment difference −278 (−485 to −71) pg/ml; p=0.009. The corresponding changes in participants with diabetes were a decrease of 257±2502 pg/ml in the dapagliflozin group and an increase of 121±2884 pg/ml in the placebo group; between-treatment difference −333 (−562 to −104) pg/ml; p=0.004 (P interaction=0.728).

Tolerability and Safety

Among patients without diabetes, 144 patients (11.1%) in the dapagliflozin group and 141 patients (10.8%) in the placebo group stopped study medication. In patients with diabetes, these numbers were 105 (9.8%) and 117 (11.0%), respectively.

The most common adverse events of interest were those related to volume depletion and renal impairment, which were less common in patients without diabetes than in participants with diabetes (Table 8). The incidence of these adverse events did not differ between dapagliflozin and placebo in either patient group.

TABLE 8

Adverse Events of interest, leading to discontinuation of study drug

| Variable | Dapagliflozin (N = 2368)* No T2DM (N = 1295) T2DM (N = 1073) No. (%) | Placebo (N = 2368)* No T2DM (N = 1305) T2DM (N = 1063) No. (%) | P-value |
|---|---|---|---|
| Any serious adverse event (including death) | | | |
| No T2DM | 448 (34.6) | 481 (36.9) | 0.24 |
| T2DM | 447 (41.7) | 513 (48.3) | 0.002 |
| Discontinuation of study drug due to adverse event | | | |
| No T2DM | 68 (5.3) | 59 (4.5) | 0.41 |
| T2DM | 43 (4.0) | 57 (5.4) | 0.15 |
| Adverse events of interest Volume depletion | | | |
| No T2DM | 94 (7.3) | 79 (6.1) | 0.24 |
| T2DM | 84 (97.8) | 83 (7.8) | 1.00 |

TABLE 8-continued

Adverse Events of interest, leading to discontinuation of study drug

| Variable | Dapagliflozin (N = 2368)* No T2DM (N = 1295) T2DM (N = 1073) No. (%) | Placebo (N = 2368)* No T2DM (N = 1305) T2DM (N = 1063) No. (%) | P-value |
|---|---|---|---|
| Renal adverse event | | | |
| No T2DM | 62 (4.8) | 78 (6.0) | 0.19 |
| T2DM | 91 (8.5) | 92 (8.7) | 0.94 |
| Fracture | | | |
| No T2DM | 27 (2.1) | 25 (1.9) | 0.78 |
| T2DM | 22 (2.1) | 25 (2.4) | 0.66 |
| Amputation | | | |
| No T2DM | 1 (0.1) | 3 (0.2) | NA |
| T2DM | 12 (1.1) | 9 (0.8) | 0.66 |
| Major hypoglycaemia‡‡ | | | |
| No T2DM | 0 (0) | 0 (0) | NA |
| T2DM | 4 (0.4) | 4 (0.4) | NA |
| Diabetic ketoacidosis | | | |
| No T2DM | 0 (0) | 0 (0) | NA |
| T2DM | 3 (0.3) | 0 (0) | NA |
| Fournier gangrene | | | |
| No T2DM | 0 (0) | 0 (0) | NA |
| T2DM | 0 (0) | 1 (0.1) | NA |

T2DM = type 2 diabetes mellitus.
NA denotes not applicable because P values are not reported for outcomes with 10 events or fewer.
*The safety population included patients receiving at least one dose of trial medication: dapagliflozin n = 2368 and placebo n = 2368. The numbers reported are patients.
‡‡Major hypoglycemia was defined as hypoglycemia requiring the assistance of another person to actively administer carbohydrates, glucagon, or take other corrective action.

Doubling of serum creatinine occurred in 22 patients (1.7%) without diabetes assigned to dapagliflozin and 36 patients (2.8%) assigned to placebo, P=0.08; the corresponding numbers among participants with diabetes were 21 (2.0%) and 41 (3.9%), P=0.01.

Three patients (0.06%) experienced definite or probable diabetic ketoacidosis in the trial, and all were patients with diabetes randomized to dapagliflozin. Eight patients (0.17%) experienced major hypoglycemia in the trial, and all eight had diabetes: four randomized to dapagliflozin and four assigned to placebo. Overall, 25 patients (0.53%) had an amputation, one in the dapagliflozin group and three in the placebo group among individuals without diabetes, with twelve cases in the dapagliflozin group and nine cases in the placebo group, among patients with diabetes.

Discussion

The key finding from this analysis of patients with HF and reduced ejection fraction was that the SGLT2 inhibitor dapagliflozin improved all prespecified mortality and hospitalization outcomes to a similar extent in people with and without diabetes. Furthermore, among the individuals without diabetes, the reduction in the primary outcome with dapagliflozin was consistent across the range of glycated hemoglobin levels at baseline, whether evaluated as a categorical or continuous measure. Indeed, by chance, the tertile analysis in participants without diabetes selected quantiles reflecting U.S. (≥5.6%) and European (≥6.0%) definitions of prediabetes, based on glycated hemoglobin criteria. (American Diabetes Association. 2. Classification and Diagnosis of Diabetes: Standards of Medical Care in Diabetes-2019, *Diabetes Care* 42 (Suppl 1): S13-S28 (2019); Chatterton, H. et al., *BMJ* 345: e4624 (2012)). The benefit of dapagliflozin was similar in individuals with prediabetes, diagnosed using either definition, and in those with a normal glycated hemoglobin. This data provides compelling evidence that the benefits of SGLT2 inhibition are not limited to people with diabetes or prediabetes and are applicable to patients with heart failure and reduced ejection fraction, irrespective of glycemic status. Moreover, the benefits observed were obtained in participants already receiving recommended therapy for HF, including renin-angiotensin system blockers, beta-blockers, and mineralocorticoid receptor antagonists.

The present analyses also demonstrate the effects of dapagliflozin on metabolic, hemodynamic and anthropometric measures in people with and without diabetes. As expected, dapagliflozin reduced glycated hemoglobin in patients with type 2 diabetes but had no effect on this measure in people without diabetes. However, the effects of dapagliflozin on weight, blood pressure, hematocrit, creatinine and NT-proBNP were directionally similar in those with and without diabetes, although somewhat more pronounced in the former group.

It can be inferred from the findings of this trial that the benefits of dapagliflozin were independent of lowering of plasma glucose. Other mechanisms of action for SGLT2 inhibitors have been proposed, including a diuretic effect. (Hallow, K. M. et al., *Diabetes Obes Metab* 20: 479-487 (2018); McMurray, J., *J Diabetes Complications* 30:3-4 (2016)). While this mechanism was not measured directly in the present trial, the early decreases in systolic blood pressure and weight, and increase in creatinine, were consistent with a diuretic action. However, very little is known about the effects of SGLT2 inhibitors on urinary sodium and water excretion when added to conventional diuretic therapy, especially in patients with HF, and particularly in those without diabetes. (Hallow, K. M. et al., supra; Devineni, D. et al., *Clin Ther* 36: 698-710 (2014); Nassif, M. E. et al., *Circulation* (2019 September); Kosiborod, M. et al., *J Diabetes Complications* 31: 1215-1221 (2017)). There are also other potential explanations for the increase in creatinine and hematocrit. SGLT2 inhibitors are believed to cause tubulo-glomerular feedback, independently of diuresis, which promotes constriction of the afferent glomerular arteriole and reduction in glomerular filtration rate. (Heerspink, H. K. et al., *Circulation* 134: 752-72 (2016); Kidokoro, K. et al., *Circulation* 140: 303-315 (2019). Likewise, the rise in hematocrit may be due to an increase in renal erythropoietin secretion due to SGLT2 inhibitor mediated improvements in kidney function. (Yanai, H. et al., *J Clin Med Res* 9:178-179 (2017)). The time course of the changes in creatinine and hematocrit we observed were quite different, with the initial increase in creatinine reversing after 14 days, whereas hematocrit increased progressively over the first 4 months, plateauing thereafter. Volume contraction due to diuresis is unlikely to explain such divergent changes.

Other diuresis-independent actions including effects on ion transporters, fibrosis, adipokines, sympathetic nervous system activity, and vascular function have also been proposed, although clinical evidence supporting these is sparse. (Thomas, M. C. et al., *Diabetologia* 61:2098-2107 (2018); Garg, V. et al., *Prog Cardiovasc Dis* pii: S0033-0620 (19) 30102-1 (2019); Wojcik, C. et al., *Curr Cardiol Rep* 21: 130 (2019); Verma S. et al., *Diabetologia* 61: 2108-2117 (2018). Some data suggest that SGLT2 inhibitors may reduce left ventricular mass and an effect on cardiac remodeling could explain the decrease observed in NT-proBNP with dapagliflozin. (Verma, S. et al., *Circulation* (2019 Aug. 22)). Recent experimental studies have also shown a benefit of SGLT2 inhibitors on cardiac structure and function in animals without diabetes. (Thomas, M. C. et al., *Diabetologia* 61:2098-2107 (2018); Yurista, S. R. et al., *Eur J Heart Fail* 21:862-873 (2019); Garg, V. et al., *Prog Cardiovasc Dis* pii: 50033-0620 (19) 30102-1 (2019)). Prevention of decline in renal function is also likely to be beneficial in heart failure.

The overall rate of the other key adverse events of interest in the context of heart failure, those related to volume depletion, was low and similar in participants with and without diabetes. This finding is also in keeping with the view that a diuretic action is unlikely to be the key mechanism underlying the beneficial effects of dapagliflozin. Other prespecified safety outcomes were infrequent in both groups of patients and discontinuation of study drug was also uncommon in the two groups. Neither major hypoglycemia, nor diabetic ketoacidosis, occurred in any patient without diabetes. Although a significant effect on our prespecified renal outcome was not shown, this occurred in few patients. It was found, however, that doubling of serum creatinine was significantly less common in patients receiving dapagliflozin, both in patients with and without diabetes. Serious renal adverse events were also less common in patients assigned to dapagliflozin, compared with placebo.

In conclusion, in patients with HF and reduced ejection fraction, the SGLT2 inhibitor dapagliflozin reduced the risk of worsening heart failure and death from cardiovascular causes, and improved symptoms, irrespective of baseline diabetes status and independently of glycated hemoglobin level. These benefits were observed on-top of excellent standard care in both people with and without diabetes. Taken together, these data support the use of dapagliflozin as a treatment of heart failure with reduced ejection fraction, in people with and without diabetes, and irrespective of glycemic status.

All references, including publications, patent applications, and patents, cited herein are hereby incorporated by reference to the same extent as if each reference were individually and specifically indicated to be incorporated by reference and were set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Various embodiments of this disclosure are described herein, including the best mode known to the inventors for carrying out the disclosure. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Example 4

DAPA-HF Phase III Clinical Trial Results—Effect of Dapagliflozin on Reduction of Hyperkalemia in HF patients Introduction Hyperkalemia often limits the use of mineralocorticoid receptor antagonists (MRAs) in patients with heart failure and reduced ejection fraction (HFrEF), denying these patients a life-saving therapy. In the prespecified analysis presented in this Example, the efficacy of sodium-glucose cotransporter 2 (SGLT-2) inhibitor dapagliflozin was assessed to determine whether treatment with dapagliflozin reduces the risk of hyperkalemia associated with MRA use in patients with HFrEF.

Methods

The risk of developing mild hyperkalemia (potassium >5.5 mmol/L) and moderate/severe hyperkalemia (>6.0 mmol/L) was examined in the Dapagliflozin And Prevention of Adverse-outcomes in Heart Failure trial (DAPA-HF) according to background MRA use, and randomized treatment assignment, by use of Cox regression analyses.

Results

Figure 18A:
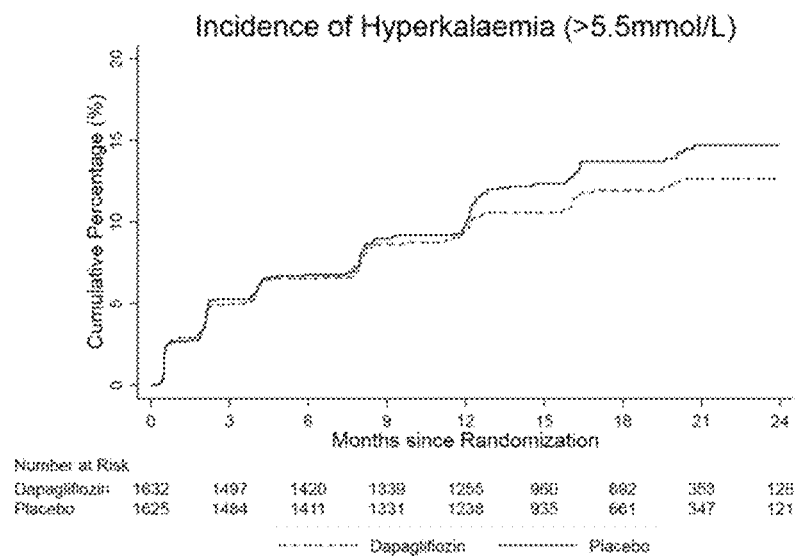
FIGS. 18A-18B describe the cumulative incidence of moderate hyperkalemia (>5.5 mmol/L) (FIG. 18A) and severe hyperkalemia (>6.0 mmol/L) (FIG. 18B) in patients treated with a mineralocorticoid receptor antagonist in the placebo (undashed line) and dapagliflozin (dashed line) groups
Figure 18B:
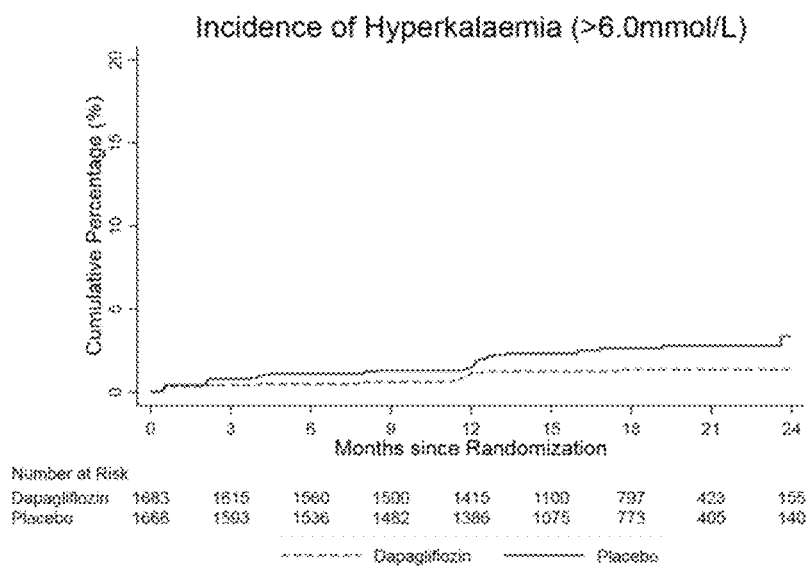

Overall, 3370 (70.1%) patients in DAPA-HF were treated with an MRA. Mild hyperkalemia and moderate/severe hyperkalemia occurred in 180 (11%) and 21 (1.2%) patients treated with dapagliflozin as compared to 204 (12.6%) and 40 (2.4%) of patients given placebo (Table 8 and FIGS. 18A-18B). This yielded a hazard ratio (HR) of 0.86 (0.70-1.05) for mild hyperkalemia and 0.50 (0.29, 0.85) for moderate/severe hyperkalemia, comparing dapagliflozin to placebo. Treatment with dapagliflozin halved the incidence of moderate/severe hyperkalemia associated with MRA use in patients with HFrEF.

TABLE 9

Incident hyperkalemia in DAPA-HF

| | Dapagliflozin | | Placebo | | | |
|---|---|---|---|---|---|---|
| | No. events/ patients | rate per 100 py | No. events/ patients | rate per 100 py | HR (95% CI) | P |
| Mild hyperkalemia (>5.5 mmol/L)* | | | | | | |
| No MRA at baseline | 63/660 | 7.1 | 57/682 | 6.4 | 1.20 (0.84-1.72) | 0.32 |
| MRA treated at baseline | 180/1632 | 8.6 | 204/1625 | 9.8 | 0.86 (0.70-1.05) | 0.14 |
| All patients | 243/2292 | 8.1 | 261/2307 | 8.8 | 0.93 (0.78-1.11) | 0.42 |
| Moderate/Severe hyperkalemia (>6.0 mmol/L)** | | | | | | |
| No MRA at baseline | 13/675 | 1.4 | 11/695 | 1.2 | 1.17 (0.52-2.62) | 0.71 |
| MRA treated at baseline | 21/1683 | 0.9 | 40/1666 | 1.7 | 0.50 (0.29-0.85) | 0.010 |
| All patients | 34/2358 | 1.0 | 51/2361 | 1.6 | 0.64 (0.42-0.99) | 0.046 |

*Models adjusted for baseline potassium and stratified by diabetes status at randomization.
*Excluding those with baseline K$^+$ > 5.5 (n = 145)
** Excluding those with baseline K$^+$ > 6.0 (n = 25)

The invention claimed is:

1. A method of reducing the risk of cardiovascular death and worsening heart failure in a patient with heart failure with reduced ejection fraction (HFrEF), comprising administering to the patient a pharmaceutical composition comprising a therapeutically effective amount of dapagliflozin, wherein the patient does not have type II diabetes and has a glycated hemoglobin level (HbA1c) of <5.7%.

2. The method of claim 1, wherein worsening heart failure comprises unplanned hospitalization(s) for heart failure and/or urgent heart failure visit(s).

3. The method of claim 2, wherein unplanned hospitalization(s) for heart failure is due to one or more of the following:
   (a) new or worsening symptoms of HF experienced by the patient, and/or
   (b) objective evidence of new or worsening symptoms of HF; and/or
   (c) initiation of intensification of treatment specifically for HF.

4. The method of claim 3, wherein unplanned hospitalization(s) for heart failure includes first and/or recurrent hospitalizations for HF.

5. The method of claim 2, wherein urgent HF visit(s) includes one or more of the following:
   (a) an emergency room visit for a primary diagnosis of HF, not requiring hospitalization;
   (b) an emergency room visit for a primary diagnosis of HF, requiring treatment other than just an increase in oral diuretics, but not requiring hospitalization;
   (c) an urgent unscheduled visit to a physician's office for a primary diagnosis of HF;
   (d) an urgent unscheduled visit to a physician's office requiring treatment other than just an increase in oral diuretics;
   (e) initiation or intensification of treatment specifically for HF; and/or
   (f) initiation of intravenous therapy.

6. The method of claim 1, wherein the amount of dapagliflozin administered is 10 mg daily.

7. The method of claim 1, wherein the method further improves heart failure symptoms.

8. The method of claim 7, wherein the improvement in heart failure symptoms is measured by a patient's higher score on the KCCQ TSS compared to the patient's score prior to initiation of treatment with a pharmaceutical composition comprising a therapeutically effective amount of dapagliflozin.

9. The method of claim 8, wherein the higher score on the KCCQ TSS is at least 5 points higher than the score prior to administration with a pharmaceutical composition comprising a therapeutically effective amount of dapagliflozin.

10. The method of claim 8, wherein the higher score on the KCCQ TSS is at least 10 points higher than the score prior to administration with a pharmaceutical composition comprising a therapeutically effective amount of dapagliflozin.

11. The method of claim 8, wherein the higher score on the KCCQ TSS is at least 15 points higher than the score prior to administration with a pharmaceutical composition comprising a therapeutically effective amount of dapagliflozin.

12. The method off claim 7, wherein the improvement in heart failure symptoms is measured by a patient's score on the KCCQ TSS.

13. The method of claim 1, wherein the method satisfies at least one of the following conditions:
   a) the method numerically reduces that absolute risk of the composite endpoint of hospitalization for HF, cardiovascular death or urgent HF visit in a patient;
   b) the method results in a nominally significant risk reduction of the composite endpoint of hospitalization for HF, cardiovascular death or urgent HF visit in a patient;
   c) the method results in a numerical reduction in the composite endpoint events of hospitalization for HF, cardiovascular death or urgent HF visit in a patient;
   d) the method results in a numerical reduction in the risk of composite endpoint events of hospitalization for HF, cardiovascular death or urgent HF visit in a patient;
   e) the method results in a decrease in mean change of NT-proBNP levels in a patient within 8 months of the start of treatment; and/or
   f) the method results in a decrease in mean change of NT-probBNP levels of −278 pg/ml in a patient within 8 months of the start of treatment.

14. The method of claim 1, wherein the method satisfies at least one of the following conditions:

a) the method numerically reduces the absolute risk of the composite endpoint of hospitalization for HF or cardiovascular death in a patient;
b) the method results in a nominally significant reduction in the risk of the composite endpoint of hospitalization for HF or cardiovascular death in a patient;
c) the method results in a numerical reduction in the composite endpoint of hospitalization for HF or cardiovascular death in a patient; and/or
d) the method results in a numerical reduction in the risk of composite endpoint of hospitalization for HF or cardiovascular death in a patient.

15. The method of claim 1, wherein the method satisfies at least one of the following conditions:
    a) the method numerically reduces the absolute risk of all-cause mortality;
    b) the method results in a nominally significant reduction in the risk of all-cause mortality in a patient;
    c) the method results in a numerical reduction in all-cause mortality; and/or
    d) the method results in a numerical reduction in the risk of all-cause mortality in a patient.

16. The method of claim 1, wherein the method satisfies at least one of the following conditions:
    a) the method numerically reduces the absolute risk of the total number of hospitalizations for HF events (first and recurrent) and CV death in a patient;
    b) the method results in a nominally significant reduction in the rate of total number of hospitalizations for HF events (first and recurrent) and CV death in a patient;
    c) the method results in a numerical reduction in the total number of hospitalizations for HF events (first and recurrent) and CV death in a patient; and/or
    d) the method results in a numerical reduction in the risk of total number of hospitalizations for HF events (first and recurrent) and CV death in a patient.

17. A method of reducing the risk of hospitalization for heart failure and cardiovascular death in a patient following an acute myocardial infarction, comprising administering to the patient a pharmaceutical composition comprising a therapeutically effective amount of dapagliflozin,
    wherein the patient does not have type II diabetes and has a glycated hemoglobin level (HbA1c) of <5.7%.

18. The method of claim 17, wherein the patient has experienced an acute myocardial infarction within 7 days from initiation of treatment with a pharmaceutical comprising a therapeutically effective amount of dapagliflozin.

19. The method of claim 18, where the acute myocardial infarction is a ST segment elevation myocardial infarction (STEW) or a non-ST segment elevation myocardial infarction.

20. The method of claim 17, wherein the hospitalizations for heart failure is due to one or more of the following:
    (i) new or worsening symptoms of HF experienced by the patient;
    (ii) objective evidence of new or worsening symptoms of HF; and/or
    (iii) initiation or intensification of treatment specifically for HF.

21. The method of claim 20, wherein the hospitalizations for heart failure includes first and/or recurrent hospitalizations for HF.

22. A method of reducing the risk of cardiovascular death or worsening heart failure symptoms in patients with acute decompensated heart failure, comprising administering to the patient a pharmaceutical composition comprising a therapeutically effective amount of dapagliflozin;
    wherein the patient does not have type II diabetes and has a glycated hemoglobin level (HbA1c) of <5.7%.

23. The method of claim 22, wherein the patient is hospitalized in stable condition for worsening heart failure symptoms or acute decompensated heart failure.

24. The method of claim 22, wherein the patient has a left ventricular ejection fraction (LVEF) of less than or equal to 40%.

25. The method of claim 22, wherein the reduction in the rate of worsening heart failure symptoms is satisfied by a reduction in hospitalizations for heart failure or reduction in urgent HF visits.

26. The method of claim 25, wherein the hospitalizations for heart failure includes first and/or recurrent hospitalizations for HF and is due to one or more of the following:
    (i) new or worsening symptoms of HF experienced by the patient;
    (ii) objective evidence of new or worsening symptoms of HF; and/or
    (iii) initiation or intensification of treatment specifically for HF.

27. The method of claim 25, wherein the urgent HF visits requires treatment for worsening heart failure other than just an increase in oral diuretics.

* * * * *

UNITED STATES PATENT AND TRADEMARK OFFICE
CERTIFICATE OF CORRECTION

PATENT NO. : 11,903,955 B2  
APPLICATION NO. : 17/184746  
DATED : February 20, 2024  
INVENTOR(S) : Anna Maria Langkilde Page 1 of 1

It is certified that error appears in the above-identified patent and that said Letters Patent is hereby corrected as shown below:

In the Claims

Claim 12, Column 66, Line 42, "off" should read "of"

Claim 19, Column 68, Line 3, "(STEW)" should read "(STEMI)"

Signed and Sealed this  
Ninth Day of April, 2024

Katherine Kelly Vidal  
*Director of the United States Patent and Trademark Office*